United States Patent
Dunn et al.

(10) Patent No.: US 11,820,826 B2
(45) Date of Patent: Nov. 21, 2023

(54) ANTI-NPR1 ANTIBODIES AND USES THEREOF

(71) Applicant: Regeneron Pharmaceuticals, Inc., Tarrytown, NY (US)

(72) Inventors: Michael E. Dunn, Montvale, NJ (US); Jia Su, Scarsdale, NY (US); Jason Mastaitis, Yorktown Heights, NY (US); Jesper Gromada, Scarsdale, NY (US); Lori C. Morton, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/692,084

(22) Filed: Mar. 10, 2022

(65) Prior Publication Data

US 2022/0204634 A1     Jun. 30, 2022

Related U.S. Application Data

(62) Division of application No. 16/657,000, filed on Oct. 18, 2019, now Pat. No. 11,306,148.

(60) Provisional application No. 62/755,720, filed on Nov. 5, 2018, provisional application No. 62/749,557, filed on Oct. 23, 2018.

(51) Int. Cl.
| | | |
|---|---|---|
| *C07K 16/28* | (2006.01) | |
| *A61K 39/395* | (2006.01) | |
| *A61P 9/02* | (2006.01) | |
| *A61P 3/04* | (2006.01) | |
| *A61P 9/12* | (2006.01) | |
| *A61K 9/00* | (2006.01) | |
| *A61K 45/06* | (2006.01) | |

(52) U.S. Cl.
CPC ........ *C07K 16/2869* (2013.01); *A61K 9/0019* (2013.01); *A61K 39/3955* (2013.01); *A61K 45/06* (2013.01); *A61P 3/04* (2018.01); *A61P 9/02* (2018.01); *A61P 9/12* (2018.01); *C07K 2317/21* (2013.01); *C07K 2317/34* (2013.01); *C07K 2317/565* (2013.01); *C07K 2317/75* (2013.01); *C07K 2317/76* (2013.01); *C07K 2317/92* (2013.01)

(58) Field of Classification Search
CPC ............ C07K 16/2869; C07K 2317/75; A61K 39/3955
See application file for complete search history.

(56) References Cited

U.S. PATENT DOCUMENTS

| | | |
|---|---|---|
| 6,596,541 B2 | 7/2003 | Murphy et al. |
| 7,582,298 B2 | 9/2009 | Stevens et al. |
| 8,246,995 B2 | 8/2012 | Dai et al. |
| 8,257,740 B1 | 9/2012 | Sung et al. |
| 9,090,695 B2 | 7/2015 | Waterman et al. |
| 11,306,148 B2 | 4/2022 | Dunn |
| 2004/0101920 A1 | 5/2004 | Radziejewski et al. |
| 2010/0331527 A1 | 12/2010 | Davis et al. |
| 2011/0195454 A1 | 8/2011 | McWhirter et al. |
| 2012/0114659 A1 | 5/2012 | Waterman et al. |
| 2012/0270923 A1 | 10/2012 | Mohapatra et al. |
| 2014/0031234 A1 | 1/2014 | Despres |
| 2014/0243504 A1 | 8/2014 | Davis et al. |
| 2014/0343120 A1 | 11/2014 | Mohapatra |
| 2016/0168251 A1 | 6/2016 | Waterman et al. |
| 2016/0199487 A1 | 7/2016 | Gu et al. |
| 2020/0123263 A1 | 4/2020 | Dunn |
| 2022/0195058 A1 | 6/2022 | Dunn |
| 2023/0250170 A1 | 8/2023 | Dunn |

FOREIGN PATENT DOCUMENTS

| | | |
|---|---|---|
| WO | 91/17271 | 11/1991 |
| WO | 92/01047 | 1/1992 |
| WO | 05/103081 | 11/2005 |
| WO | 2010/065293 | 6/2010 |
| WO | 2016/131943 | 8/2016 |
| WO | 2017/209553 | 12/2017 |
| WO | 2019/090039 | 5/2019 |
| WO | 2020/086406 | 4/2020 |
| WO | 2020/131935 | 6/2020 |
| WO | 2020/250159 | 12/2020 |
| WO | 2022/130182 | 6/2022 |
| WO | 2022/133239 | 6/2022 |

OTHER PUBLICATIONS

Kitano, Katsuhiko, et al., "Production and characterization of monoclonal antibodies against human natriuretic peptide receptor-A or -B", Immunology Letters, vol. 47, No. 3, Sep. 1, 1995, pp. 215-222.
Solinski, Hans Jurgen, et al., "Inhibition of natriuretic peptide receptor 1 reduces itch in mice", Sci Transl Med, vol. 11, No. 10, Jul. 10, 2019, 15 pages.
Dondelinger, Mathieu, et al: "Understanding the Significance and Implications of Antibody Numbering and Antigen-Binding Surface/Residue Definition", Frontiers in Immunology, Oct. 16, 2018;9:Article 2278, 15 pages.
Bejamini, Eli, et al., "1991 Immunology: A Short Course", 2nd Edition, Wiley-Liss, Inc. New York, NY, USA, 1991, p. 40.
Ferrara, Fortunato, et al., "Recombinant renewable polyclonal antibodies", Jan./Feb. 2015 mAbs. 7(1): 32-41.
Garbers, David L. et al., "Membrane guanylyl cyclase receptors: an update", Trends in Endocrinology and Metabolism, vol. 17, No. 6, pp. 251-258.

(Continued)

*Primary Examiner* — Zachary C Howard
(74) *Attorney, Agent, or Firm* — Merchant & Gould P.C.

(57) ABSTRACT

The present invention provides monoclonal antibodies that bind to the natriuretic peptide receptor 1 (NPR1) protein, and methods of use thereof. In various embodiments of the invention, the antibodies are fully human antibodies that bind to NPR1. In some embodiments, the antibodies of the invention are useful for activating NPR1 activity, thus providing a means of treating or preventing a disease, disorder or condition associated with NPR1 in humans.

14 Claims, 23 Drawing Sheets
Specification includes a Sequence Listing.

(56) References Cited

OTHER PUBLICATIONS

Garbers, David L., The guanylyl cyclase receptors, Zygote 8 (Supplement) 2000, Cambridge Univ. Press, FDSUMI Symposium Proc., pp. S24-S25.
Kuhn, Michaela, (2003), "Structure, Regulation, and Function of Mammalian Membrane Guanylyl Cyclase Receptors, With a Focus on Guanylyl Cyclase-A", Circ. Res. 93: 700-709.
Lowe, D. G. et al., "Human natriuretic peptide receptor-A guanylyl cyclase. Hormone cross-linking and antibody reactivity distinguish receptor glycoforms", The Journal of Biological Chemistry, Oct. 25, 1992, vol. 267, No. 30, pp. 21691-21697.
Misono, Kunio S., (2011), Minireview, "Structure, signaling mechanism and regulation of the natriuretic peptide receptor guanylate cyclase", FEBS Journal 278: 1818-1829.
Mohapatra, Shyam S., (2007), "Role of natriuretic peptide signaling in modulating asthma and inflammation", Can. J. Physiol. Pharmacol. 85: 754-759.
Oliver, Paula M. et al., "Natriuretic peptide receptor 1 expression influences blood pressures of mice in a dose-dependent manner", Proc. Natl. Acad. Sci. USA, vol. 95, pp. 2547-2551, Mar. 1998.
Pandey, Kailash N., (2011), "The functional genomics of guanylyl cyclase/natriuretic peptide receptor-A: Perspectives and paradigms", Minireview, the FEBS Journal 278: 1792-1807.
Pandey, Kailash N., (2011), "Guanylyl cyclase / atrial natriuretic peptide receptor-A: role in the pathophysiology of cardiovascular regulation", Can. J. Physiol. Pharmacol. 89: 557-573.
PCT International Preliminary Report on Patentability in Application PCT/US2019/057033, dated May 6, 2021, 15 pages.
PCT International Search Report and Written Opinion in Application PCT/US2019/057033, dated May 8, 2020, 21 pages.
PCT Invitation to Pay Additional Fees, in Application PCT/US2019/057033, mailed Feb. 26, 2020, 19 pages.
Potter, Lincoln R. et al., (2006), "Natriuretic Peptides, Their Receptors, and Cyclic Guanosine Monophosphate-Dependent Signaling Functions", Endocrine Reviews 27(1): 47-72.
Potter, Lincoln R., "Guanylyl Cyclase-linked natriuretic Peptide Receptors: Structure and Regulation", The Journal of Biological Chemistry, vol. 276, No. 9, Issue of Mar. 2, 2001, pp. 6057-6060.
Potter, Lincoln R., "Regulation and Therapeutic Targeting of Peptide-Activated Receptor Guanylyl Cyclases", Pharmacology & Therapeutics 130 (2011) 71-82.
Sato, Yoshihiko et al., (2011), "Roles of guanylyl cyclase-A signaling in the cardiovascular system", Can. J. Physiol. Pharmacol. 89: 551-556.
Zhao, Zhilong, et al., (2013), "ANP-NPRA Signaling Pathway—A Potential Therapeutic Target for the Treatment of Malignancy", Critical Reviews in Eukaryotic Gene Expression, 23(2): 93-101.
PCT International Search Report and Written Opinion in International Application PCT/US2021/064073, dated Apr. 13, 2022, 25 pgs.
Cruz, Dinna, "Midodrine: a selective [alpha]—adrenergic agonist for orthostatic hypotension and dialysis hypotension", Expert Opin Pharmacother, vol. 1, No. 4, 1 May 2000, pp. 835-840.
Luscher, Thomas, et al., "From 'essential' hypertension to intensive blood pressure lowering: the pros and cons of lower target values", European Heart Journal, vol. 38, No. 44, Nov. 21, 2017, pp. 3258-3271.
Regeneron Pharmaceuticals: "Study to Assess the Safety, Tolerability, and Pharmacokinetics of REGN5381 (an NPR1 Agonist) in Adult Humans—NCT04506645", Clinical trials.gov, Aug. 10, 2020, XP055905554, Retrieved from the Internet: URL:https://clinicaltrials.gov/ct2/show/NCT04506645, [retrieved on Mar. 25, 2022], 20 pgs.
Regeneron Pharmaceuticals: "A Study to Evaluate the Safety, Tolerability, Pharmacokinetics, and Pharmacodynamics of REGN9035 in Healthy Adult Volunteers and Mildly Hypertensive Participants—NCT05291546", Clinical'Trials.gov, Mar. 22, 2022, XP055907382, Retrieved from the Internet: URL:https://clinicaltrials.gov/ct2/show/NCTO5291546?term=regn5381&draw=2&rank=2, [retrieved on Mar. 30, 2022], 10 pgs.
Blech, Michaela et al., "Structure of a Therapeutic Full-Length Anti-NPRA IgG4 Antibody: Dissecting Conformational Diversity", Biophys J. May 7, 2019; 116(9): 1637-1649, Published online Apr 5, 2019. doi: 10.1016/j.bpj.2019.03.036.
Bostrom, Jenny et al: "Improving antibody binding affinity and specificity for therapeutic development", Methods Mol Biol. 2009;525:353-76, xiii. Doi: 10.1007/978-1-59745-554-1_19.
Gonzales, Noreen R., et al., "Minimizing the Immunogenicity of Antibodies for Clinical Application", Tumour Biol. Jan.-Feb. 2005;26(1):31-43. doi: 10.1159/000084184.
Kunik, Vered et al., "Structural consensus among antibodies defines the antigen binding site", PLoS Comput Biol. 2012;8(2):e1002388. doi: 10.1371/journal.pcbi.1002388.Epub Feb. 23, 2012.
Kussie, Paul H. et al, "A Single Engineered Amino Acid Substitution Changes Antibody Fine Specificity", Journal of Immunology, 1994, 152: 146-152.
Morris, Glenn E., "Epitope Mapping of Protein Antigens by Competition ELISA", The Protein Protocols Handbook, Totowa, NJ, Humana Press, (Jan. 1, 1996), pp. 595-600,doi:10.1007/978-1-60327-259-9_96, ISBN 978-1-60-327259-9, DOI:http://dx.doi.org/10.1007/978-1-60327-259-9_96.
Panka, et al: "Variable region framework differences result in decreased or increased affinity of variant anti-digoxin antibodies", Proc Natl Acad Sci USA, May 1988;85(9):3080-4. doi: 10.1073/pnas.85.9.3080.
Rudikoff et al., "Single amino acid substitution altering antigen-binding specificity", Proc. Nat. Acad. Sci. USA vol. 79, pp. 1979-1983, Mar. 1982. DOIi: 10.1073/pnas.79.6.1979.
Wark, KL et al., "Latest technologies for the enhancement of antibody affinity", Advanced Drug Delivery Reviews, Elsevier, vol. 58, No. 5-6,doi:10.1016/J.ADDR.2006.01.025, ISSN 0169-409X, (Aug. 7, 2006), pp. 657-670.
Caton, Andrew et al., "Influenza virus hemagglutinin-specific antibodies isolated from a combinatorial expression library are closely related to the immune response of the donor", Proc. Natl. Acad. Sci., USA, 87:6450-6454, No. 16, Aug. 1990.
Chen et al., "Enhancement and destruction of antibody function by somatic mutation; unequal occurrence is controlled by V gene combinatorial associations", EMBO J, Jun. 15, 1995; 14(12):2784-94.
Verbrugge, Frederick et al., "Altered Hemodynamics and End-Organ Damage in Heart Failure", Sep. 8, 2000. Circulation 142(10):998-1012.

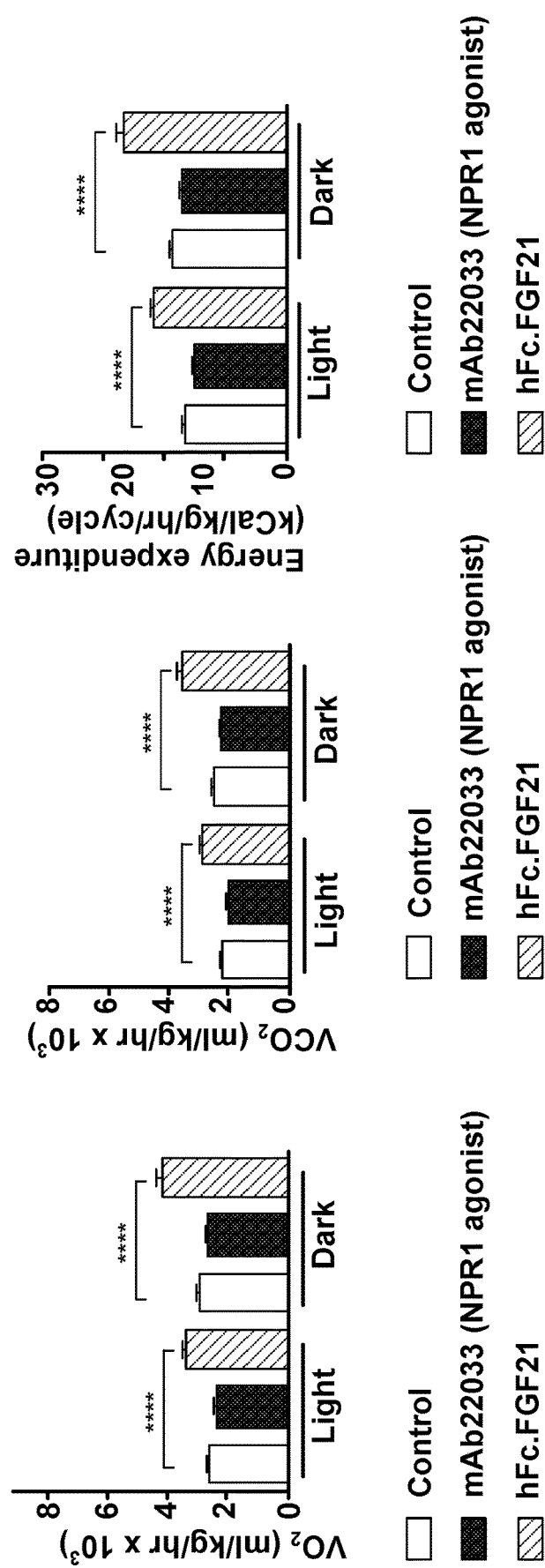

SEQUENCE LISTING

```
<160> NUMBER OF SEQ ID NOS: 199

<210> SEQ ID NO 1
<211> LENGTH: 372
<212> TYPE: DNA
<213> ORGANISM: Artificial Sequence
<220> FEATURE:
<223> OTHER INFORMATION: synthetic

<400> SEQUENCE: 1
```

```
caggtgcagc tggtgcagtc tggggctgag gtgaagaagc ctggggcctc agtgacggtc      60
tcctgcaagg cttctggata caccttcacc gactactata tgcactgggt gcgacaggcc     120
cctggacaag ggcttgagtg gatgggatgg atcaaaccta acagtggtgg cacaaactct     180
gcacagaggt tcagggcag aatcaccatg acctgggaca cgtccatcag cacagcctac     240
atggaactga gcaggctgag atctgacgac acggccgtgt attactgttc gagagggggc     300
ccagtcatga attactacta ctactacggt atggacgtct ggggccaagg gaccacggtc     360
accgtctcct ca                                                         372
```

<210> SEQ ID NO 2
<211> LENGTH: 124
<212> TYPE: PRT
<213> ORGANISM: Artificial Sequence
<220> FEATURE:
<223> OTHER INFORMATION: synthetic

<400> SEQUENCE: 2

```
Gln Val Gln Leu Val Gln Ser Gly Ala Glu Val Lys Lys Pro Gly Ala
1               5                  10                  15

Ser Val Thr Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Lys Pro Asn Ser Gly Gly Thr Asn Ser Ala Gln Arg Phe
    50                  55                  60

Gln Gly Arg Ile Thr Met Thr Trp Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ser Arg Gly Gly Pro Val Met Asn Tyr Tyr Tyr Tyr Gly Met Asp
            100                 105                 110

Val Trp Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3

```
ggatacacct tcaccgacta ctat                                             24
```

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

```
Gly Tyr Thr Phe Thr Asp Tyr Tyr
1               5
```

<210> SEQ ID NO 5
<211> LENGTH: 24
<212> TYPE: DNA
<213> ORGANISM: Artificial Sequence
<220> FEATURE:

```
<223> OTHER INFORMATION: synthetic

<400> SEQUENCE: 5
atcaaaccta acagtggtgg caca                                          24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Lys Pro Asn Ser Gly Gly Thr
1               5

<210> SEQ ID NO 7
<211> LENGTH: 51
<212> TYPE: DNA
<213> ORGANISM: Artificial Sequence
<220> FEATURE:
<223> OTHER INFORMATION: synthetic

<400> SEQUENCE: 7
tcgagagggg gcccagtcat gaattactac tactactacg gtatggacgt c            51

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Ser Arg Gly Gly Pro Val Met Asn Tyr Tyr Tyr Tyr Tyr Gly Met Asp
1               5                   10                  15
Val

<210> SEQ ID NO 9
<211> LENGTH: 318
<212> TYPE: DNA
<213> ORGANISM: Artificial Sequence
<220> FEATURE:
<223> OTHER INFORMATION: synthetic

<400> SEQUENCE: 9
aacatccaga tgacccagtc tccatcctcc ctgtctgcat ctgtgggaga cagagtcacc   60
atcacttgcc gggcaagtca gagcattgac agttatttaa attggtatca gcagaaacca  120
ggtaaagccc ctaaactcct gatctatgtt gcatccagtt tgcaaagtgg gtcccatca   180 aggttcagtg gcagtggatc tgggaaagat ttcactctca ccatcagcag tctgcaacct  240
gaagattttg caacttacta ctgtcaacag agttacagta tccccacctt cggccaaggg  300
acacgactgg agattaaa                                                318

<210> SEQ ID NO 10
<211> LENGTH: 106
<212> TYPE: PRT
<213> ORGANISM: Artificial Sequence
<220> FEATURE:
<223> OTHER INFORMATION: synthetic

<400> SEQUENCE: 10

Asn Ile Gln Met Thr Gln Ser Pro Ser Ser Leu Ser Ala Ser Val Gly
```

```
            1               5                  10                 15
         Asp Arg Val Thr Ile Thr Cys Arg Ala Ser Gln Ser Ile Asp Ser Tyr
                        20                  25                 30

Leu Asn Trp Tyr Gln Gln Lys Pro Gly Lys Ala Pro Lys Leu Leu Ile
                        35                  40                 45

Tyr Val Ala Ser Ser Leu Gln Ser Gly Val Pro Ser Arg Phe Ser Gly
                        50                  55                 60

Ser Gly Ser Gly Lys Asp Phe Thr Leu Thr Ile Ser Ser Leu Gln Pro
         65                 70                  75                 80

Glu Asp Phe Ala Thr Tyr Tyr Cys Gln Gln Ser Tyr Ser Ile Pro Thr
                        85                  90                 95

Phe Gly Gln Gly Thr Arg Leu Glu Ile Lys
                        100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcattg acagttat                                                    18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Asp Ser Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gttgcatcc                                                               9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Val Ala Ser
1

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15

```
caacagagtt acagtatccc cacc                                          24
```

<210> SEQ ID NO 16
<211> LENGTH: 8
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Ile Pro Thr
1               5

<210> SEQ ID NO 17
<211> LENGTH: 369
<212> TYPE: DNA
<213> ORGANISM: Artificial Sequence
<220> FEATURE:
<223> OTHER INFORMATION: synthetic

<400> SEQUENCE: 17

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtac cataggctat   180
gcggactctg tgaagggccg attcaccatg tccagagaca cgccaagaa ctccctgtat    240 ctgcaaatga acagtctgag acctgaagac acggccttgt attattgtgc aaaagatatg   300
ggcgtatcac tggcactatg gggggctttt gatatctggg gccaagggac aatggtcacc   360
gtctcttca                                                          369
```

<210> SEQ ID NO 18
<211> LENGTH: 123
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Thr Ile Gly Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Met Gly Val Ser Leu Ala Leu Trp Gly Ala Phe Asp Ile
            100                 105                 110

Trp Gly Gln Gly Thr Met Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttgatgatta tgcc                                          24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Asp Asp Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagttgga atagtggtac cata                                          24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Ser Trp Asn Ser Gly Thr Ile
1               5

<210> SEQ ID NO 23
<211> LENGTH: 48
<212> TYPE: DNA
<213> ORGANISM: Artificial Sequence
<220> FEATURE:
<223> OTHER INFORMATION: synthetic

<400> SEQUENCE: 23
gcaaaagata tgggcgtatc actggcacta tgggggctt ttgatatc                 48

<210> SEQ ID NO 24
<211> LENGTH: 16
<212> TYPE: PRT
<213> ORGANISM: Artificial Sequence
<220> FEATURE:
<223> OTHER INFORMATION: synthetic

<400> SEQUENCE: 24

Ala Lys Asp Met Gly Val Ser Leu Ala Leu Trp Gly Ala Phe Asp Ile
1               5                   10                  15

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25

```
gacatccaga tgacccagtc tccatcctcc ctgtctgcat ctgtgggaga caaagtcacc      60
atcacttgcc gggcgagtca gaacattaga acctatttaa attggtatca gcagaaacca    120
gggaaagccc ctaaggtcct gatctctact gcatccagtt tgcaaagtgg ggtcccatca    180
aggttcagtg gcagtggatc tgggacagat ttcactctca ccatcagcag tctgcaacct    240
gaagattttg cagttttcta ctgtcaacag agtttcggta tccctcggac gttcggccaa    300
gggaccaagg tggaaatcaa a                                               321
```

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

```
Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Asn Ile Arg Thr Tyr
            20                  25                  30

Leu Asn Trp Tyr Gln Gln Lys Pro Gly Lys Ala Pro Lys Val Leu Ile
        35                  40                  45

Ser Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Phe Tyr Cys Gln Gln Ser Phe Gly Ile Pro Arg
                85                  90                  95

Thr Phe Gly Gln Gly Thr Lys Val Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27

```
cagaacatta gaacctat                                                   18
```

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

```
Gln Asn Ile Arg Thr Tyr
1               5
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 actgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Thr Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caacagagtt tcggtatccc tcggacg                                         27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Ser Phe Gly Ile Pro Arg Thr
1               5

<210> SEQ ID NO 33
<211> LENGTH: 366
<212> TYPE: DNA
<213> ORGANISM: Artificial Sequence
<220> FEATURE:
<223> OTHER INFORMATION: synthetic

<400> SEQUENCE: 33
caggtgcagc tggtggagtc tgggggaggc gtggtccagc ctggggaggtc cctgagactc      60 tcctgtgcag cgtctggatt caccttcagt acctatggca tgcactgggt ccgccaggct     120
ccaggcaagg ggctggagtg ggtggcactt atatggaatg atggaagtaa taaatactat     180
gcagactccg tgaagggccg attcaccatc tccagagaca attccaagaa cacgctggat     240
ctgcaaatga acagcctgag agccgaggac acggctgtgt attactgtgc gaggctgaat     300
actcgtataa ctggaactac gaatcttgac tactggggcc agggaaccct ggtcaccgtc     360
tcctca                                                              366

<210> SEQ ID NO 34
<211> LENGTH: 122
<212> TYPE: PRT
<213> ORGANISM: Artificial Sequence
<220> FEATURE:
<223> OTHER INFORMATION: synthetic

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

```
Gly Met His Trp Val Arg Gln Ala Pro Gly Lys Gly Leu Glu Trp Val
        35                  40                  45

Ala Leu Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Leu Asn Thr Arg Ile Thr Gly Thr Thr Asn Leu Asp Tyr Trp
                100                 105                 110

Gly Gln Gly Thr Leu Val Thr Val Ser Ser
        115                 120
```

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcacct tcagtaccta tggc                                        24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Thr Tyr Gly
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatggaatg atggaagtaa taaa                                        24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Trp Asn Asp Gly Ser Asn Lys
1               5

<210> SEQ ID NO 39
<211> LENGTH: 45
<212> TYPE: DNA
<213> ORGANISM: Artificial Sequence
<220> FEATURE:
<223> OTHER INFORMATION: synthetic

<400> SEQUENCE: 39
gcgaggctga atactcgtat aactggaact acgaatcttg actac         45

<210> SEQ ID NO 40
<211> LENGTH: 15
<212> TYPE: PRT
<213> ORGANISM: Artificial Sequence
<220> FEATURE:
<223> OTHER INFORMATION: synthetic

<400> SEQUENCE: 40

Ala Arg Leu Asn Thr Arg Ile Thr Gly Thr Thr Asn Leu Asp Tyr
1               5                   10                  15

<210> SEQ ID NO 41
<211> LENGTH: 324
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctcc ctgtctgcat ctgtaggaga cagagtcacc     60
gtctcttgcc gggcaagtca gagcattgcc aactacttaa attggtatca gcagaaacca    120
gggaaagccc ctaacctcct gatctatggt gcatacactt tgcaaagtgg ggtcccatca    180
aggttccgtg gcagtggatc tgggacagat ttcactctca ccatcagcag tctgcaacct    240
gaagattttg cgacttacta ctgtcaacag acttacagta ccccctccgat caccttcggc   300 caagggacac gactggagat taaa                                           324

<210> SEQ ID NO 42
<211> LENGTH: 108
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Val Ser Cys Arg Ala Ser Gln Ser Ile Ala Asn Tyr
                20                  25                  30

Leu Asn Trp Tyr Gln Gln Lys Pro Gly Lys Ala Pro Asn Leu Leu Ile
            35                  40                  45

Tyr Gly Ala Tyr Thr Leu Gln Ser Gly Val Pro Ser Arg Phe Arg Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Pro
                85                  90                  95

Ile Thr Phe Gly Gln Gly Thr Arg Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
cagagcattg ccaactac                                                   18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Ser Ile Ala Asn Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 ggtgcatac                                                                  9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Gly Ala Tyr
1

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
caacagactt acagtacccc tccgatcacc                                          30

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Gln Gln Thr Tyr Ser Thr Pro Pro Ile Thr
1               5                   10

<210> SEQ ID NO 49
<211> LENGTH: 369
<212> TYPE: DNA
<213> ORGANISM: Artificial Sequence
<220> FEATURE:
<223> OTHER INFORMATION: synthetic

<400> SEQUENCE: 49
cagctgcagc tgcgtgagtc gggcccagga ctggtgaagc cttcggagac cctgtccctc         60
acctgtactg tctctggtgg ctccatcaac gacaattctt ttttctggga ctggatccgc        120
cagaccccag ggaggggact ggagtggatt gggaatatct tttttgatgg gaacacttac        180

-continued

```
tatacccgt ccctcaagag tcgagtcatc atatccgttg acatgtccca gaaccaattc    240
tccctgaggc tgacctctgt gaccgccgca gacacggctc tgtattactg tgcgagacat    300
aagaggtcca tgacagcttg ggggttcttt gactattggg gccagggaac cctggtcacc    360
gtctcctca                                                           369
```

```
<210> SEQ ID NO 50
<211> LENGTH: 123
<212> TYPE: PRT
<213> ORGANISM: Artificial Sequence
<220> FEATURE:
<223> OTHER INFORMATION: synthetic

<400> SEQUENCE: 50
```

Gln Leu Gln Leu Arg Glu Ser Gly Pro Gly Leu Val Lys Pro Ser Glu
1               5                   10                  15

Thr Leu Ser Leu Thr Cys Thr Val Ser Gly Gly Ser Ile Asn Asp Asn
            20                  25                  30

Ser Phe Phe Trp Asp Trp Ile Arg Gln Thr Pro Gly Arg Gly Leu Glu
        35                  40                  45

Trp Ile Gly Asn Ile Phe Phe Asp Gly Asn Thr Tyr Tyr Thr Pro Ser
    50                  55                  60

Leu Lys Ser Arg Val Ile Ile Ser Val Asp Met Ser Gln Asn Gln Phe
65                  70                  75                  80

Ser Leu Arg Leu Thr Ser Val Thr Ala Ala Asp Thr Ala Leu Tyr Tyr
                85                  90                  95

Cys Ala Arg His Lys Arg Ser Met Thr Ala Trp Gly Phe Phe Asp Tyr
            100                 105                 110

Trp Gly Gln Gly Thr Leu Val Thr Val Ser Ser
        115                 120

```
<210> SEQ ID NO 51
<211> LENGTH: 30
<212> TYPE: DNA
<213> ORGANISM: Artificial Sequence
<220> FEATURE:
<223> OTHER INFORMATION: synthetic

<400> SEQUENCE: 51
ggtggctcca tcaacgacaa ttcttttttc                                     30

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52
```

Gly Gly Ser Ile Asn Asp Asn Ser Phe Phe
1               5                   10

```
<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
atcttttttg atgggaacac t                                              21
```

```
<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Ile Phe Phe Asp Gly Asn Thr
1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcgagacata agaggtccat gacagcttgg gggttctttg actat            45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Arg His Lys Arg Ser Met Thr Ala Trp Gly Phe Phe Asp Tyr
1               5                   10                  15

<210> SEQ ID NO 57
<211> LENGTH: 324
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcctcc ctgtctgcat ctgttggtga cagagtcacc      60
atcacttgcc gggcaagtaa gagaattaac acctatttga attggtatca gcagaaacca     120
ggtaaagccc ctaaagttct gatctattct gcatccaatt tgcaaagtgg ggtcccctca     180
cggttcagtg gcagtggatc tgggacagat ttcactctca ccatcaacag tctgcaacct     240
gaagattttg caacttactt ctgtcaacag agtttcagtg cccctccgat caccttcggc     300
caagggacac gactggagat taaa                                            324

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Arg Ile Asn Thr Tyr
            20                  25                  30

Leu Asn Trp Tyr Gln Gln Lys Pro Gly Lys Ala Pro Lys Val Leu Ile
        35                  40                  45
```

```
Tyr Ser Ala Ser Asn Leu Gln Ser Gly Val Pro Ser Arg Phe Ser Gly
            50                  55                  60

Ser Gly Ser Gly Thr Asp Phe Thr Leu Thr Ile Asn Ser Leu Gln Pro
 65                  70                  75                  80

Glu Asp Phe Ala Thr Tyr Phe Cys Gln Gln Ser Phe Ser Ala Pro Pro
                 85                  90                  95

Ile Thr Phe Gly Gln Gly Thr Arg Leu Glu Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
aagagaatta acacctat                                              18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

```
Lys Arg Ile Asn Thr Tyr
 1               5
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 tctgcatcc                                                         9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

```
Ser Ala Ser
 1
```

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
caacagagtt tcagtgcccc tccgatcacc                                 30

<210> SEQ ID NO 64
<211> LENGTH: 10
<212> TYPE: PRT

```
<213> ORGANISM: Artificial Sequence
<220> FEATURE:
<223> OTHER INFORMATION: synthetic

<400> SEQUENCE: 64

Gln Gln Ser Phe Ser Ala Pro Pro Ile Thr
1               5                   10

<210> SEQ ID NO 65
<211> LENGTH: 366
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtaaagc ctgggggggtc cctgagactc      60 tcctgtgttg tctctggatt cactttcaga atctatacca tgaattgggt ccgccaggct     120
ccagggaagg gactggagtg gtcgcatcc attagtagta gtagtagttt cattaattat      180
gcagactcat tgaagggccg attcaccatc tccagagaca acgcccagaa ctcactgtat     240
ctacaaatga acagcctgag agccgaggac acggctattt attactgtgc gagagcggcg     300
ggtaacgatg ttttgcctgg tcgtatggac gtctggggcc aagggacctc ggtcaccgtc     360
tcctca                                                                366

<210> SEQ ID NO 66
<211> LENGTH: 122
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Val Val Ser Gly Phe Thr Phe Arg Ile Tyr
            20                  25                  30

Thr Met Asn Trp Val Arg Gln Ala Pro Gly Lys Gly Leu Glu Trp Val
        35                  40                  45

Ala Ser Ile Ser Ser Ser Ser Phe Ile Asn Tyr Ala Asp Ser Leu
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Ala Ala Gly Asn Asp Val Leu Pro Gly Arg Met Asp Val Trp
            100                 105                 110

Gly Gln Gly Thr Ser Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcactt tcagaatcta tacc                                              24
```

```
<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Arg Ile Tyr Thr
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attagtagta gtagtagttt catt                                          24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Ser Ser Ser Ser Ser Phe Ile
1               5

<210> SEQ ID NO 71
<211> LENGTH: 45
<212> TYPE: DNA
<213> ORGANISM: Artificial Sequence
<220> FEATURE:
<223> OTHER INFORMATION: synthetic

<400> SEQUENCE: 71
gcgagagcgg cgggtaacga tgttttgcct ggtcgtatgg acgtc                   45

<210> SEQ ID NO 72
<211> LENGTH: 15
<212> TYPE: PRT
<213> ORGANISM: Artificial Sequence
<220> FEATURE:
<223> OTHER INFORMATION: synthetic

<400> SEQUENCE: 72

Ala Arg Ala Ala Gly Asn Asp Val Leu Pro Gly Arg Met Asp Val
1               5                   10                  15

<210> SEQ ID NO 73
<211> LENGTH: 324
<212> TYPE: DNA
<213> ORGANISM: Artificial Sequence
<220> FEATURE:
<223> OTHER INFORMATION: synthetic

<400> SEQUENCE: 73
gaaattgtgt tgacgcagtc tccaggcacc ctgtctttgt ctccagggga aagagccacc   60
ctctcctgca gggccagtca gagtgttagc agcaactact tagcgtggta ccagcagaaa  120
cctggccagg ttcccagtct cctcatctat ggtgcatcca gcagggccac tggcatccca  180
```
gacaggttca gtggcagcgg gtctgggaca gacttcactc tcaccatcac cagactggag    240
cctgaagatt ttgcagtgta ttactgtcag cagtatggta tctcaccttg gacgttcggc    300
caagggacca aggtggaaat caaa                                           324

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Val Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Gly Ile Ser Pro
                85                  90                  95

Trp Thr Phe Gly Gln Gly Thr Lys Val Glu Ile Lys
            100                 105

<210> SEQ ID NO 75
<211> LENGTH: 21
<212> TYPE: DNA
<213> ORGANISM: Artificial Sequence
<220> FEATURE:
<223> OTHER INFORMATION: synthetic

<400> SEQUENCE: 75
cagagtgtta gcagcaacta c                                              21

<210> SEQ ID NO 76
<211> LENGTH: 7
<212> TYPE: PRT
<213> ORGANISM: Artificial Sequence
<220> FEATURE:
<223> OTHER INFORMATION: synthetic

<400> SEQUENCE: 76

Gln Ser Val Ser Ser Asn Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 ggtgcatcc                                                             9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Gly Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
cagcagtatg gtatctcacc ttggacg        27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Tyr Gly Ile Ser Pro Trp Thr
1               5

<210> SEQ ID NO 81
<211> LENGTH: 372
<212> TYPE: DNA
<213> ORGANISM: Artificial Sequence
<220> FEATURE:
<223> OTHER INFORMATION: synthetic

<400> SEQUENCE: 81
caggtgcagc tggtgcagtc tggggctgag gtgaagaagc ctggggcctc agtgaaggtc        60
tcctgcaagg cttctggata caccttcacc ggctactata tacactgggt gcgacaggcc       120
cctggacaag gacttgagtg gatgggatgg atcaacccta acagtattgg cacaaactat       180
gcacagaagt ttcagggcag ggtcaccttg accaggggaca cgtccatcag tacagcctac       240
atggagctga gcagtctgag atctgacgac acggccgtgt attactgtgc gagagggggt       300
agcagctcat attactacta ctactacggt atggacgtct ggggccaagg gaccacggtc       360
accgtctcct ca                                                            372

<210> SEQ ID NO 82
<211> LENGTH: 124
<212> TYPE: PRT
<213> ORGANISM: Artificial Sequence
<220> FEATURE:
<223> OTHER INFORMATION: synthetic

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Ile Gly Thr Asn Tyr Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Ser Ser Tyr Tyr Tyr Tyr Tyr Tyr Gly Met Asp
            100                 105                 110

Val Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ggatacacct tcaccggcta ctat                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Tyr Thr Phe Thr Gly Tyr Tyr
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85 atcaaccta acagtattgg caca                                           24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86

Ile Asn Pro Asn Ser Ile Gly Thr
1               5

<210> SEQ ID NO 87
<211> LENGTH: 51
<212> TYPE: DNA
<213> ORGANISM: Artificial Sequence
<220> FEATURE:
<223> OTHER INFORMATION: synthetic

<400> SEQUENCE: 87
gcgagagggg gtagcagctc atattactac tactactacg gtatggacgt c            51

<210> SEQ ID NO 88
<211> LENGTH: 17
<212> TYPE: PRT
<213> ORGANISM: Artificial Sequence

```
<220> FEATURE:
<223> OTHER INFORMATION: synthetic

<400> SEQUENCE: 88

Ala Arg Gly Gly Ser Ser Tyr Tyr Tyr Tyr Tyr Gly Met Asp
1               5                   10                  15
Val

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcctcc ctgtctgcat ctgtaggaga cagagtcacc    60
atcacttgcc gggcaagtca gagcattgac aactatttaa attggtatca gcagaaacca   120
gggaaagccc ctaagctcct gatctatgtt gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac tttcggcgga   300
gggaccaagg tggagatcaa a                                             321

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagcattg acaactat                                                 18

<210> SEQ ID NO 92
<211> LENGTH: 6
<212> TYPE: PRT
```

```
<213> ORGANISM: Artificial Sequence
<220> FEATURE:
<223> OTHER INFORMATION: synthetic

<400> SEQUENCE: 92

Gln Ser Ile Asp Asn Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gttgcatcc                                                                 9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Val Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caacagagtt acagtacccc gctcact                                            27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Ser Tyr Ser Thr Pro Leu Thr
1               5

<210> SEQ ID NO 97
<211> LENGTH: 372
<212> TYPE: DNA
<213> ORGANISM: Artificial Sequence
<220> FEATURE:
<223> OTHER INFORMATION: synthetic

<400> SEQUENCE: 97
caggtgcagc tggtgcagtc tggggctgag gtgatgaagc ctggggcctc agtgaaggtc         60
tcctgcaagg cttctggata caccttcacc ggctactata ttcattgggt acgacaggcc        120
cctggacaag gcttgagtg gatgggatgg atcaccccta acagtggcgc cacaaactat        180
gcacagaagt tcagggcag ggtcaccctg accagggaca cgtccatcag cacagcctac        240
atggaactga ccaggctgaa atctgacgac acggccgttt attattgtgc gagaggggt        300
```

```
cagttggagt tcttctatta ctactacggt atggacgtct ggggccaagg gaccacggtc    360
accgtctcct ca                                                        372
```

<210> SEQ ID NO 98
<211> LENGTH: 124
<212> TYPE: PRT
<213> ORGANISM: Artificial Sequence
<220> FEATURE:
<223> OTHER INFORMATION: synthetic

<400> SEQUENCE: 98

```
Gln Val Gln Leu Val Gln Ser Gly Ala Glu Val Met Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Thr Pro Asn Ser Gly Ala Thr Asn Tyr Ala Gln Lys Phe
    50                  55                  60

Gln Gly Arg Val Thr Leu Thr Arg Asp Thr Ser Ile Ser Thr Ala Tyr
65                  70                  75                  80

Met Glu Leu Thr Arg Leu Lys Ser Asp Asp Thr Ala Val Tyr Tyr Cys
                85                  90                  95

Ala Arg Gly Gly Gln Leu Glu Phe Phe Tyr Tyr Tyr Gly Met Asp
            100                 105                 110

Val Trp Gly Gln Gly Thr Thr Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggatacacct tcaccggcta ctat                                           24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Tyr Thr Phe Thr Gly Tyr Tyr
1               5
```

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101

```
atcacccta acagtggcgc aca                                             24
```

<210> SEQ ID NO 102
<211> LENGTH: 8
<212> TYPE: PRT

```
<213> ORGANISM: Artificial Sequence
<220> FEATURE:
<223> OTHER INFORMATION: synthetic

<400> SEQUENCE: 102

Ile Thr Pro Asn Ser Gly Ala Thr
1               5

<210> SEQ ID NO 103
<211> LENGTH: 51
<212> TYPE: DNA
<213> ORGANISM: Artificial Sequence
<220> FEATURE:
<223> OTHER INFORMATION: synthetic

<400> SEQUENCE: 103
gcgagagggg gtcagttgga gttcttctat tactactacg gtatggacgt c            51

<210> SEQ ID NO 104
<211> LENGTH: 17
<212> TYPE: PRT
<213> ORGANISM: Artificial Sequence
<220> FEATURE:
<223> OTHER INFORMATION: synthetic

<400> SEQUENCE: 104

Ala Arg Gly Gly Gln Leu Glu Phe Phe Tyr Tyr Tyr Tyr Gly Met Asp
1               5                   10                  15

Val

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccatcctcc ctctctgcat ctgcaggaga cagagtcacc     60
atcacttgcc gggcaagtca gagcattgac agctatttaa attggtatca gcagaaacca    120
gggaaagccc ctaaactcct gatctctgct acatccggtt tccaaagtgg ggtcccatca    180
aggttcagtg gcagtggatc tgggacagat ttcactctca ccatcagcag tctgcaacct    240
gaagattttg aacttactac tgtcaacag agttacacta ccctatcac cttcggccaa     300 gggacacgac tggagattaa a                                              321

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ser Ile Asp Ser Tyr
            20                  25                  30

Leu Asn Trp Tyr Gln Gln Lys Pro Gly Lys Ala Pro Lys Leu Leu Ile
        35                  40                  45

Ser Ala Thr Ser Gly Phe Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ser Tyr Thr Thr Pro Ile
                85                  90                  95

Thr Phe Gly Gln Gly Thr Arg Leu Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagcattg acagctat                                              18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Ile Asp Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctacatcc                                                         9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Thr Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacagagtt acactacccc tatcacc                                    27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Ser Tyr Thr Thr Pro Ile Thr
1               5

<210> SEQ ID NO 113
<211> LENGTH: 372
<212> TYPE: DNA
<213> ORGANISM: Artificial Sequence
<220> FEATURE:
<223> OTHER INFORMATION: synthetic

<400> SEQUENCE: 113

```
caggtgcagc tggtgcagtc tggggctgag gtgaaggagc ctggggcctc agtgaaggtc    60
tcctgtaagg cttctggata caccttcacc gactactata tacactgggt gcgacaggcc   120
cctggacaag gcttgagtg atgggatgg atcaatctta acagtggtgg caaaaaccat   180
gcacagaagt tcagggcag gtcaccgtg accagtgaca cgtccatcaa cacagcctat   240
atcgaactgg gcaggctgag aggtgacgac acggccgtgt attactgttc gagaggggggt   300
ggaagtcact actattatta ttatcacggt atggacgtct ggggccaagg aaccacggtc   360
accgtctcct ca                                                      372
```

<210> SEQ ID NO 114
<211> LENGTH: 124
<212> TYPE: PRT
<213> ORGANISM: Artificial Sequence
<220> FEATURE:
<223> OTHER INFORMATION: synthetic

<400> SEQUENCE: 114

Gln Val Gln Leu Val Gln Ser Gly Ala Glu Val Lys Glu Pro Gly Ala
1               5                   10                  15
Ser Val Lys Val Ser Cys Lys Ala Ser Gly Tyr Thr Phe Thr Asp Tyr
            20                  25                  30
Tyr Ile His Trp Val Arg Gln Ala Pro Gly Gln Gly Leu Glu Trp Met
        35                  40                  45
Gly Trp Ile Asn Leu Asn Ser Gly Gly Lys Asn His Ala Gln Lys Phe
    50                  55                  60
Gln Gly Arg Val Thr Val Thr Ser Asp Thr Ser Ile Asn Thr Ala Tyr
65                  70                  75                  80
Ile Glu Leu Gly Arg Leu Arg Gly Asp Asp Thr Ala Val Tyr Tyr Cys
                85                  90                  95
Ser Arg Gly Gly Gly Ser His Tyr Tyr Tyr Tyr His Gly Met Asp
            100                 105                 110
Val Trp Gly Gln Gly Thr Thr Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggatacacct tcaccgacta ctat                                          24

<210> SEQ ID NO 116
<211> LENGTH: 8

```
<212> TYPE: PRT
<213> ORGANISM: Artificial Sequence
<220> FEATURE:
<223> OTHER INFORMATION: synthetic

<400> SEQUENCE: 116

Gly Tyr Thr Phe Thr Asp Tyr Tyr
1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atcaatctta acagtggtgg caaa                                           24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Asn Leu Asn Ser Gly Gly Lys
1               5

<210> SEQ ID NO 119
<211> LENGTH: 51
<212> TYPE: DNA
<213> ORGANISM: Artificial Sequence
<220> FEATURE:
<223> OTHER INFORMATION: synthetic

<400> SEQUENCE: 119
tcgagagggg gtggaagtca ctactattat tattatcacg gtatggacgt c            51

<210> SEQ ID NO 120
<211> LENGTH: 17
<212> TYPE: PRT
<213> ORGANISM: Artificial Sequence
<220> FEATURE:
<223> OTHER INFORMATION: synthetic

<400> SEQUENCE: 120

Ser Arg Gly Gly Gly Ser His Tyr Tyr Tyr Tyr Tyr His Gly Met Asp
1               5                   10                  15

Val

<210> SEQ ID NO 121
<211> LENGTH: 321
<212> TYPE: DNA
<213> ORGANISM: Artificial Sequence
<220> FEATURE:
<223> OTHER INFORMATION: synthetic

<400> SEQUENCE: 121
gacatccaga tgacccagtc tccatcctcc ctgtctgcat ctgtaggaga cagaatcacc    60
atcacttgcc gggcaagtca gcagcattgac agctatttaa attggtatca gcagaaacca   120
gggaaagccc ctaaactcct gatctatcct gcatccactt tgcaaagtgg ggtcccatca   180
aggttcagtg gcagtggatc tgggacagat ttcactctca ccatcagcag tctgcaacct   240
```

```
gaagattctg caatttacta ctgtcaacag agttacagta ccccgctcac tttcggcgga    300
gggaccaagg tggagatcaa a                                              321
```

<210> SEQ ID NO 122
<211> LENGTH: 107
<212> TYPE: PRT
<213> ORGANISM: Artificial Sequence
<220> FEATURE:
<223> OTHER INFORMATION: synthetic

<400> SEQUENCE: 122

```
Asp Ile Gln Met Thr Gln Ser Pro Ser Ser Leu Ser Ala Ser Val Gly
1               5                   10                  15

Asp Arg Ile Thr Ile Thr Cys Arg Ala Ser His Ser Ile Asp Ser Tyr
            20                  25                  30

Leu Asn Trp Tyr Gln Gln Lys Pro Gly Lys Ala Pro Lys Leu Leu Ile
        35                  40                  45

Tyr Pro Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Ile Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123

```
cacagcattg acagctat                                                  18
```

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

```
His Ser Ile Asp Ser Tyr
1               5
```

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125

```
cctgcatcc                                                             9
```

<210> SEQ ID NO 126
<211> LENGTH: 3
<212> TYPE: PRT
<213> ORGANISM: Artificial Sequence
<220> FEATURE:

```
<223> OTHER INFORMATION: synthetic

<400> SEQUENCE: 126

Pro Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
caacagagtt acagtacccc gctcact                                           27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Ser Tyr Ser Thr Pro Leu Thr
1               5

<210> SEQ ID NO 129
<211> LENGTH: 372
<212> TYPE: DNA
<213> ORGANISM: Artificial Sequence
<220> FEATURE:
<223> OTHER INFORMATION: synthetic

<400> SEQUENCE: 129
caggtgcagc tggtggagtc tgggggaggc gtggtccagc ctgggaggtc cctgagactc        60
tcctgtgtag cgtctggatt caccttcagt agctatggca tgtctgggt ccgccagact       120 ccaggcaagg ggctggagtg ggtggcagtt atatggcatg atggaactaa taattactat       180
gcagactccg tgaagggccg attcaccatc tccagagaca attccaagaa cacgctgtat       240
ctgcaaatga acagcctgag agccgaggac acggctgtgt attactgtgc gagagaacca       300
tggctggtac ggggctacta ctactacgct atggacgtct ggggccaagg gaccacggtc       360
accgtctcct ca                                                          372

<210> SEQ ID NO 130
<211> LENGTH: 124
<212> TYPE: PRT
<213> ORGANISM: Artificial Sequence
<220> FEATURE:
<223> OTHER INFORMATION: synthetic

<400> SEQUENCE: 130

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met Val Trp Val Arg Gln Thr Pro Gly Lys Gly Leu Glu Trp Val
        35                  40                  45

Ala Val Ile Trp His Asp Gly Thr Asn Asn Tyr Tyr Ala Asp Ser Val
    50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                85                  90                  95
Ala Arg Glu Pro Trp Leu Val Arg Gly Tyr Tyr Tyr Ala Met Asp
            100                 105                 110
Val Trp Gly Gln Gly Thr Thr Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggattcacct tcagtagcta tggc                                          24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Phe Thr Phe Ser Ser Tyr Gly
1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
atatggcatg atggaactaa taat                                          24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Trp His Asp Gly Thr Asn Asn
1               5

<210> SEQ ID NO 135
<211> LENGTH: 51
<212> TYPE: DNA
<213> ORGANISM: Artificial Sequence
<220> FEATURE:
<223> OTHER INFORMATION: synthetic

<400> SEQUENCE: 135
gcgagagaac catggctggt acggggctac tactactacg ctatggacgt c            51

<210> SEQ ID NO 136
<211> LENGTH: 17
<212> TYPE: PRT
<213> ORGANISM: Artificial Sequence
<220> FEATURE:

<223> OTHER INFORMATION: synthetic

<400> SEQUENCE: 136

Ala Arg Glu Pro Trp Leu Val Arg Gly Tyr Tyr Tyr Tyr Ala Met Asp
1               5                   10                  15

Val

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccttccacc ctgtctgcat ctgtaggaga cagagtcacc    60
atcacttgcc gggccagtca gagtattagt agttggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa a                                             321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
cagagtatta gtagttgg                                                  18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Ile Ser Ser Trp
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 aaggcgtct                                                              9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Lys Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagtata atagttattc tcggacg                                         27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Tyr Asn Ser Tyr Ser Arg Thr
1               5

<210> SEQ ID NO 145
<211> LENGTH: 369
<212> TYPE: DNA
<213> ORGANISM: Artificial Sequence
<220> FEATURE:
<223> OTHER INFORMATION: synthetic

<400> SEQUENCE: 145
cagctgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaagggact ggagtggatt gggagtatct attatagtgg agcccctac     180 tacatcccgt ccctcaagag tcgagtcacc atatccgtag acacgtccaa gaaccagttc    240
tccctgaagc tgagctctgt gaccgccgca gacacggcta tgtattactg tgcgagacag    300
gggcggggca tagccagggc tggtcccttt gactactggg gccagggaac cctggtcacc    360
gtctcctca                                                          369

<210> SEQ ID NO 146
<211> LENGTH: 123
<212> TYPE: PRT
<213> ORGANISM: Artificial Sequence
<220> FEATURE:
<223> OTHER INFORMATION: synthetic

<400> SEQUENCE: 146

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Pro Tyr Tyr Ile Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg Gln Gly Arg Gly Ile Ala Arg Ala Gly Pro Phe Asp Tyr
            100                 105                 110

Trp Gly Gln Gly Thr Leu Val Thr Val Ser Ser
        115                 120

<210> SEQ ID NO 147
<211> LENGTH: 30
<212> TYPE: DNA
<213> ORGANISM: Artificial Sequence
<220> FEATURE:
<223> OTHER INFORMATION: synthetic

<400> SEQUENCE: 147
ggtggctcca tcagcagtag tagttactac                                    30

<210> SEQ ID NO 148
<211> LENGTH: 10
<212> TYPE: PRT
<213> ORGANISM: Artificial Sequence
<220> FEATURE:
<223> OTHER INFORMATION: synthetic

<400> SEQUENCE: 148

Gly Gly Ser Ile Ser Ser Ser Ser Tyr Tyr
1               5                   10

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149
atctattata gtgggagccc c                                             21

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Tyr Tyr Ser Gly Ser Pro
1               5

<210> SEQ ID NO 151
<211> LENGTH: 45
<212> TYPE: DNA
<213> ORGANISM: Artificial Sequence
<220> FEATURE:
<223> OTHER INFORMATION: synthetic

<400> SEQUENCE: 151
gcgagacagg ggcggggcat agccagggct ggtcccttg actac          45

<210> SEQ ID NO 152
<211> LENGTH: 15
<212> TYPE: PRT
<213> ORGANISM: Artificial Sequence
<220> FEATURE:
<223> OTHER INFORMATION: synthetic

<400> SEQUENCE: 152

Ala Arg Gln Gly Arg Gly Ile Ala Arg Ala Gly Pro Phe Asp Tyr
1               5                   10                  15

<210> SEQ ID NO 153
<211> LENGTH: 324
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcctcc ctgtctgcat ctgtaggaga cagagtcacc     60
atcacttgcc gggcgagtca gggcattagc aattatttag cctggtatca ggagaaacca    120
gggaaagttc ctaaactcct gatctatgct gcatccactt tgcaatcagg ggtcccatct    180
cggttcagtg gcagtggatc tgggacagat ttcactctca ccatcaccag cctgcagtct    240
gaagatgttg caacttatta ctgtcaaaag tataacagtg cccctccgtg acgttcggc     300 caagggacca aggtggaaat caaa                                           324

<210> SEQ ID NO 154
<211> LENGTH: 108
<212> TYPE: PRT
<213> ORGANISM: Artificial Sequence
<220> FEATURE:
<223> OTHER INFORMATION: synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Glu Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Thr Ser Leu Gln Ser
65                  70                  75                  80

Glu Asp Val Ala Thr Tyr Tyr Cys Gln Lys Tyr Asn Ser Ala Pro Pro
            85                  90                  95

Trp Thr Phe Gly Gln Gly Thr Lys Val Glu Ile Lys
        100                 105

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggcatta gcaattat                                                     18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Ser Asn Tyr
1               5

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcatcc                                                                9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ser
1

<210> SEQ ID NO 159
<211> LENGTH: 30
<212> TYPE: DNA
<213> ORGANISM: Artificial Sequence
<220> FEATURE:
<223> OTHER INFORMATION: synthetic

<400> SEQUENCE: 159
caaaagtata acagtgcccc tccgtggacg                                        30

<210> SEQ ID NO 160
<211> LENGTH: 10
<212> TYPE: PRT
<213> ORGANISM: Artificial Sequence
<220> FEATURE:
<223> OTHER INFORMATION: synthetic

<400> SEQUENCE: 160

Gln Lys Tyr Asn Ser Ala Pro Pro Trp Thr
1               5                   10

<210> SEQ ID NO 161
<211> LENGTH: 357
<212> TYPE: DNA
<213> ORGANISM: Artificial Sequence
<220> FEATURE:
<223> OTHER INFORMATION: synthetic

<400> SEQUENCE: 161
gaggtgcagc tggtggagtc tgggggaggt gtggtacggc ctgggggtc cctcagactc      60 tcctgtgcag cctctggatt caacgttgat gattatggca tgagctgggt ccgccaaatt    120
ccagggaagg ggctggagtg gatctctggt attaattgga atggtggtag gatatattat    180
gctgactcta tgaagggccg aatcaccatc tccagagaca acgccaagaa ctccctatat    240
ctacaaatga acagtctgag agccgaggac acggccttat atcactgtgt gagagatcag    300
tggctggtac gaggacttga ctactggggc cagggaaccc tggtcaccgt ctcctca      357

<210> SEQ ID NO 162
<211> LENGTH: 119
<212> TYPE: PRT
<213> ORGANISM: Artificial Sequence
<220> FEATURE:
<223> OTHER INFORMATION: synthetic

<400> SEQUENCE: 162

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Asn Val Asp Asp Tyr
            20                  25                  30

Gly Met Ser Trp Val Arg Gln Ile Pro Gly Lys Gly Leu Glu Trp Ile
        35                  40                  45

Ser Gly Ile Asn Trp Asn Gly Gly Arg Ile Tyr Tyr Ala Asp Ser Met
    50                  55                  60

Lys Gly Arg Ile Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Val Arg Asp Gln Trp Leu Val Arg Gly Leu Asp Tyr Trp Gly Gln Gly
            100                 105                 110

Thr Leu Val Thr Val Ser Ser
        115

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggattcaacg ttgatgatta tggc      24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Asn Val Asp Asp Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
attaattgga atggtggtag gata                                          24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Asn Trp Asn Gly Gly Arg Ile
1               5

<210> SEQ ID NO 167
<211> LENGTH: 36
<212> TYPE: DNA
<213> ORGANISM: Artificial Sequence
<220> FEATURE:
<223> OTHER INFORMATION: synthetic

<400> SEQUENCE: 167
gtgagagatc agtggctggt acgaggactt gactac                             36

<210> SEQ ID NO 168
<211> LENGTH: 12
<212> TYPE: PRT
<213> ORGANISM: Artificial Sequence
<220> FEATURE:
<223> OTHER INFORMATION: synthetic

<400> SEQUENCE: 168

Val Arg Asp Gln Trp Leu Val Arg Gly Leu Asp Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcctca ctgtctgcat ctgtaggaga cagagtcacc    60
atcacttgtc gggcgagtca gggcatttac aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccaacaa tataatactt acccgtacac ttttggccag   300
gggaccaagc tggagatcaa a                                            321

<210> SEQ ID NO 170

```
<211> LENGTH: 107
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Tyr
                85                  90                  95

Thr Phe Gly Gln Gly Thr Lys Leu Glu Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagggcattt acaattat                                                    18

<210> SEQ ID NO 172
<211> LENGTH: 6
<212> TYPE: PRT
<213> ORGANISM: Artificial Sequence
<220> FEATURE:
<223> OTHER INFORMATION: synthetic

<400> SEQUENCE: 172

Gln Gly Ile Tyr Asn Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gctgcatcc                                                               9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
1
```

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
caacaatata atacttaccc gtacact                                               27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Tyr Asn Thr Tyr Pro Tyr Thr
1               5

<210> SEQ ID NO 177
<211> LENGTH: 384
<212> TYPE: DNA
<213> ORGANISM: Artificial Sequence
<220> FEATURE:
<223> OTHER INFORMATION: synthetic

<400> SEQUENCE: 177
caggtgcagc tggtggagtc tgggggaggc ttggtcaagc ctggagggtc cctgagactc            60
tcctgtgcag cctctggatt caccttcagt gactaccacc tgagctggat ccgccaggct           120
ccagggaagg gctggagtg gtttcttac attagaagta gtggtaggac catagactac             180
gcagcctctg tgaagggccg attcaccatc tccaggaca acgccaagaa ttcactgtat            240
ctgcaaatga acagcctgag agtcgaggat acggccgtgt attactgtgc gagagagaac           300
tggattgtgc taaaggtata tgctggtata gtgggagccc tcttgacca atggggtcag            360 ggaaccctgg tcaccgtctc ctca                                                 384

<210> SEQ ID NO 178
<211> LENGTH: 128
<212> TYPE: PRT
<213> ORGANISM: Artificial Sequence
<220> FEATURE:
<223> OTHER INFORMATION: synthetic

<400> SEQUENCE: 178

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

His Leu Ser Trp Ile Arg Gln Ala Pro Gly Lys Gly Leu Glu Trp Val
        35                  40                  45

Ser Tyr Ile Arg Ser Ser Gly Arg Thr Ile Asp Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Arg Glu Asn Trp Ile Val Leu Lys Val Tyr Ala Gly Ile Val Gly
            100                 105                 110

Ala Pro Leu Asp Gln Trp Gly Gln Gly Thr Leu Val Thr Val Ser Ser
        115                 120                 125

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
ggattcacct tcagtgacta ccac                                              24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Asp Tyr His
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
attagaagta gtggtaggac cata                                              24

<210> SEQ ID NO 182
<211> LENGTH: 8
<212> TYPE: PRT
<213> ORGANISM: Artificial Sequence
<220> FEATURE:
<223> OTHER INFORMATION: synthetic

<400> SEQUENCE: 182

Ile Arg Ser Ser Gly Arg Thr Ile
1               5

<210> SEQ ID NO 183
<211> LENGTH: 63
<212> TYPE: DNA
<213> ORGANISM: Artificial Sequence
<220> FEATURE:
<223> OTHER INFORMATION: synthetic

<400> SEQUENCE: 183
gcgagagaga actgattgt gctaaaggta tatgctggta tagtgggagc ccctcttgac         60
caa                                                                     63

<210> SEQ ID NO 184
<211> LENGTH: 21
<212> TYPE: PRT
<213> ORGANISM: Artificial Sequence
<220> FEATURE:
<223> OTHER INFORMATION: synthetic

<400> SEQUENCE: 184

Ala Arg Glu Asn Trp Ile Val Leu Lys Val Tyr Ala Gly Ile Val Gly

<210> SEQ ID NO 185
<211> LENGTH: 324
<212> TYPE: DNA
<213> ORGANISM: Artificial Sequence
<220> FEATURE:
<223> OTHER INFORMATION: synthetic

<400> SEQUENCE: 185

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaccttg gacgttcggc     300
caagggacca aggtggaaat caaa                                            324
```

<210> SEQ ID NO 186
<211> LENGTH: 108
<212> TYPE: PRT
<213> ORGANISM: Artificial Sequence
<220> FEATURE:
<223> OTHER INFORMATION: synthetic

<400> SEQUENCE: 186

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105

<210> SEQ ID NO 187
<211> LENGTH: 21
<212> TYPE: DNA
<213> ORGANISM: Artificial Sequence
<220> FEATURE:
<223> OTHER INFORMATION: synthetic

<400> SEQUENCE: 187

```
cagagtgtta gcagcagcta c                                                21
```

<210> SEQ ID NO 188
<211> LENGTH: 7
<212> TYPE: PRT
<213> ORGANISM: Artificial Sequence
<220> FEATURE:
<223> OTHER INFORMATION: synthetic

<400> SEQUENCE: 188

```
Gln Ser Val Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 ggtgcatcc                                                                9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Gly Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
cagcagtatg gtagctcacc ttggacg                                           27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Tyr Gly Ser Ser Pro Trp Thr
1               5

<210> SEQ ID NO 193
<211> LENGTH: 1061
<212> TYPE: PRT
<213> ORGANISM: Artificial Sequence
<220> FEATURE:
<223> OTHER INFORMATION: hNPR1

<400> SEQUENCE: 193

Met Pro Gly Pro Arg Arg Pro Ala Gly Ser Arg Leu Arg Leu Leu Leu
1               5                   10                  15

Leu Leu Leu Leu Pro Pro Leu Leu Leu Leu Arg Gly Ser His Ala
                20                  25                  30

Gly Asn Leu Thr Val Ala Val Val Leu Pro Leu Ala Asn Thr Ser Tyr
                35                  40                  45

Pro Trp Ser Trp Ala Arg Val Gly Pro Ala Val Glu Leu Ala Leu Ala
            50                  55                  60

Gln Val Lys Ala Arg Pro Asp Leu Leu Pro Gly Trp Thr Val Arg Thr
65                  70                  75                  80
```

-continued

Val Leu Gly Ser Ser Glu Asn Ala Leu Gly Val Cys Ser Asp Thr Ala
            85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Pro Val Gly Arg Phe
            115                 120                 125

Thr Ala His Trp Arg Val Pro Leu Leu Thr Gly Ala Pro Ala Leu
            130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
            165                 170                 175

Gly Trp Glu Arg Gln Ala Leu Met Leu Tyr Ala Tyr Arg Pro Gly Asp
            180                 185                 190

Glu Glu His Cys Phe Phe Leu Val Glu Gly Leu Phe Met Arg Val Arg
            195                 200                 205

Asp Arg Leu Asn Ile Thr Val Asp His Leu Glu Phe Ala Glu Asp Asp
            210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
            245                 250                 255

Leu Ala Leu Glu Ala Gly Leu Cys Gly Glu Asp Tyr Val Phe Phe His
            260                 265                 270

Leu Asp Ile Phe Gly Gln Ser Leu Gln Gly Gly Gln Gly Pro Ala Pro
            275                 280                 285

Arg Arg Pro Trp Glu Arg Gly Asp Gly Gln Asp Val Ser Ala Arg Gln
290                 295                 300

Ala Phe Gln Ala Ala Lys Ile Ile Thr Tyr Lys Asp Pro Asp Asn Pro
305                 310                 315                 320

Glu Tyr Leu Glu Phe Leu Lys Gln Leu Lys His Leu Ala Tyr Glu Gln
            325                 330                 335

Phe Asn Phe Thr Met Glu Asp Gly Leu Val Asn Thr Ile Pro Ala Ser
            340                 345                 350

Phe His Asp Gly Leu Leu Leu Tyr Ile Gln Ala Val Thr Glu Thr Leu
            355                 360                 365

Ala His Gly Gly Thr Val Thr Asp Gly Glu Asn Ile Thr Gln Arg Met
            370                 375                 380

Trp Asn Arg Ser Phe Gln Gly Val Thr Gly Tyr Leu Lys Ile Asp Ser
385                 390                 395                 400

Ser Gly Asp Arg Glu Thr Asp Phe Ser Leu Trp Asp Met Asp Pro Glu
            405                 410                 415

Asn Gly Ala Phe Arg Val Val Leu Asn Tyr Asn Gly Thr Ser Gln Glu
            420                 425                 430

Leu Val Ala Val Ser Gly Arg Lys Leu Asn Trp Pro Leu Gly Tyr Pro
            435                 440                 445

Pro Pro Asp Ile Pro Lys Cys Gly Phe Asp Asn Glu Asp Pro Ala Cys
450                 455                 460

Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
            485                 490                 495

Met Gln Leu Glu Lys Glu Leu Ala Ser Glu Leu Trp Arg Val Arg Trp

-continued

```
                500                 505                 510
Glu Asp Val Glu Pro Ser Ser Leu Glu Arg His Leu Arg Ser Ala Gly
            515                 520                 525
Ser Arg Leu Thr Leu Ser Gly Arg Gly Ser Asn Tyr Gly Ser Leu Leu
            530                 535                 540
Thr Thr Glu Gly Gln Phe Gln Val Phe Ala Lys Thr Ala Tyr Tyr Lys
545                 550                 555                 560
Gly Asn Leu Val Ala Val Lys Arg Val Asn Arg Lys Arg Ile Glu Leu
            565                 570                 575
Thr Arg Lys Val Leu Phe Glu Leu Lys His Met Arg Asp Val Gln Asn
            580                 585                 590
Glu His Leu Thr Arg Phe Val Gly Ala Cys Thr Asp Pro Pro Asn Ile
            595                 600                 605
Cys Ile Leu Thr Glu Tyr Cys Pro Arg Gly Ser Leu Gln Asp Ile Leu
            610                 615                 620
Glu Asn Glu Ser Ile Thr Leu Asp Trp Met Phe Arg Tyr Ser Leu Thr
625                 630                 635                 640
Asn Asp Ile Val Lys Gly Met Leu Phe Leu His Asn Gly Ala Ile Cys
            645                 650                 655
Ser His Gly Asn Leu Lys Ser Ser Asn Cys Val Val Asp Gly Arg Phe
            660                 665                 670
Val Leu Lys Ile Thr Asp Tyr Gly Leu Glu Ser Phe Arg Asp Leu Asp
            675                 680                 685
Pro Glu Gln Gly His Thr Val Tyr Ala Lys Lys Leu Trp Thr Ala Pro
            690                 695                 700
Glu Leu Leu Arg Met Ala Ser Pro Pro Val Arg Gly Ser Gln Ala Gly
705                 710                 715                 720
Asp Val Tyr Ser Phe Gly Ile Ile Leu Gln Glu Ile Ala Leu Arg Ser
            725                 730                 735
Gly Val Phe His Val Glu Gly Leu Asp Leu Ser Pro Lys Glu Ile Ile
            740                 745                 750
Glu Arg Val Thr Arg Gly Glu Gln Pro Pro Phe Arg Pro Ser Leu Ala
            755                 760                 765
Leu Gln Ser His Leu Glu Glu Leu Gly Leu Leu Met Gln Arg Cys Trp
            770                 775                 780
Ala Glu Asp Pro Gln Glu Arg Pro Pro Phe Gln Gln Ile Arg Leu Thr
785                 790                 795                 800
Leu Arg Lys Phe Asn Arg Glu Asn Ser Ser Asn Ile Leu Asp Asn Leu
            805                 810                 815
Leu Ser Arg Met Glu Gln Tyr Ala Asn Asn Leu Glu Glu Leu Val Glu
            820                 825                 830
Glu Arg Thr Gln Ala Tyr Leu Glu Lys Arg Lys Ala Glu Ala Leu
            835                 840                 845
Leu Tyr Gln Ile Leu Pro His Ser Val Ala Glu Gln Leu Lys Arg Gly
            850                 855                 860
Glu Thr Val Gln Ala Glu Ala Phe Asp Ser Val Thr Ile Tyr Phe Ser
865                 870                 875                 880
Asp Ile Val Gly Phe Thr Ala Leu Ser Ala Glu Ser Thr Pro Met Gln
            885                 890                 895
Val Val Thr Leu Leu Asn Asp Leu Tyr Thr Cys Phe Asp Ala Val Ile
            900                 905                 910
Asp Asn Phe Asp Val Tyr Lys Val Glu Thr Ile Gly Asp Ala Tyr Met
            915                 920                 925
```

Val Val Ser Gly Leu Pro Val Arg Asn Gly Arg Leu His Ala Cys Glu
        930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
            965                 970                 975

Thr Gly Pro Val Cys Ala Gly Val Val Gly Leu Lys Met Pro Arg Tyr
            980                 985                 990

Cys Leu Phe Gly Asp Thr Val Asn Thr Ala Ser Arg Met Glu Ser Asn
        995                 1000                1005

Gly Glu Ala Leu Lys Ile His Leu Ser Ser Glu Thr Lys Ala Val Leu
        1010                1015                1020

Glu Glu Phe Gly Gly Phe Glu Leu Glu Leu Arg Gly Asp Val Glu Met
1025                1030                1035                1040

Lys Gly Lys Gly Lys Val Arg Thr Tyr Trp Leu Leu Gly Glu Arg Gly
                1045                1050                1055

Ser Ser Thr Arg Gly
            1060

<210> SEQ ID NO 194
<211> LENGTH: 469
<212> TYPE: PRT
<213> ORGANISM: Artificial Sequence
<220> FEATURE:
<223> OTHER INFORMATION: hNPR1-mmH
      aa 1-441: hNPR1 aa G32-E473 from NM_000906.3; aa
      442-469: Myc-Myc-hexahistidine tag

<400> SEQUENCE: 194

Gly Asn Leu Thr Val Ala Val Val Leu Pro Leu Ala Asn Thr Ser Tyr
1               5                   10                  15

Pro Trp Ser Trp Ala Arg Val Gly Pro Ala Val Glu Leu Ala Leu Ala
            20                  25                  30

Gln Val Lys Ala Arg Pro Asp Leu Leu Pro Gly Trp Thr Val Arg Thr
        35                  40                  45

Val Leu Gly Ser Ser Glu Asn Ala Leu Gly Val Cys Ser Asp Thr Ala
    50                  55                  60

Ala Pro Leu Ala Ala Val Asp Leu Lys Trp Glu His Asn Pro Ala Val
65                  70                  75                  80

Phe Leu Gly Pro Gly Cys Val Tyr Ala Ala Ala Pro Val Gly Arg Phe
                85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
        115                 120                 125

Ser Tyr Ala Lys Leu Gly Asp Phe Val Ala Ala Leu His Arg Arg Leu
130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
        195                 200                 205

-continued

```
Val Ile Tyr Ile Cys Ser Ser Pro Asp Ala Phe Arg Thr Leu Met Leu
210                 215                 220
Leu Ala Leu Glu Ala Gly Leu Cys Gly Glu Asp Tyr Val Phe Phe His
225                 230                 235                 240
Leu Asp Ile Phe Gly Gln Ser Leu Gln Gly Gly Gln Gly Pro Ala Pro
            245                 250                 255
Arg Arg Pro Trp Glu Arg Gly Asp Gly Gln Asp Val Ser Ala Arg Gln
        260                 265                 270
Ala Phe Gln Ala Ala Lys Ile Ile Thr Tyr Lys Asp Pro Asp Asn Pro
    275                 280                 285
Glu Tyr Leu Glu Phe Leu Lys Gln Leu Lys His Leu Ala Tyr Glu Gln
290                 295                 300
Phe Asn Phe Thr Met Glu Asp Gly Leu Val Asn Thr Ile Pro Ala Ser
305                 310                 315                 320
Phe His Asp Gly Leu Leu Leu Tyr Ile Gln Ala Val Thr Glu Thr Leu
            325                 330                 335
Ala His Gly Gly Thr Val Thr Asp Gly Glu Asn Ile Thr Gln Arg Met
        340                 345                 350
Trp Asn Arg Ser Phe Gln Gly Val Thr Gly Tyr Leu Lys Ile Asp Ser
    355                 360                 365
Ser Gly Asp Arg Glu Thr Asp Phe Ser Leu Trp Asp Met Asp Pro Glu
370                 375                 380
Asn Gly Ala Phe Arg Val Leu Asn Tyr Asn Gly Thr Ser Gln Glu
385                 390                 395                 400
Leu Val Ala Val Ser Gly Arg Lys Leu Asn Trp Pro Leu Gly Tyr Pro
            405                 410                 415
Pro Pro Asp Ile Pro Lys Cys Gly Phe Asp Asn Glu Asp Pro Ala Cys
        420                 425                 430
Asn Gln Asp His Leu Ser Thr Leu Glu Glu Gln Lys Leu Ile Ser Glu
    435                 440                 445
Glu Asp Leu Gly Gly Glu Gln Lys Leu Ile Ser Glu Glu Asp Leu His
450                 455                 460
His His His His His
465
```

<210> SEQ ID NO 195
<211> LENGTH: 469
<212> TYPE: PRT
<213> ORGANISM: Artificial Sequence
<220> FEATURE:
<223> OTHER INFORMATION: mfNPR1-mmH
    aa 1-441: mf NPR1 aa G33-E473 of isoform X2 of
    XP_005541810.1; aa 442-469: Myc-Myc-hexahistidine
    tag

<400> SEQUENCE: 195

```
Gly Asn Leu Thr Val Ala Val Val Leu Pro Leu Ala Asn Thr Ser Tyr
1               5                   10                  15
Pro Trp Ser Trp Ala Arg Val Gly Pro Ala Val Glu Leu Ala Leu Ala
            20                  25                  30
Arg Val Lys Ala Arg Pro Asp Leu Leu Pro Gly Trp Thr Val Arg Thr
        35                  40                  45
Val Leu Gly Ser Ser Glu Asn Ala Leu Gly Val Cys Ser Asp Thr Ala
    50                  55                  60
Ala Pro Leu Ala Ala Val Asp Leu Lys Trp Glu His Asn Pro Ala Ala
65                  70                  75                  80
```

```
Phe Leu Gly Pro Gly Cys Val Tyr Ala Ala Ala Pro Val Gly Arg Phe
                85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
        115                 120                 125

Ser Tyr Ala Lys Leu Gly Asp Phe Val Ala Ala Leu His Arg Arg Leu
    130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
        195                 200                 205

Val Ile Tyr Ile Cys Ser Ser Pro Asp Ala Phe Arg Thr Leu Met Leu
    210                 215                 220

Leu Ala Leu Glu Ala Gly Leu Cys Gly Glu Asp Tyr Val Phe Phe His
225                 230                 235                 240

Leu Asp Ile Phe Gly Gln Ser Leu Gln Gly Gln Gly Pro Ala Pro
                245                 250                 255

Arg Arg Pro Trp Glu Arg Gly Asp Gln Asp Val Ser Ala Arg Gln
                260                 265                 270

Ala Phe Gln Ala Ala Lys Ile Ile Thr Tyr Lys Glu Pro Asp Asn Pro
    275                 280                 285

Glu Tyr Leu Glu Phe Leu Lys Gln Leu Lys His Leu Ala Arg Glu Gln
    290                 295                 300

Phe Asn Phe Thr Met Glu Asp Gly Leu Val Asn Thr Ile Pro Ala Ser
305                 310                 315                 320

Phe His Asp Gly Leu Leu Tyr Ile Gln Ala Val Thr Glu Thr Leu
                325                 330                 335

Ala His Gly Gly Thr Val Thr Asp Gly Glu Asn Ile Thr Gln Arg Met
            340                 345                 350

Trp Asn Arg Ser Phe Gln Gly Val Thr Gly Tyr Leu Lys Ile Asp Ser
        355                 360                 365

Ser Gly Asp Arg Glu Thr Asp Phe Ser Leu Trp Asp Met Asp Pro Glu
    370                 375                 380

Thr Gly Ala Phe Arg Val Val Leu Asn Tyr Asn Gly Thr Ser Gln Glu
385                 390                 395                 400

Leu Val Ala Val Ser Gly Arg Lys Leu Asn Trp Pro Leu Gly Tyr Pro
                405                 410                 415

Pro Pro Asp Ile Pro Lys Cys Gly Phe Asp Asn Glu Asp Pro Ala Cys
            420                 425                 430

Asn Gln Asp His Leu Ser Thr Leu Glu Glu Lys Leu Ile Ser Glu
        435                 440                 445

Glu Asp Leu Gly Gly Glu Gln Lys Leu Ile Ser Glu Glu Asp Leu His
    450                 455                 460

His His His His
465

<210> SEQ ID NO 196
<211> LENGTH: 469
<212> TYPE: PRT
```

<213> ORGANISM: Artificial Sequence
<220> FEATURE:
<223> OTHER INFORMATION: mNPR1-mmH
    aa 1-441: mouse NPR1 aa S29-E469 from NM_008727.5;
    aa 442-469: Myc-Myc-hexahistidine tag

<400> SEQUENCE: 196

```
Ser Asp Leu Thr Val Ala Val Val Leu Pro Leu Thr Asn Thr Ser Tyr
1               5                   10                  15

Pro Trp Ser Trp Ala Arg Val Gly Pro Ala Val Glu Leu Ala Leu Gly
            20                  25                  30

Arg Val Lys Ala Arg Pro Asp Leu Leu Pro Gly Trp Thr Val Arg Met
        35                  40                  45

Val Leu Gly Ser Ser Glu Asn Ala Ala Gly Val Cys Ser Asp Thr Ala
50                  55                  60

Ala Pro Leu Ala Ala Val Asp Leu Lys Trp Glu His Ser Pro Ala Val
65                  70                  75                  80

Phe Leu Gly Pro Gly Cys Val Tyr Ser Ala Ala Pro Val Gly Arg Phe
                85                  90                  95

Thr Ala His Trp Arg Val Pro Leu Leu Thr Ala Gly Ala Pro Ala Leu
            100                 105                 110

Gly Ile Gly Val Lys Asp Glu Tyr Ala Leu Thr Thr Arg Thr Gly Pro
        115                 120                 125

Ser His Val Lys Leu Gly Asp Phe Val Thr Ala Leu His Arg Arg Leu
130                 135                 140

Gly Trp Glu His Gln Ala Leu Val Leu Tyr Ala Asp Arg Leu Gly Asp
145                 150                 155                 160

Asp Arg Pro Cys Phe Phe Ile Val Glu Gly Leu Tyr Met Arg Val Arg
                165                 170                 175

Glu Arg Leu Asn Ile Thr Val Asn His Gln Glu Phe Val Glu Gly Asp
            180                 185                 190

Pro Asp His Tyr Thr Lys Leu Leu Arg Thr Val Gln Arg Lys Gly Arg
        195                 200                 205

Val Ile Tyr Ile Cys Ser Ser Pro Asp Ala Phe Arg Asn Leu Met Leu
210                 215                 220

Leu Ala Leu Asp Ala Gly Leu Thr Gly Glu Asp Tyr Val Phe Phe His
225                 230                 235                 240

Leu Asp Val Phe Gly Gln Ser Leu Gln Gly Ala Gln Gly Pro Val Pro
                245                 250                 255

Arg Lys Pro Trp Glu Arg Asp Asp Gly Gln Asp Arg Arg Ala Arg Gln
            260                 265                 270

Ala Phe Gln Ala Ala Lys Ile Ile Thr Tyr Lys Glu Pro Asp Asn Pro
        275                 280                 285

Glu Tyr Leu Glu Phe Leu Lys Gln Leu Lys Leu Ala Asp Lys Lys
290                 295                 300

Phe Asn Phe Thr Met Glu Asp Gly Leu Lys Asn Ile Ile Pro Ala Ser
305                 310                 315                 320

Phe His Asp Gly Leu Leu Leu Tyr Val Gln Ala Val Thr Glu Thr Leu
                325                 330                 335

Ala Gln Gly Gly Thr Val Thr Asp Gly Glu Asn Ile Thr Gln Arg Met
            340                 345                 350

Trp Asn Arg Ser Phe Gln Gly Val Thr Gly Tyr Leu Lys Ile Asp Arg
        355                 360                 365

Asn Gly Asp Arg Asp Thr Asp Phe Ser Leu Trp Asp Met Asp Pro Glu
370                 375                 380
```

```
Thr Gly Ala Phe Arg Val Val Leu Asn Phe Asn Gly Thr Ser Gln Glu
385                 390                 395                 400

Leu Met Ala Val Ser Glu His Arg Leu Tyr Trp Pro Leu Gly Tyr Pro
                405                 410                 415

Pro Pro Asp Ile Pro Lys Cys Gly Phe Asp Asn Glu Asp Pro Ala Cys
            420                 425                 430

Asn Gln Asp His Phe Ser Thr Leu Glu Glu Gln Lys Leu Ile Ser Glu
        435                 440                 445

Glu Asp Leu Gly Gly Glu Gln Lys Leu Ile Ser Glu Asp Leu His
    450                 455                 460

His His His His His
465

<210> SEQ ID NO 197
<211> LENGTH: 674
<212> TYPE: PRT
<213> ORGANISM: Artificial Sequence
<220> FEATURE:
<223> OTHER INFORMATION: hNPR1-mFc
     aa 1-441: human NPR1 amino acid G32-E473 from
     NM_000906.3; aa 442-674: Mouse IgG2a Fc tag

<400> SEQUENCE: 197

Gly Asn Leu Thr Val Ala Val Val Leu Pro Leu Ala Asn Thr Ser Tyr
1               5                   10                  15

Pro Trp Ser Trp Ala Arg Val Gly Pro Ala Val Glu Leu Ala Leu Ala
            20                  25                  30

Gln Val Lys Ala Arg Pro Asp Leu Leu Pro Gly Trp Thr Val Arg Thr
        35                  40                  45

Val Leu Gly Ser Ser Glu Asn Ala Leu Gly Val Cys Ser Asp Thr Ala
    50                  55                  60

Ala Pro Leu Ala Ala Val Asp Leu Lys Trp Glu His Asn Pro Ala Val
65                  70                  75                  80

Phe Leu Gly Pro Gly Cys Val Tyr Ala Ala Ala Pro Val Gly Arg Phe
                85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
        115                 120                 125

Ser Tyr Ala Lys Leu Gly Asp Phe Val Ala Leu His Arg Arg Leu
    130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
        195                 200                 205

Val Ile Tyr Ile Cys Ser Ser Pro Asp Ala Phe Arg Thr Leu Met Leu
    210                 215                 220

Leu Ala Leu Glu Ala Gly Leu Cys Gly Glu Asp Tyr Val Phe Phe His
225                 230                 235                 240

Leu Asp Ile Phe Gly Gln Ser Leu Gln Gly Gly Gln Gly Pro Ala Pro
                245                 250                 255
```

```
Arg Arg Pro Trp Glu Arg Gly Asp Gly Gln Asp Val Ser Ala Arg Gln
            260                 265                 270

Ala Phe Gln Ala Ala Lys Ile Ile Thr Tyr Lys Asp Pro Asp Asn Pro
        275                 280                 285

Glu Tyr Leu Glu Phe Leu Lys Gln Leu Lys His Leu Ala Tyr Glu Gln
    290                 295                 300

Phe Asn Phe Thr Met Glu Asp Gly Leu Val Asn Thr Ile Pro Ala Ser
305                 310                 315                 320

Phe His Asp Gly Leu Leu Tyr Ile Gln Ala Val Thr Glu Thr Leu
                325                 330                 335

Ala His Gly Gly Thr Val Thr Asp Gly Glu Asn Ile Thr Gln Arg Met
            340                 345                 350

Trp Asn Arg Ser Phe Gln Gly Val Thr Gly Tyr Leu Lys Ile Asp Ser
        355                 360                 365

Ser Gly Asp Arg Glu Thr Asp Phe Ser Leu Trp Asp Met Asp Pro Glu
    370                 375                 380

Asn Gly Ala Phe Arg Val Val Leu Asn Tyr Asn Gly Thr Ser Gln Glu
385                 390                 395                 400

Leu Val Ala Val Ser Gly Arg Lys Leu Asn Trp Pro Leu Gly Tyr Pro
                405                 410                 415

Pro Pro Asp Ile Pro Lys Cys Gly Phe Asp Asn Glu Asp Pro Ala Cys
            420                 425                 430

Asn Gln Asp His Leu Ser Thr Leu Glu Glu Pro Arg Gly Pro Thr Ile
        435                 440                 445

Lys Pro Cys Pro Pro Cys Lys Cys Pro Ala Pro Asn Leu Leu Gly Gly
    450                 455                 460

Pro Ser Val Phe Ile Phe Pro Pro Lys Ile Lys Asp Val Leu Met Ile
465                 470                 475                 480

Ser Leu Ser Pro Ile Val Thr Cys Val Val Val Asp Val Ser Glu Asp
                485                 490                 495

Asp Pro Asp Val Gln Ile Ser Trp Phe Val Asn Asn Val Glu Val His
            500                 505                 510

Thr Ala Gln Thr Gln Thr His Arg Glu Asp Tyr Asn Ser Thr Leu Arg
        515                 520                 525

Val Val Ser Ala Leu Pro Ile Gln His Gln Asp Trp Met Ser Gly Lys
    530                 535                 540

Glu Phe Lys Cys Lys Val Asn Asn Lys Asp Leu Pro Ala Pro Ile Glu
545                 550                 555                 560

Arg Thr Ile Ser Lys Pro Lys Gly Ser Val Arg Ala Pro Gln Val Tyr
                565                 570                 575

Val Leu Pro Pro Pro Glu Glu Glu Met Thr Lys Lys Gln Val Thr Leu
            580                 585                 590

Thr Cys Met Val Thr Asp Phe Met Pro Glu Asp Ile Tyr Val Glu Trp
        595                 600                 605

Thr Asn Asn Gly Lys Thr Glu Leu Asn Tyr Lys Asn Thr Glu Pro Val
    610                 615                 620

Leu Asp Ser Asp Gly Ser Tyr Phe Met Tyr Ser Lys Leu Arg Val Glu
625                 630                 635                 640

Lys Lys Asn Trp Val Glu Arg Asn Ser Tyr Ser Cys Ser Val Val His
                645                 650                 655

Glu Gly Leu His Asn His His Thr Thr Lys Ser Phe Ser Arg Thr Pro
            660                 665                 670

Gly Lys
```

<210> SEQ ID NO 198
<211> LENGTH: 674
<212> TYPE: PRT
<213> ORGANISM: Artificial Sequence
<220> FEATURE:
<223> OTHER INFORMATION: mfNPR1-mFc
aa 1-441: mf NPR1 amino acid G33-E473 of isoform
X2 of XP_005541810.1; aa 442-674: Mouse IgG2a Fc
tag

<400> SEQUENCE: 198

```
Gly Asn Leu Thr Val Ala Val Val Leu Pro Leu Ala Asn Thr Ser Tyr
1               5                   10                  15

Pro Trp Ser Trp Ala Arg Val Gly Pro Ala Val Glu Leu Ala Leu Ala
            20                  25                  30

Arg Val Lys Ala Arg Pro Asp Leu Leu Pro Gly Trp Thr Val Arg Thr
        35                  40                  45

Val Leu Gly Ser Ser Glu Asn Ala Leu Gly Val Cys Ser Asp Thr Ala
    50                  55                  60

Ala Pro Leu Ala Ala Val Asp Leu Lys Trp Glu His Asn Pro Ala Ala
65                  70                  75                  80

Phe Leu Gly Pro Gly Cys Val Tyr Ala Ala Ala Pro Val Gly Arg Phe
                85                  90                  95

Thr Ala His Trp Arg Val Pro Leu Leu Thr Ala Gly Ala Pro Ala Leu
            100                 105                 110

Gly Phe Gly Val Lys Asp Glu Tyr Ala Leu Thr Thr Arg Ala Gly Pro
        115                 120                 125

Ser Tyr Ala Lys Leu Gly Asp Phe Val Ala Ala Leu His Arg Arg Leu
    130                 135                 140

Gly Trp Glu Arg Gln Ala Leu Met Leu Tyr Ala Tyr Arg Pro Gly Asp
145                 150                 155                 160

Glu Glu His Cys Phe Phe Leu Val Glu Gly Leu Phe Met Arg Val Arg
                165                 170                 175

Asp Arg Leu Asn Ile Thr Val Asp His Leu Glu Phe Ala Glu Asp Asp
            180                 185                 190

Leu Ser His Tyr Thr Arg Leu Leu Arg Thr Met Pro Arg Lys Gly Arg
        195                 200                 205

Val Ile Tyr Ile Cys Ser Ser Pro Asp Ala Phe Arg Thr Leu Met Leu
    210                 215                 220

Leu Ala Leu Glu Ala Gly Leu Cys Gly Glu Asp Tyr Val Phe Phe His
225                 230                 235                 240

Leu Asp Ile Phe Gly Gln Ser Leu Gln Gly Gly Gln Gly Pro Ala Pro
                245                 250                 255

Arg Arg Pro Trp Glu Arg Gly Asp Gly Gln Asp Val Ser Ala Arg Gln
            260                 265                 270

Ala Phe Gln Ala Ala Lys Ile Ile Thr Tyr Lys Glu Pro Asp Asn Pro
        275                 280                 285

Glu Tyr Leu Glu Phe Leu Lys Gln Leu Lys His Leu Ala Arg Glu Gln
    290                 295                 300

Phe Asn Phe Thr Met Glu Asp Gly Leu Val Asn Thr Ile Pro Ala Ser
305                 310                 315                 320

Phe His Asp Gly Leu Leu Leu Tyr Ile Gln Ala Val Thr Glu Thr Leu
                325                 330                 335

Ala His Gly Gly Thr Val Thr Asp Gly Glu Asn Ile Thr Gln Arg Met
            340                 345                 350
```

```
Trp Asn Arg Ser Phe Gln Gly Val Thr Gly Tyr Leu Lys Ile Asp Ser
            355                 360                 365

Ser Gly Asp Arg Glu Thr Asp Phe Ser Leu Trp Asp Met Asp Pro Glu
    370                 375                 380

Thr Gly Ala Phe Arg Val Val Leu Asn Tyr Asn Gly Thr Ser Gln Glu
385                 390                 395                 400

Leu Val Ala Val Ser Gly Arg Lys Leu Asn Trp Pro Leu Gly Tyr Pro
                405                 410                 415

Pro Pro Asp Ile Pro Lys Cys Gly Phe Asp Asn Glu Asp Pro Ala Cys
            420                 425                 430

Asn Gln Asp His Leu Ser Thr Leu Glu Glu Pro Arg Gly Pro Thr Ile
            435                 440                 445

Lys Pro Cys Pro Pro Cys Lys Cys Pro Ala Pro Asn Leu Leu Gly Gly
    450                 455                 460

Pro Ser Val Phe Ile Phe Pro Pro Lys Ile Lys Asp Val Leu Met Ile
465                 470                 475                 480

Ser Leu Ser Pro Ile Val Thr Cys Val Val Val Asp Val Ser Glu Asp
                485                 490                 495

Asp Pro Asp Val Gln Ile Ser Trp Phe Val Asn Asn Val Glu Val His
            500                 505                 510

Thr Ala Gln Thr Gln Thr His Arg Glu Asp Tyr Asn Ser Thr Leu Arg
            515                 520                 525

Val Val Ser Ala Leu Pro Ile Gln His Gln Asp Trp Met Ser Gly Lys
    530                 535                 540

Glu Phe Lys Cys Lys Val Asn Asn Lys Asp Leu Pro Ala Pro Ile Glu
545                 550                 555                 560

Arg Thr Ile Ser Lys Pro Lys Gly Ser Val Arg Ala Pro Gln Val Tyr
                565                 570                 575

Val Leu Pro Pro Pro Glu Glu Glu Met Thr Lys Lys Gln Val Thr Leu
            580                 585                 590

Thr Cys Met Val Thr Asp Phe Met Pro Glu Asp Ile Tyr Val Glu Trp
            595                 600                 605

Thr Asn Asn Gly Lys Thr Glu Leu Asn Tyr Lys Asn Thr Glu Pro Val
    610                 615                 620

Leu Asp Ser Asp Gly Ser Tyr Phe Met Tyr Ser Lys Leu Arg Val Glu
625                 630                 635                 640

Lys Lys Asn Trp Val Glu Arg Asn Ser Tyr Ser Cys Ser Val Val His
                645                 650                 655

Glu Gly Leu His Asn His His Thr Thr Lys Ser Phe Ser Arg Thr Pro
            660                 665                 670

Gly Lys

<210> SEQ ID NO 199
<211> LENGTH: 674
<212> TYPE: PRT
<213> ORGANISM: Artificial Sequence
<220> FEATURE:
<223> OTHER INFORMATION: mNPR1-mFc
      aa 1-441: mouse NPR1 aa S29-E469 from NM_008727.5;
      aa 442-674: Mouse IgG2a Fc tag

<400> SEQUENCE: 199

Ser Asp Leu Thr Val Ala Val Val Leu Pro Leu Thr Asn Thr Ser Tyr
1               5                   10                  15

Pro Trp Ser Trp Ala Arg Val Gly Pro Ala Val Glu Leu Ala Leu Gly
```

```
                20                  25                  30
Arg Val Lys Ala Arg Pro Asp Leu Leu Pro Gly Trp Thr Val Arg Met
            35                  40                  45
Val Leu Gly Ser Ser Glu Asn Ala Ala Gly Val Cys Ser Asp Thr Ala
            50                  55                  60
Ala Pro Leu Ala Ala Val Asp Leu Lys Trp Glu His Ser Pro Ala Val
65                  70                  75                  80
Phe Leu Gly Pro Gly Cys Val Tyr Ser Ala Ala Pro Val Gly Arg Phe
                        85                  90                  95
Thr Ala His Trp Arg Val Pro Leu Leu Thr Ala Gly Ala Pro Ala Leu
                    100                 105                 110
Gly Ile Gly Val Lys Asp Glu Tyr Ala Leu Thr Thr Arg Thr Gly Pro
                115                 120                 125
Ser His Val Lys Leu Gly Asp Phe Val Thr Ala Leu His Arg Arg Leu
                130                 135                 140
Gly Trp Glu His Gln Ala Leu Val Leu Tyr Ala Asp Arg Leu Gly Asp
145                 150                 155                 160
Asp Arg Pro Cys Phe Phe Ile Val Glu Gly Leu Tyr Met Arg Val Arg
                        165                 170                 175
Glu Arg Leu Asn Ile Thr Val Asn His Gln Glu Phe Val Glu Gly Asp
                180                 185                 190
Pro Asp His Tyr Thr Lys Leu Leu Arg Thr Val Gln Arg Lys Gly Arg
                195                 200                 205
Val Ile Tyr Ile Cys Ser Ser Pro Asp Ala Phe Arg Asn Leu Met Leu
                210                 215                 220
Leu Ala Leu Asp Ala Gly Leu Thr Gly Glu Asp Tyr Val Phe Phe His
225                 230                 235                 240
Leu Asp Val Phe Gly Gln Ser Leu Gln Gly Ala Gln Gly Pro Val Pro
                        245                 250                 255
Arg Lys Pro Trp Glu Arg Asp Asp Gly Gln Asp Arg Arg Ala Arg Gln
                260                 265                 270
Ala Phe Gln Ala Ala Lys Ile Ile Thr Tyr Lys Glu Pro Asp Asn Pro
                275                 280                 285
Glu Tyr Leu Glu Phe Leu Lys Gln Leu Lys Leu Leu Ala Asp Lys Lys
                290                 295                 300
Phe Asn Phe Thr Met Glu Asp Gly Leu Lys Asn Ile Ile Pro Ala Ser
305                 310                 315                 320
Phe His Asp Gly Leu Leu Leu Tyr Val Gln Ala Val Thr Glu Thr Leu
                        325                 330                 335
Ala Gln Gly Gly Thr Val Thr Asp Gly Glu Asn Ile Thr Gln Arg Met
                340                 345                 350
Trp Asn Arg Ser Phe Gln Gly Val Thr Gly Tyr Leu Lys Ile Asp Arg
                355                 360                 365
Asn Gly Asp Arg Asp Thr Asp Phe Ser Leu Trp Asp Met Asp Pro Glu
                370                 375                 380
Thr Gly Ala Phe Arg Val Val Leu Asn Phe Asn Gly Thr Ser Gln Glu
385                 390                 395                 400
Leu Met Ala Val Ser Glu His Arg Leu Tyr Trp Pro Leu Gly Tyr Pro
                        405                 410                 415
Pro Pro Asp Ile Pro Lys Cys Gly Phe Asp Asn Glu Asp Pro Ala Cys
                420                 425                 430
Asn Gln Asp His Phe Ser Thr Leu Glu Glu Pro Arg Gly Pro Thr Ile
                435                 440                 445
```

```
Lys Pro Cys Pro Pro Cys Lys Cys Pro Ala Pro Asn Leu Leu Gly Gly
        450                 455             460

Pro Ser Val Phe Ile Phe Pro Pro Lys Ile Lys Asp Val Leu Met Ile
465             470             475                     480

Ser Leu Ser Pro Ile Val Thr Cys Val Val Asp Val Ser Glu Asp
                485             490             495

Asp Pro Asp Val Gln Ile Ser Trp Phe Val Asn Asn Val Glu Val His
            500             505             510

Thr Ala Gln Thr Gln Thr His Arg Glu Asp Tyr Asn Ser Thr Leu Arg
        515             520             525

Val Val Ser Ala Leu Pro Ile Gln His Gln Asp Trp Met Ser Gly Lys
    530             535             540

Glu Phe Lys Cys Lys Val Asn Asn Lys Asp Leu Pro Ala Pro Ile Glu
545             550             555             560

Arg Thr Ile Ser Lys Pro Lys Gly Ser Val Arg Ala Pro Gln Val Tyr
                565             570             575

Val Leu Pro Pro Pro Glu Glu Glu Met Thr Lys Lys Gln Val Thr Leu
            580             585             590

Thr Cys Met Val Thr Asp Phe Met Pro Glu Asp Ile Tyr Val Glu Trp
        595             600             605

Thr Asn Asn Gly Lys Thr Glu Leu Asn Tyr Lys Asn Thr Glu Pro Val
    610             615             620

Leu Asp Ser Asp Gly Ser Tyr Phe Met Tyr Ser Lys Leu Arg Val Glu
625             630             635             640

Lys Lys Asn Trp Val Glu Arg Asn Ser Tyr Ser Cys Ser Val Val His
                645             650             655

Glu Gly Leu His Asn His His Thr Thr Lys Ser Phe Ser Arg Thr Pro
            660             665             670

Gly Lys
```

ANTI-NPR1 ANTIBODIES AND USES THEREOF

CROSS-REFERENCE TO RELATED APPLICATIONS

This application is a divisional of U.S. patent application Ser. No. 16/657,000, filed Oct. 18, 2019, which claims the benefit under 35 U.S.C. § 119(e) of U.S. provisional application No. 62/749,557, filed on Oct. 23, 2018, and U.S. provisional application No. 62/755,720, filed on Nov. 5, 2018, the disclosures of which are herein incorporated by reference in its entirety.

SEQUENCE STATEMENT

The instant application contains a Sequence Listing, which has been submitted electronically in ASCII format and is hereby incorporated by reference in its entirety. Said ASCII copy, created on Oct. 16, 2019, is named SequenceList_10471US01.TXT and is 99.3 kilobytes in size.

FIELD OF THE INVENTION

The present invention is related to antibodies and antigen-binding fragments of antibodies that specifically bind to natriuretic peptide receptor 1 (NPR1), and therapeutic and diagnostic methods of using those antibodies.

BACKGROUND OF THE INVENTION

Natriuretic peptide receptor 1 (NPR1; also known as NPR-A) belongs to the cell-surface family of the guanylyl cyclase receptors, enzymes that catalyze the conversion of GTP into cyclic GMP. NPR1 is highly expressed in kidney, lungs, adrenal, vasculature, brain, liver, endothelial and adipose tissues and at lower levels in the heart. It is activated by binding to atrial natriuretic peptide (ANP) or brain natriuretic peptide (BNP). NPR1 activation and signaling stimulate many physiologic responses involving many tissues. The ANP-NPR1 system has been well studied for its role in vasorelaxation, natriuresis, diuresis, endothelial permeability and in non-cardiovascular functions like lipolysis and immune cell functions (Potter 2011, Pharmacol. Ther. 130: 71-82). Activation of NPR1 leads to natriuresis (excretion of salt by kidneys) and lowers blood pressure.

Monoclonal antibodies to NPR1 were first described by Kitano et al in 1995 in Immunol. Lett. 47: 215-22. Activating or agonist anti-NPR1 antibodies are disclosed in, for example, US Patent/Publication Nos. 9090695, and 20160168251, and in WO2010065293.

Fully human antibodies that specifically bind to NPR1 protein with high affinity and activate it could be important in the prevention and treatment of, e.g., hypertension, obesity and heart failure.

BRIEF SUMMARY OF THE INVENTION

The present invention provides antibodies and antigen-binding fragments thereof that specifically bind the natriuretic peptide receptor 1 (NPR1) protein. In certain embodiments, the anti-NPR1 antibodies are fully human antibodies that bind to NPR1 with high affinity and activate NPR1 or stabilize the activated conformation. The antibodies of the present invention are useful, inter alia, for activating or increasing the activity of NPR1 protein. In certain embodiments, the antibodies are useful in preventing, treating or ameliorating at least one symptom or indication of a NPR1-associated disease or disorder in a subject. In certain embodiments, the antibodies may be administered prophylactically or therapeutically to a subject having or at risk of having a NPR1-associated disease or disorder. In specific embodiments, the antibodies are used to decrease systemic blood pressure in a subject suffering from high blood pressure. Such antibodies can be used as therapy for a disorder such as heart failure when administered to a subject in need thereof.

In certain embodiments, the antibodies bind to NPR1 in the presence or absence of atrial natriuretic peptide (ANP) or brain natriuretic peptide (BNP), i.e., the antibodies are "peptide-independent binders." Such antibodies are advantageous as they can be used to bind and activate NPR1 irrespective of differing concentrations of endogenous ligand. Such antibodies when administered to a patient in need thereof can be advantageously used to avoid patient-to-patient variability (with respect to ligand concentration) in treatment. Further, the antibodies disclosed herein bind to NPR1 with high affinity and have improved pharmacokinetic properties (as compared to standard-of-care drugs). The antibodies showed a t ½ of up to 11 days in mice at a dose of 25 mg/kg. The antibodies are efficacious in lowering the blood pressure and maintaining the lowered pressure for as long as 28 days when administered to a subject in need thereof. A single dose of an antibody of the present invention led to sustained reduction in blood pressure. Such antibodies can be used to provide superior efficacy, along with less frequent dosing, in a subject with a NPR1-associated disease or disorder (e.g., hypertension).

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to increase persistence in the host or to eliminate residual effector functions (Reddy et al., 2000, J. Immunol. 164:1925-1933). In certain embodiments, the antibodies may be bispecific.

In a first aspect, the present invention provides isolated recombinant monoclonal antibodies or antigen-binding fragments thereof that bind specifically to NPR1.

In some embodiments, the present invention provides an isolated antibody or antigen-binding fragment thereof that binds specifically to natriuretic peptide receptor 1 (NPR1) protein, wherein the antibody or antigen-binding fragment thereof interacts with one or more amino acids contained within the extracellular domain of NPR1 (amino acids 29-347 of SEQ ID NO: 194), as determined by hydrogen/deuterium exchange, and wherein the antibody or antigen-binding fragment thereof: (i) binds to cells expressing human NPR1 in the presence or absence of atrial natriuretic peptide (ANP); and/or (ii) binds to NPR1 and activates NPR1.

In some embodiments, the antibodies are fully human monoclonal antibodies.

Exemplary anti-NPR1 antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDRs) (HCDR1, HCDR2 and HCDR3), and light chain complementarity determining regions (LCDRs) (LCDR1, LCDR2 and LCDR3) of exemplary antibodies. Table 2 sets forth the nucleic acid sequence identifiers of the HCVRs, LCVRs, HCDR1, HCDR2 HCDR3, LCDR1, LCDR2 and LCDR3 of the exemplary antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-NPR1 antibodies listed in Table 1. In certain embodiments, the HCVR/LCVR amino acid sequence pair is selected from one of SEQ ID NOs: 2/10 (e.g., mAb22033), and 66/74 (e.g., mAb22810).

The present invention also provides antibodies, or antigen-binding fragments thereof, comprising a HCVR and a LCVR, said HCVR comprising an amino acid sequence listed in Table 1 having no more than twelve amino acid substitutions, and/or said LCVR comprising an amino acid sequence listed in Table 1 having no more than ten amino acid substitutions. For example, the present invention provides antibodies or antigen-binding fragments thereof comprising a HCVR and a LCVR, said HCVR comprising an amino acid sequence listed in Table 1, said amino acid sequence having one, two, three, four, five, six, seven, eight, nine, ten, eleven or twelve amino acid substitutions. In another example, the present invention provides antibodies or antigen-binding fragments thereof comprising a HCVR and a LCVR, said LCVR comprising an amino acid sequence listed in Table 1, said amino acid sequence having one, two, three, four, five, six, seven, eight, nine or ten amino acid substitutions. In one embodiment, the present invention provides anti-NPR1 antibodies or antigen-binding fragments thereof comprising a HCVR and a LCVR, said HCVR comprising an amino acid sequence listed in Table 1, said amino acid sequence having at least one amino acid substitution, and/or said LCVR comprising an amino acid sequence listed in Table 1, said amino acid sequence having at least one amino acid substitution.

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-NPR1 antibodies listed in Table 1. In certain embodiments, the HCDR3/LCDR3 amino acid sequence pair is selected from the group consisting of SEQ ID NOs: 8/16 (e.g., mAb22033), and 72/80 (e.g., mAb22810).

The present invention also provides antibodies, or antigen-binding fragments thereof, comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antibodies, or antigen-binding fragments thereof, comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides antibodies, or antigen-binding fragments thereof, comprising a HCVR and a LCVR, said HCVR comprising HCDR1 comprising an amino acid sequence of SEQ ID NO: 4 or an amino acid sequence differing from SEQ ID NO: 4 by 1 amino acid, HCDR2 comprising an amino acid sequence of SEQ ID NO: 6 or an amino acid sequence differing from SEQ ID NO: 6 by 1 amino acid, and HCDR3 comprising an amino acid sequence of SEQ ID NO:

8 or an amino acid sequence differing from SEQ ID NO: 8 by 1 amino acid. In another exemplary embodiment, the present invention provides antibodies, or antigen-binding fragments thereof, comprising a HCVR and a LCVR, said LCVR comprising LCDR1 comprising an amino acid sequence of SEQ ID NO: 12 or an amino acid sequence differing from SEQ ID NO: 12 by 1 amino acid, LCDR2 comprising an amino acid sequence of SEQ ID NO: 14 or an amino acid sequence differing from SEQ ID NO: 14 by 1 amino acid, and LCDR3 comprising an amino acid sequence of SEQ ID NO: 16 or an amino acid sequence differing from SEQ ID NO: 16 by 1 amino acid.

The present invention also provides antibodies, or antigen-binding fragments thereof, comprising a set of six CDRs HCDR1-HCDR2-HCDR3-LCDR1-LCDR2-LCDR3) contained within any of the exemplary antibodies listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., mAb22033), and 68-70-72-76-78-80 (e.g., mAb22810).

In a related embodiment, the present invention provides antibodies, or antigen-binding fragments thereof, comprising a set of six CDRs HCDR1-HCDR2-HCDR3-LCDR1-LCDR2-LCDR3) contained within an HCVR/LCVR amino acid sequence pair as defined by any of the exemplary antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., mAb22033), and 66/74 (e.g., mAb22810). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the present invention includes an antibody or antigen-binding fragment thereof that binds specifically to NPR1, wherein the antibody or antigen-binding fragment thereof comprises three heavy chain complementarity determining regions (CDRs) (HCDR1, HCDR2 and HCDR3) contained within a heavy chain variable region (HCVR) and three light chain CDRs (LCDR1, LCDR2 and LCDR3) contained within a light chain variable region (LCVR), wherein the HCVR comprises: (i) an amino acid sequence selected from the group consisting of SEQ ID NOs: 2, 18, 34, 50, 66, 82, 98, 114, 130, 146, 162, and 178; (ii) an amino acid sequence having at least 90% identity to the amino acid sequence selected from the group consisting of SEQ ID NOs: 2, 18, 34, 50, 66, 82, 98, 114, 130, 146, 162, and 178; (iii) an amino acid sequence having at least 95% identity to the amino acid sequence selected from the group consisting of SEQ ID NOs: 2, 18, 34, 50, 66, 82, 98, 114, 130, 146, 162, and 178; or (iv) an amino acid sequence selected from the group consisting of SEQ ID NOs: 2, 18, 34, 50, 66, 82, 98, 114, 130, 146, 162, and 178, said amino acid sequence having no more than 12 amino acid substitutions; and the LCVR comprises: (a) an amino acid sequence selected from the group consisting of SEQ ID NOs: 10, 26, 42, 58, 74, 90, 106, 122, 138, 154, 170, and 186; (b) an amino acid sequence having at least 90% identity to the amino acid sequence selected from the group consisting of SEQ ID NOs: 10, 26, 42, 58, 74, 90, 106, 122, 138, 154, 170, and 186; (c) an amino acid sequence having at least 95% identity to the amino acid sequence selected from the group consisting of SEQ ID NOs: 10, 26, 42, 58, 74, 90, 106, 122, 138, 154, 170, and 186; or (d) an amino acid sequence selected from the group consisting of SEQ ID NOs: 10, 26, 42, 58, 74, 90, 106, 122, 138, 154, 170, and 186, said amino acid sequence having no more than 10 amino acid substitutions.

In certain preferred embodiments, the present invention includes antibodies that bind specifically to NPR1 in an agonist manner, i.e., potentiate or induce NPR1 binding and/or activity.

The present invention includes anti-NPR1 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In certain embodiments, the present invention provides antibodies and antigen-binding fragments thereof that exhibit pH-dependent binding to NPR1. For example, the present invention includes antibodies and antigen-binding fragment thereof that bind NPR1 with higher affinity at neutral pH than at acidic pH (i.e., reduced binding at acidic pH).

The present invention also provides for antibodies and antigen-binding fragments thereof that compete for specific binding to NPR1 with an antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that cross-compete for binding to NPR1 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

The present invention also provides antibodies and antigen-binding fragments thereof that bind to the same epitope as a reference antibody or antigen-binding fragment thereof comprising three CDRs of a HCVR and three CDRs of a LCVR, wherein the HCVR and LCVR each has an amino acid sequence selected from the HCVR and LCVR sequences listed in Table 1.

The present invention also provides isolated antibodies and antigen-binding fragments thereof that increase or stabilize NPR1 binding to its ligand (e.g., ANP or BNP). In some embodiments, the antibody or antigen-binding fragment thereof that activates NPR1 binding to ANP may bind to the same epitope on NPR1 as ANP or may bind to a different epitope on NPR1 as ANP.

In certain embodiments, the antibodies or antigen-binding fragments of the present invention are bispecific comprising a first binding specificity to a first epitope of NPR1 and a second binding specificity to a second epitope of NPR1 wherein the first and second epitopes are distinct and non-overlapping.

In certain embodiments, the present invention provides an isolated antibody or antigen-binding fragment thereof that has one or more of the following characteristics: (a) is a fully human monoclonal antibody; (b) binds to monomeric human NPR1 in the absence of ANP and/or BNP at 25° C. and at 37° C. with a dissociation constant ($K_D$) of less than 690 nM, as measured in a surface plasmon resonance assay; (c) binds to dimeric human NPR1 in the absence of ANP or BNP at 25° C. and at 37° C. with a $K_D$ of less than 42 nM, as measured in a surface plasmon resonance assay; (d) binds to human NPR1 complexed to ANP at 25° C. and 37° C. with a $K_D$ of less than 80 nM, as measured in a surface plasmon resonance assay; (e) binds to human NPR1 complexed to BNP at 25° C. and 37° C. with a $K_D$ of less than 20 nM, as measured in a surface plasmon resonance assay; (f) binds to monomeric monkey NPR1 in the absence of ANP and/or BNP at 25° C. and 37° C. with a $K_D$ of less than 365 nM, as measured in a surface plasmon resonance assay; (g) binds to dimeric monkey NPR1 in the absence of ANP or BNP at 25° C. and at 37° C. with a $K_D$ of less than 30 nM, as measured in a surface plasmon resonance assay; (h) binds to monkey NPR1 complexed to ANP at 25° C. and 37° C. with a $K_D$ of less than 10 nM, as measured in a surface plasmon resonance assay; (i) binds to monkey NPR1 complexed to BNP at 25° C. and 37° C. with a $K_D$ of less than 10 nM, as measured in a surface plasmon resonance assay; (j) does not bind to mouse NPR1; (k) binds to cells expressing human NPR1 (without ANP) or NPR1-complexed to ANP with a $EC_{50}$ less than 5 nM; (l) activates NPR1 with a $EC_{50}$ of less than 385 nM, as measured in a calcium flux cell-based bioassay; (m) reduces the systemic blood pressure when administered to normotensive and hypertensive mice, wherein the reduction in systemic and mean arterial blood pressures lasts for up to 28 days upon administration of a single dose; (n) improves glucose tolerance when administered to diet-induced obese mice; and (o) comprises a HCVR comprising an amino acid sequence selected from the group consisting of HCVR sequence listed in Table 1 and a LCVR comprising an amino acid sequence selected from the group consisting of LCVR sequences listed in Table 1.

In a second aspect, the present invention provides nucleic acid molecules encoding anti-NPR1 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs HCDR1-HCDR2-HCDR3), wherein the HCDR1-HCDR2-HCDR3 amino acid sequence set is as defined by any of the exemplary antibodies listed in Table 1.

The present invention also provides nucleic acid molecules encoding an LCVR, wherein the LCVR comprises a set of three CDRs LCDR1-LCDR2-LCDR3), wherein the LCDR1-LCDR2-LCDR3 amino acid sequence set is as defined by any of the exemplary antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 1, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-NPR1 antibody listed in Table 1.

In a related aspect, the present invention provides recombinant expression vectors capable of expressing a polypeptide comprising a heavy and/or light chain variable region of an antibody. For example, the present invention includes recombinant expression vectors comprising any of the nucleic acid molecules mentioned above, i.e., nucleic acid molecules encoding any of the HCVR, LCVR, and/or CDR sequences as set forth in Table 2. In certain embodiments, the present invention provides expression vectors comprising: (a) a nucleic acid molecule comprising a nucleic acid sequence encoding a HCVR of an antibody that binds NPR1, wherein the HCVR comprises an amino acid sequence selected from the group consisting of sequences listed in Table 1; and/or (b) a nucleic acid molecule comprising a nucleic acid sequence encoding a LCVR of an antibody that binds NPR1, wherein the LCVR comprises an amino acid sequence selected from the group consisting of sequences listed in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced. In certain embodiments, the host cells comprise a mammalian cell or a prokaryotic cell. In certain embodiments, the host cell is a Chinese Hamster Ovary (CHO) cell or an *Escherichia coli* (*E. coli*) cell. In certain embodiments, the present invention provides methods of producing an antibody or antigen-binding fragment thereof of the invention, the methods comprising introducing into a host cell an expression vector comprising a nucleic acid sequence encoding a HCVR and/or LCVR of an antibody or antigen-binding fragment thereof of the invention operably linked to a promoter; culturing the host cell under conditions favorable for expression of the nucleic acid sequence; and isolating the antibody or antigen-binding fragment thereof from the culture medium and/or host cell. The isolated antibody or antigen-binding fragment thereof may be purified using any of the methods known in prior art.

In a third aspect, the invention provides a pharmaceutical composition comprising a therapeutically effective amount of at least one recombinant monoclonal antibody or antigen-binding fragment thereof that specifically binds NPR1 and a pharmaceutically acceptable carrier. In a related aspect, the invention features a composition that is a combination of an anti-NPR1 antibody and a second therapeutic agent. In one embodiment, the second therapeutic agent is any agent that is advantageously combined with an anti-NPR1 antibody. Exemplary agents that may be advantageously combined with an anti-NPR1 antibody include, without limitation, other agents that bind and/or activate NPR1 activity (including other antibodies or antigen-binding fragments thereof, etc.) and/or agents which do not directly bind NPR1 but nonetheless treat or ameliorate at least one symptom or indication of a NPR1-associated disease or disorder (disclosed elsewhere herein).

Additional combination therapies and co-formulations involving the anti-NPR1 antibodies of the present invention are disclosed elsewhere herein.

In a fourth aspect, the invention provides therapeutic methods for treating a disease or disorder associated with NPR1 in a subject using an anti-NPR1 antibody or antigen-binding portion of an antibody of the invention, wherein the therapeutic methods comprise administering a therapeutically effective amount of a pharmaceutical composition comprising an antibody or antigen-binding fragment of an antibody of the invention to the subject in need thereof. The disorder treated is any disease or condition that is improved, ameliorated, inhibited or prevented by potentiation of NPR1 activity (e.g., hypertension). In certain embodiments, the invention provides methods to prevent, or treat a NPR1-associated disease or disorder comprising administering a therapeutically effective amount of an anti-NPR1 antibody or antigen-binding fragment thereof of the invention to a subject in need thereof. In some embodiments, the antibody or antigen-binding fragment thereof may be administered prophylactically or therapeutically to a subject having or at risk of having a NPR1-associated disease or disorder. In certain embodiments, the antibody or antigen-binding fragment thereof the invention is administered in combination with a second therapeutic agent to the subject in need thereof. The second therapeutic agent may be selected from the group consisting of an aldosterone antagonist, an alpha-adrenergic blocker, an angiotensin converting enzyme (ACE) inhibitor, an arteriolar vasodilator, an autonomic ganglionic vasodilator, a beta-adrenergic blocker, a catecholamine-depleting sympatholytic, a central alpha-2 adrenergic agonist, a calcium channel blocker, a diuretic, a renin inhibitor, an anti-coagulant, an anti-platelet agent, a cholesterol lowering agent, a vasodilator, digitalis, surgery, an implantable device, anti-tumor therapy, insulin, a GLP1 agonist, metformin, dialysis, bone marrow stimulant, hemofiltration, a lifestyle modification, a dietary supplement and any other drug or therapy known in the art. In certain embodiments, the second therapeutic agent may be an agent that helps to counteract or reduce any possible side effect(s) associated with an antibody or antigen-binding fragment thereof of the invention, if such side effect(s) should occur. The antibody or fragment thereof may be administered subcutaneously, intravenously, intradermally, intraperitoneally, orally, or intramuscularly. The antibody or fragment thereof may be administered at a dose of about 0.1 mg/kg of body weight to about 100 mg/kg of body weight of the subject. In certain embodiments, an antibody of the present invention may be administered at one or more doses comprising between 10 mg to 600 mg.

The present invention also includes use of an anti-NPR1 antibody or antigen-binding fragment thereof of the invention in the manufacture of a medicament for the treatment of a disease or disorder that would benefit from the activation of NPR1 binding and/or activity.

Other embodiments will become apparent from a review of the ensuing detailed description.

BRIEF DESCRIPTION OF THE FIGURES

(FIG. 6A) End systolic volume (%); and (FIG. 6B) End diastolic volume (%) in telemetered normotensive NPR1$^{hu/hu}$ mice randomized into five groups of equal body weight and given a single subcutaneous injection of mAb22033 at the doses listed in Table 32. An IgG4 antibody was used as isotype control. Echocardiography was performed on anesthetized mice in the short axis on day 28 post-dose using a high frequency ultrasound system and probe. All values are mean ±SEM, n=6-7 per group. Statistics—one-way ANOVA with Dunnett's; *p<0.05 vs. IgG4 isotype control.

(FIG. 7A) Fractional shortening (%); and (FIG. 7B) Ejection fraction (%) in telemetered normotensive NPR1$^{hu/hu}$ mice randomized into five groups of equal body weight and given a single subcutaneous injection of mAb22033 at the doses listed in Table 32. An IgG4 antibody was used as isotype control. Echocardiography was performed on anesthetized mice in the short axis on day 28 post-dose using a high frequency ultrasound system and probe. All values are mean ±SEM, n=6-7 per group. Statistics—one-way ANOVA with Dunnett's.

(FIG. 16A) end systolic volume %; and (FIG. 16B) end diastolic volume % in telemetered hypertensive NPR1$^{hu/hu}$ mice randomized into five groups of equal systolic blood pressures and administered either a single subcutaneous dose or twice weekly for 3 weeks of mAb22033 at the doses listed in Table 40. An IgG4 antibody was used as isotype control. Echocardiography was performed on anesthetized mice in the short axis on day 21 post-dose using a high frequency ultrasound system and probe. All values are mean ±SEM, n=5-6 per group. Statistics—one-way ANOVA with Dunnett's.

(FIG. 17A) Fractional shortening (%); and (FIG. 17B) Ejection fraction (%) in telemetered hypertensive NPR1$^{hu/hu}$ mice randomized into five groups of equal systolic blood pressures and administered either a single subcutaneous dose or twice weekly for 3 weeks of mAb22033 at the doses listed in Table 40. An IgG4 antibody was used as isotype control. Echocardiography was performed on anesthetized mice in the short axis on day 21 post-dose using a high frequency ultrasound system and probe. All values are mean ±SEM, n=5-6 per group. Statistics—one-way ANOVA with Dunnett's.

FIGS. 22A, 22B, and 22C show changes in VO$_2$ (FIG. 22A), VCO$_2$ (FIG. 22B) or Energy Expenditure (FIG. 22C) broken down as the average of each day/night cycle after one week of treatment with either mAb22033 NPR1 agonist mAb, hFc.FGF21 or an isotype control mAb. After one week of treatment, mice from each group were placed in a Columbia Instruments metabolic cage system (CLAMS) for one week to record metabolic parameters. Mice were acclimated to the cages for one week prior to measurement to minimize stress. A human IgG4 antibody was used as isotype control. All values are mean ±SEM, n=5-6 per group. ****=P<0.0001 vs isotype control. Statistics by one-way ANOVA+Bonferonni.

DETAILED DESCRIPTION

Figure 1:
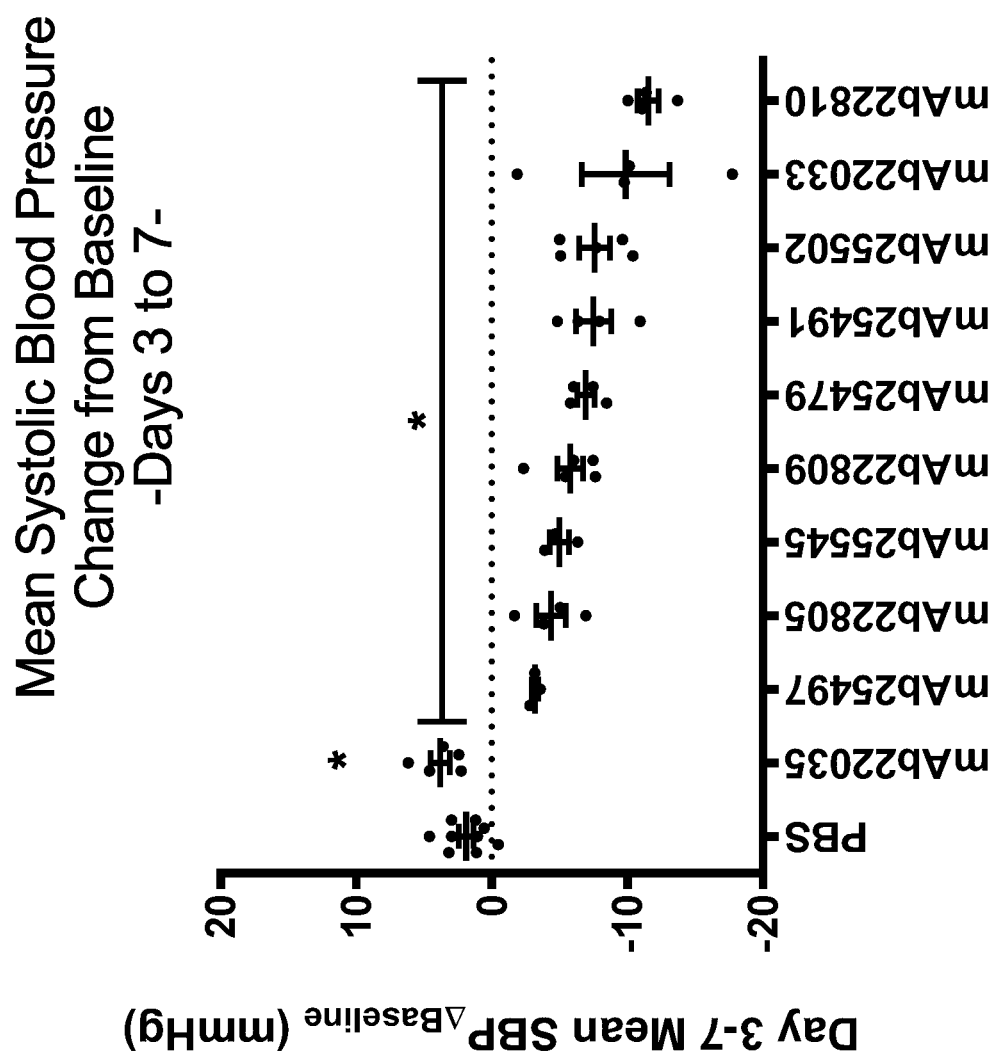
FIG. 1 shows the effect of selected anti-NPR1 agonist antibodies on systolic blood pressure in normotensive NPR1$^{hu/hu}$ mice. Telemetered normotensive NPR1$^{hu/hu}$ mice were randomized into groups based off of body weight. Animals were given a single 25 mg/kg subcutaneous injection of an NPR1 agonist antibody or PBS control as described in Table 30. All values are mean change from baseline for days 3-7±SEM, n=3-9 per group. Statistics—one-way ANOVA with Dunnett's; *p<0.05 vs. PBS control.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "NPR1", also called "NPRA" refers to natriuretic peptide receptor 1 (also known as natriuretic peptide receptor A). NPR1 is a homodimeric transmembrane guanylate cyclase, an enzyme that catalyzes cGMP synthesis. NPR1 is the receptor for both atrial (ANP) and brain (BNP) natriuretic peptides and undergoes conformational changes in the extracellular domain upon ligand binding (Ogawa et al 2004, J. Biol. Chem. 279: 28625-31). The protein has 4 distinct regions comprising an extracellular ligand-binding domain, a single transmembrane-spanning region, an intracellular protein kinase-like homology domain and a guanylyl cyclase catalytic domain. The amino acid sequence of full-length NPR1 protein is exemplified by the amino acid sequence provided in UniProtKB/Swiss-Prot as accession number P16066.1 (SEQ ID NO: 193). The term "NPR1" includes recombinant NPR1 protein or a fragment thereof. The term also encompasses NPR1 protein or a fragment thereof coupled to, for example, histidine tag, mouse or human Fc, or a signal sequence such as ROR1 (for example, SEQ ID NOs: 194-199).

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-NPR1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic biological properties, reduced immunogenicity, etc. Antibodies and antigen-binding fragments obtained in this general manner are encompassed within the present invention.

The present invention also includes fully human anti-NPR1 monoclonal antibodies comprising variants of any of the HCVR, LCVR, and/or CDR amino acid sequences disclosed herein having one or more conservative substitutions. For example, the present invention includes anti-NPR1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", or "fully human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", or "fully human antibody", as used herein, is not intended to include mAbs in which CDR sequences derived from the germline of another mammalian species (e.g., mouse), have been grafted onto human FR sequences. The term includes antibodies that are recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to NPR1. Moreover, multi-specific antibodies that bind to one domain in NPR1 and one or more additional antigens or a bi-specific that binds to two different regions of NPR1 are nonetheless considered antibodies that "specifically bind", as used herein.

The term "high affinity" antibody refers to those mAbs having a binding affinity to NPR1, expressed as $K_D$, of at least $10^{-8}$ M; preferably $10^{-9}$ M; more preferably $10^{-10}$ M, even more preferably $10^{-11}$ M, as measured by surface plasmon resonance, e.g., BIACORE™ or solution-affinity ELISA.

By the term "slow off rate", "Koff" or "kd" is meant an antibody that dissociates from NPR1, with a rate constant of $1\times10^{-3}$ s$^{-1}$ or less, preferably $1\times10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to NPR1 protein.

In specific embodiments, antibody or antibody fragments of the invention may be conjugated to a moiety such a ligand or a therapeutic moiety ("immunoconjugate"), a second anti-NPR1 antibody, or any other therapeutic moiety useful for treating a NPR1-associated disease or disorder.

An "isolated antibody", as used herein, is intended to refer to an antibody that is substantially free of other antibodies (Abs) having different antigenic specificities (e.g., an isolated antibody that specifically binds NPR1, or a fragment thereof, is substantially free of Abs that specifically bind antigens other than NPR1.

An "activating antibody" or an "agonist antibody", as used herein (or an "antibody that increases or potentiates NPR1 activity" or "an antibody that stabilizes the activated conformation"), is intended to refer to an antibody whose binding to NPR1 results in activation of at least one biological activity of NPR1. For example, an antibody of the invention may decrease systemic blood pressure upon administration to a subject in need thereof.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "cross-competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a NPR1-associated disease or disorder such as hypertension. The term includes human subjects who have or are at risk of having such a disease or disorder.

As used herein, the terms "treat", "treating", or "treatment" refer to the reduction or amelioration of the severity of at least one symptom or indication of a NPR1-associated disease or disorder due to the administration of a therapeutic agent such as an antibody of the present invention to a subject in need thereof. The terms include inhibition of progression of disease or of worsening of a symptom/indication. The terms also include positive prognosis of disease, i.e., the subject may be free of disease or may have reduced disease upon administration of a therapeutic agent such as an antibody of the present invention. The therapeutic agent may be administered at a therapeutic dose to the subject.

The terms "prevent", "preventing" or "prevention" refer to inhibition of manifestation of a NPR1-associated disease or disorder or any symptoms or indications of such a disease or disorder upon administration of an antibody of the present invention.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to NPR1 protein. An antibody fragment may include a Fab fragment, a F(ab')$_2$ fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to NPR1.

An immunogen comprising any one of the following can be used to generate antibodies to NPR1 protein. In certain embodiments, the antibodies of the invention are obtained from mice immunized with a full length, native NPR1 protein (See, for example, UniProtKB/Swiss-Prot accession number P16066.1) or with DNA encoding the protein or fragment thereof. Alternatively, the protein or a fragment thereof may be produced using standard biochemical techniques and modified and used as immunogen.

In some embodiments, the immunogen may be a recombinant NPR1 protein or fragment thereof expressed in *E. coli* or in any other eukaryotic or mammalian cells such as Chinese hamster ovary (CHO) cells (for example, SEQ ID NOs: 194-199)

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to NPR1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-NPR1 antibodies and antibody fragments of the present invention encompass proteins having amino acid sequences that vary from those of the described antibodies, but that retain the ability to bind NPR1 protein. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, or potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-NPR1 Antibodies Comprising Fc Variants

According to certain embodiments of the present invention, anti-NPR1 antibodies are provided comprising an Fc domain comprising one or more mutations which enhance or diminish antibody binding to the FcRn receptor, e.g., at acidic pH as compared to neutral pH. For example, the present invention includes anti-NPR1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-NPR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations and other mutations within the antibody variable domains disclosed herein, are contemplated within the scope of the present invention.

The present invention also includes anti-NPR1 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Patent Application Publication 2014/0243504, the disclosure of which is hereby incorporated by reference in its entirety).

Biological Characteristics of the Antibodies

In general, the antibodies of the present invention function by binding to NPR1 protein and increasing its activity. For example, the present invention includes antibodies and antigen-binding fragments of antibodies that bind monomeric human NPR1 protein in the absence of either ANP or BNP (e.g., at 25° C. or at 37° C.) with a $K_D$ of less than 690 nM as measured by surface plasmon resonance, e.g., using the assay format as defined in Example 3 herein. In certain embodiments, the antibodies or antigen-binding fragments thereof bind NPR1 with a $K_D$ of less than about 650 nM, less than about 500 nM, less than about 400 nM, less than about 300 nM, less than about 200 nM, less than about 100 nM, less than about 50 nM, or less than about 25 nM, as measured by surface plasmon resonance, e.g., using the assay format as defined in Example 3 herein, or a substantially similar assay.

The present invention also includes antibodies and antigen-binding fragments of antibodies that bind dimeric human NPR1 protein in the absence of either ANP or BNP (e.g., at 25° C. or at 37° C.) with a $K_D$ of less than 42 nM as measured by surface plasmon resonance, e.g., using the assay format as defined in Example 3 herein. In certain embodiments, the antibodies or antigen-binding fragments thereof bind NPR1 with a $K_D$ of less than about 40 nM, less than about 30 nM, less than about 20 nM, less than about 10 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind human NPR1 protein complexed to ANP (e.g., at 25° C. or at 37° C.) with a $K_D$ of less than 80 nM as measured by surface plasmon resonance, e.g., using the assay format as defined in Example 3 herein. In certain embodiments, the antibodies or antigen-binding fragments thereof bind NPR1 with a $K_D$ of less than about 70 nM, less than about 50 nM, less than about 25 nM, less than about 10 nM, less than about 5 nM, less than about 1nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind human NPR1 protein complexed to BNP (e.g., at 25° C. or at 37° C.) with a $K_D$ of less than 20 nM as measured by surface plasmon resonance, e.g., using the assay format as defined in Example 3 herein. In certain embodiments, the antibodies or antigen-binding fragments thereof bind NPR1 with a $K_D$ of less than about 15 nM, less than about 10 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind monomeric monkey NPR1 protein in the absence of either ANP or BNP (e.g., at 25° C. or at 37° C.) with a $K_D$ of less than 365 nM as measured by surface plasmon resonance, e.g., using the assay format as defined in Example 3 herein. In certain embodiments, the antibodies or antigen-binding fragments thereof bind NPR1 with a $K_D$ of less than about 360 nM, less than about 300 nM, less than about 150 nM, less than about 100 nM, less than about 50 nM, less than about 25nM, less than about 10 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind dimeric monkey NPR1 protein in the absence of either ANP or BNP (e.g., at 25° C. or at 37° C.) with a $K_D$ of less than 30 nM as measured by surface plasmon resonance, e.g., using the assay format as defined in Example 3 herein. In certain embodiments, the antibodies or antigen-binding fragments thereof bind NPR1 with a $K_D$ of less than about 20 nM, less than about 10 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind monkey NPR1 protein complexed to ANP (e.g., at 25° C. or at 37° C.) with a $K_D$ of less than 10nM as measured by surface plasmon resonance, e.g., using the assay format as defined in Example 3 herein. In certain embodiments, the antibodies or antigen-binding fragments thereof bind NPR1 with a $K_D$ of less than about 9 nM, less than about 8 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments of antibodies that bind dimeric monkey NPR1 protein complexed to BNP (e.g., at 25° C. or at 37° C.) with a $K_D$ of less than 10 nM as measured by surface plasmon resonance, e.g., using the assay format as defined in Example 3 herein. In certain embodiments, the antibodies or antigen-binding fragments thereof bind NPR1 with a $K_D$ of less than about 9 nM, less than about 8 nM, less than about 5 nM, less than about 1 nM, or less than about 0.5 nM, as measured by surface plasmon resonance, e.g., using the assay format as defined in Example 3 herein, or a substantially similar assay.

The present invention also includes antibodies and antigen-binding fragments thereof that bind to cells expressing human NPR1 with or without ANP at a $EC_{50}$ of less than 5 nM, less than 4 nM, less than 3 nM, less than 2 nM, less than 1 nM, or less than 0.5 nM, as measured, e.g., using an assay format as described in Example 5 herein, or a substantially similar assay.

The present invention also includes antibodies and antigen-binding fragments thereof that activate NPR1 with a $EC_{50}$ of less than 385 nM, as measured by a calcium flux cell-based bioassay, e.g., using the assay format as defined in Example 6 herein. In certain embodiments, the antibodies or antigen-binding fragments thereof activate NPR1 with a $EC_{50}$ of less than about 300 nM, less than about 200 nM, less than about 100 nM, less than about 50 nM, less than about 10 nM, or less than about 1 nM, as measured by calcium flux cell-based bioassay, e.g., using the assay format as defined in Example 6 herein, or a substantially similar assay.

The present invention also includes antibodies and antigen-binding fragments of antibodies that bind to NPR1 and decrease the systemic blood pressure of a subject for more than 28 days when administered to the subject in need thereof as a single dose, e.g., as shown in Example 8 herein.

The present invention also includes antibodies and antigen-binding fragments of antibodies that bind to NPR1 and reduced fasting blood glucose levels when administered to a subject in need thereof, e.g., as shown in Example 11 herein.

In one embodiment, the present invention provides an isolated recombinant antibody or antigen-binding fragment thereof that binds specifically to NPR1 protein in the presence or absence of ANP or BNP and increases the activity of NPR1, wherein the antibody or fragment thereof exhibits one or more of the following characteristics: (a) is a fully human monoclonal antibody; (b) binds to monomeric human NPR1 in the absence of ANP and/or BNP at 25° C. and at 37° C. with a dissociation constant ($K_D$) of less than 690 nM, as measured in a surface plasmon resonance assay; (c) binds to dimeric human NPR1 in the absence of ANP or BNP at 25° C. and at 37° C. with a $K_D$ of less than 42 nM, as measured in a surface plasmon resonance assay; (d) binds to human NPR1 complexed to ANP at 25° C. and 37° C. with a $K_D$ of less than 80 nM, as measured in a surface plasmon resonance assay; (e) binds to human NPR1 complexed to BNP at 25° C. and 37° C. with a $K_D$ of less than 20 nM, as measured in a surface plasmon resonance assay; (f) binds to monomeric monkey NPR1 in the absence of ANP and/or BNP at 25° C. and 37° C. with a $K_D$ of less than 365 nM, as measured in a surface plasmon resonance assay; (g) binds to dimeric monkey NPR1 in the absence of ANP or BNP at 25° C. and at 37° C. with a $K_D$ of less than 30 nM, as measured in a surface plasmon resonance assay; (h) binds to monkey NPR1 complexed to ANP at 25° C. and 37° C. with a $K_D$ of less than 10 nM, as measured in a surface plasmon resonance assay; (i) binds to monkey NPR1 complexed to BNP at 25° C. and 37° C. with a $K_D$ of less than 10 nM, as measured in a surface plasmon resonance assay; (j) does not bind to mouse NPR1; (k) binds to cells expressing human NPR1 (in the absence of ANP) or NPR1-complexed to ANP with $EC_{50}$ less than 5 nM; (l) activates NPR1 with a $EC_{50}$ of less than 385 nM, as measured in a calcium flux cell-based bioassay; (m) reduces the systemic blood pressure when administered to normotensive and hypertensive mice, wherein the reduction in systemic and mean arterial blood pressures lasts for up to 28 days upon administration of a single dose; (n) improves glucose tolerance when administered to diet-induced obese mice; and (o) comprises a HCVR comprising an amino acid sequence selected from the group consisting of HCVR sequence listed in Table 1 and a LCVR comprising an amino acid sequence selected from the group consisting of LCVR sequences listed in Table 1.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Epitope Mapping and Related Technologies

The present invention includes anti-NPR1 antibodies that interact with one or more amino acids found within one or more regions of the NPR1 protein molecule. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned domains of the NPR1 protein molecule (e.g. a linear epitope in a domain). Alternatively, the epitope may consist of a plurality of non-contiguous amino acids (or amino acid sequences) located within either or both of the aforementioned domains of the protein molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the present invention includes anti-NPR1 antibodies and antigen-binding fragments thereof that interact with one or more epitopes found within the extracellular domain of NPR1. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within the extracellular domain of NPR1. Alternatively, the epitope may consist of a plurality of non-contiguous amino acids (or amino acid sequences) located within NPR1.

The present invention includes anti-NPR1 antibodies that bind to the same epitope, or a portion of the epitope, as any of the specific exemplary antibodies listed in Table 1. Likewise, the present invention also includes anti-NPR1 antibodies that compete for binding to NPR1 protein or a fragment thereof with any of the specific exemplary antibodies listed in Table 1. For example, the present invention includes anti-NPR1 antibodies that cross-compete for binding to NPR1 protein with one or more antibodies listed in Table 1.

One can easily determine whether an antibody binds to the same epitope as, or competes for binding with, a reference anti-NPR1 antibody by using routine methods known in the art. For example, to determine if a test antibody binds to the same epitope as a reference anti-NPR1 antibody of the invention, the reference antibody is allowed to bind to a NPR1 protein or peptide under saturating conditions. Next, the ability of a test antibody to bind to the NPR1 protein molecule is assessed. If the test antibody is able to bind to NPR1 following saturation binding with the reference anti-NPR1 antibody, it can be concluded that the test antibody binds to a different epitope than the reference anti-NPR1 antibody. On the other hand, if the test antibody is not able to bind to the NPR1 protein following saturation binding with the reference anti-NPR1 antibody, then the test antibody may bind to the same epitope as the epitope bound by the reference anti-NPR1 antibody of the invention.

To determine if an antibody competes for binding with a reference anti-NPR1 antibody, the above-described binding methodology is performed in two orientations: In a first orientation, the reference antibody is allowed to bind to a NPR1 protein under saturating conditions followed by assessment of binding of the test antibody to the NPR1 molecule. In a second orientation, the test antibody is allowed to bind to a NPR1 molecule under saturating conditions followed by assessment of binding of the reference antibody to the NPR1 molecule. If, in both orientations, only the first (saturating) antibody is capable of binding to the NPR1 molecule, then it is concluded that the test antibody and the reference antibody compete for binding to NPR1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

In certain embodiments, the present invention provides an isolated antibody or antigen-binding fragment thereof that binds specifically to natriuretic peptide receptor 1 (NPR1) protein, wherein the antibody or antigen-binding fragment thereof interacts with one or more amino acids contained within the extracellular domain of NPR1 (amino acids 29-347 of SEQ ID NO: 194), as determined by hydrogen/deuterium exchange, and wherein the antibody or antigen-binding fragment thereof: (i) binds to cells expressing human NPR1 in the presence or absence of atrial natriuretic peptide (ANP); and/or (ii) binds to NPR1 and activates NPR1. In one embodiment, the antibody or antigen-binding fragment thereof interacts with an amino acid sequence selected from the group consisting of (a) amino acids 29 to 45 of SEQ ID NO: 194; (b) amino acids 331 to 347 of SEQ ID NO: 194; (c) amino acids 336 to 347 of SEQ ID NO: 194; (d) amino acids 331 to 335 of SEQ ID NO: 194; and (e) amino acids 70 to 81 of SEQ ID NO: 194. In one embodiment, the antibody or antigen-binding fragment thereof interacts with an amino acid sequence selected from the group consisting of (a) amino acids 29 to 45 of SEQ ID NO: 194; and (b) amino acids 336 to 347 of SEQ ID No: 194. In one embodiment, the antibody or antigen-binding fragment thereof interacts with an amino acid sequence selected from the group consisting of (a) amino acids 29 to 45 of SEQ ID NO: 194; and (b) amino acids 331 to 347 of SEQ ID No: 194, in the presence of ANP. In one embodiment, the antibody or antigen-binding fragment thereof interacts with an amino acid sequence selected from the group consisting of (a) amino acids 29 to 45 of SEQ ID NO: 194; (b) amino acids 70 to 81 of SEQ ID NO: 194; and (c) amino acids 331 to 335 of SEQ ID No: 194, in the presence of ANP. In one embodiment, the present invention provides an isolated antibody or antigen-binding fragment thereof that binds specifically to NPR1 protein in the presence of ANP, wherein the antibody or antigen-binding fragment thereof interacts with an amino acid sequence selected from the group consisting of (a) amino acids 29 to 45 of SEQ ID NO: 194; and (b) amino acids 331 to 347 of SEQ ID No: 194, but not with amino acids 70 to 81 of SEQ ID NO: 194, as determined by hydrogen/deuterium exchange, and wherein the antibody or antigen-binding fragment thereof: (i) binds to cells expressing human NPR1 in the presence or absence of ANP; and/or (ii) binds to NPR1 and activates NPR1.

Immunoconjugates

The invention encompasses a human anti-NPR1 monoclonal antibody conjugated to a therapeutic moiety ("immunoconjugate"), to treat a NPR1-associated disease or disorder (e.g., hypertension). As used herein, the term "immunoconjugate" refers to an antibody that is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target. Examples of immunoconjugates include antibody drug conjugates and antibody-toxin fusion proteins. In one embodiment, the agent may be a second different antibody to NPR1 protein. The type of therapeutic moiety that may be conjugated to the anti-NPR1 antibody and will take into account the condition to be treated and the desired therapeutic effect to be achieved. Examples of suitable agents for forming immunoconjugates are known in the art; see for example, WO 05/103081.

Multi-Specific Antibodies

The antibodies of the present invention may be monospecific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244.

Any of the multi-specific antigen-binding molecules of the invention, or variants thereof, may be constructed using standard molecular biological techniques (e.g., recombinant DNA and protein expression technology), as will be known to a person of ordinary skill in the art.

In some embodiments, NPR1-specific antibodies are generated in a bi-specific format (a "bi-specific") in which variable regions binding to distinct domains of NPR1 protein are linked together to confer dual-domain specificity within a single binding molecule. Appropriately designed bi-specifics may enhance overall NPR1-protein inhibitory efficacy through increasing both specificity and binding avidity. Variable regions with specificity for individual domains, (e.g., segments of the N-terminal domain), or that can bind to different regions within one domain, are paired on a structural scaffold that allows each region to bind simultaneously to the separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, US2011/0195454 and US2010/0331527).

Alternatively, antibodies that bind more than one domains and a second target, such as, but not limited to, for example, a second different anti-NPR1 antibody, may be prepared in a bi-specific format using techniques described herein, or other techniques known to those skilled in the art. Antibody variable regions binding to distinct regions may be linked together with variable regions that bind to relevant sites on, for example, the extracellular domain of NPR1, to confer dual-antigen specificity within a single binding molecule. Appropriately designed bi-specifics of this nature serve a dual function. Variable regions with specificity for the extracellular domain are combined with a variable region with specificity for outside the extracellular domain and are paired on a structural scaffold that allows each variable region to bind to the separate antigens.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-NPR1 antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 100 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 600 mg, about 5 to about 500 mg, or about 10 to about 400 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles may be developed and conjugated to antibodies contained in pharmaceutical compositions to target cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracranial, intraperitoneal and intramuscular injections, drip infusions, etc. These injectable preparations may be prepared by methods publicly known.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antibody contained is generally about 5 to about 500 mg per dosage form in a unit dose; especially in the form of injection, it is preferred that the antibody is contained in about 5 to about 300 mg and in about 10 to about 300 mg for the other dosage forms.

Therapeutic Uses of the Antibodies

The antibodies of the present invention are useful for the treatment, and/or prevention of a disease or disorder or condition associated with NPR1 and/or for ameliorating at least one symptom associated with such disease, disorder or condition. In certain embodiments, an antibody or antigen-binding fragment thereof of the invention may be administered at a therapeutic dose to a patient with a disease or disorder or condition associated with NPR1.

In certain embodiments, the antibodies of the present invention are useful for treating or preventing at least one symptom or indication of a NPR1-associated disease or disorder selected from the group consisting of hypertension, heart failure, obesity, renal failure, chronic kidney disease, macular edema, glaucoma, stroke, lung disorders, pulmonary fibrosis, inflammation, asthma, skeletal growth disorders, bone fractures, diabetes, and cancer.

It is also contemplated herein to use one or more antibodies of the present invention prophylactically to subjects at risk for suffering from a NPR1-associated disease or disorder.

In one embodiment of the invention, the present antibodies are used for the preparation of a pharmaceutical composition or medicament for treating patients suffering from a disease, disorder or condition disclosed herein. In another embodiment of the invention, the present antibodies are used as adjunct therapy with any other agent or any other therapy known to those skilled in the art useful for treating or ameliorating a disease, disorder or condition disclosed herein.

Combination Therapies

Combination therapies may include an antibody of the invention and any additional therapeutic agent that may be advantageously combined with an antibody of the invention, or with a biologically active fragment of an antibody of the invention. The antibodies of the present invention may be combined synergistically with one or more drugs or therapy used to treat a NPR1-associated disease or disorder. In some embodiments, the antibodies of the invention may be combined with a second therapeutic agent to ameliorate one or more symptoms of said disease or condition.

Depending upon the disease, disorder or condition, the antibodies of the present invention may be used in combination with one or more additional therapeutic agents including, but not limited to, an aldosterone antagonist (e.g., eplerenone, spironolactone), an alpha-adrenergic blocker (e.g., doxazosin, phenoxybenzamine, phentolamine, prazosin, terazosin), an angiotensin converting enzyme (ACE)

inhibitor (e.g., benazepril, captopril, enalapril, fosinopril, lisinopril, moexipril, perindopril, quinapril, ramipril, trandolapril), an arteriolar vasodilator (e.g., hydralazine, minoxidil), an autonomic ganglionic vasodilator (e.g., mecamylamine), a beta-adrenergic blocker (acebutolol, atenolol, betaxolol, bisoprolol, carvedilol, carteolol, esmolol, labetolol, metoprolol, nadolol, penbuterol, pindolol, propranolol, timolol), a catecholamine-depleting sympatholytic (e.g., deserpidine, reserpine), a central alpha-2 adrenergic agonist (e.g., clonidine, guanabenz, guanfacine, methyldopa), a calcium channel blocker (diltiazem, verapamil, amlodipine, felodipine, isradipine, nicadipine, nifedipine, nisoldipine), a diuretic (e.g., bumetanide, ethacrynic acid, furoseamide, torsemide, chlorothiazide, hydrochlorothiazide, hydroflumethiazide, methyclothiazide, polythiazide, chlorthalidone, indapamide, metolazone), a renin inhibitor (e.g., aliskiren), an anti-coagulant (e.g., coumardin, dabigatran, apixaban), an anti-platelet agent (e.g., aspirin, clopidogrel), a cholesterol lowering agent (e.g., a statin, a PCSK9 inhibitor such as alirocumab), a vasodilator (e.g., minoxidil, hydralazine, nitrates), digitalis, surgery (e.g., angioplasty, coronary artery bypass, heart transplant), an implantable device (e.g., valve replacement, defibrillator device, left ventricular assist device, pacemaker), anti-tumor therapy (e.g., a chemotherapeutic agent, surgery, radiation, a PD-1 inhibitor), insulin, a GLP1 agonist (e.g., exenatide, liraglutide, lixisenatide, albiglutide, dulaglutide, semaglutide), metformin, dialysis, bone marrow stimulant, hemofiltration, a lifestyle modification, and a dietary supplement.

As used herein, the term "in combination with" means that additional therapeutically active component(s) may be administered prior to, concurrent with, or after the administration of the anti-NPR1 antibody of the present invention. The term "in combination with" also includes sequential or concomitant administration of an anti-NPR1 antibody and a second therapeutic agent.

The additional therapeutically active component(s) may be administered to a subject prior to administration of an anti-NPR1 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, or less than 30 minutes before administration of the second component. In other embodiments, the additional therapeutically active component(s) may be administered to a subject after administration of an anti-NPR1 antibody of the present invention. For example, a first component may be deemed to be administered "after" a second component if the first component is administered 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after or more after administration of the second component. In yet other embodiments, the additional therapeutically active component(s) may be administered to a subject concurrent with administration of an anti-NPR1 antibody of the present invention. "Concurrent" administration, for purposes of the present invention, includes, e.g., administration of an anti-NPR1 antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-NPR1 antibody and the additional therapeutically active component may be administered intravenously, etc.); alternatively, each dosage form may be administered via a different route (e.g., the anti-NPR1 antibody may be administered intravenously, and the additional therapeutically active component may be administered orally). In any event, administering the components in a single dosage from, in separate dosage forms by the same route, or in separate dosage forms by different routes are all considered "concurrent administration," for purposes of the present disclosure. For purposes of the present disclosure, administration of an anti-NPR1 antibody "prior to", "concurrent with," or "after" (as those terms are defined herein above) administration of an additional therapeutically active component is considered administration of an anti-NPR1 antibody "in combination with" an additional therapeutically active component.

The present invention includes pharmaceutical compositions in which an anti-NPR1 antibody of the present invention is co-formulated with one or more of the additional therapeutically active component(s) as described elsewhere herein.

Diagnostic Uses of the Antibodies

The antibodies of the present invention may be used to detect and/or measure NPR1 in a sample, e.g., for diagnostic purposes. Some embodiments contemplate the use of one or more antibodies of the present invention in assays to detect a NPR1-associated-disease or disorder. Exemplary diagnostic assays for NPR1 may comprise, e.g., contacting a sample, obtained from a patient, with an anti-NPR1 antibody of the invention, wherein the anti-NPR1 antibody is labeled with a detectable label or reporter molecule or used as a capture ligand to selectively isolate NPR1 from patient samples. Alternatively, an unlabeled anti-NPR1 antibody can be used in diagnostic applications in combination with a secondary antibody which is itself detectably labeled. The detectable label or reporter molecule can be a radioisotope, such as $^3$H, $^{14}$C $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure NPR1 in a sample include enzyme-linked immunosorbent assay (ELISA), radioimmunoassay (RIA), and fluorescence-activated cell sorting (FACS).

Samples that can be used in NPR1 diagnostic assays according to the present invention include any tissue or fluid sample obtainable from a patient, which contains detectable quantities of either NPR1 protein, or fragments thereof, under normal or pathological conditions. Generally, levels of NPR1 protein in a particular sample obtained from a healthy patient (e.g., a patient not afflicted with a disease associated with NPR1) will be measured to initially establish a baseline, or standard, level of NPR1. This baseline level of NPR1 can then be compared against the levels of NPR1 measured in samples obtained from individuals suspected of having a NPR1-associated condition, or symptoms associated with such condition.

The antibodies specific for NPR1 protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to Natriuretic Peptide Receptor 1 (NPR1)

Human antibodies to NPR1 protein were generated in a VELOCIMMUNE® mouse comprising DNA encoding human Immunoglobulin heavy and kappa light chain variable regions. The mice were immunized with human NPR1 and mouse ANP DNA by hydrodynamic DNA delivery and boosted by extracellular domain of human NPR1 protein complexed to mouse ANP.

The antibody immune response was monitored by a NPR1-specific immunoassay. When a desired immune response was achieved, splenocytes were harvested and fused with mouse myeloma cells to preserve their viability and form hybridoma cell lines. The hybridoma cell lines were screened and selected to identify cell lines that produce NPR1-specific antibodies. The cell lines were used to obtain several anti-NPR1 chimeric antibodies (i.e., antibodies possessing human variable domains and mouse constant domains).

Anti-NPR1 antibodies were also isolated directly from antigen-positive mouse B cells without fusion to myeloma cells, as described in U.S. Pat. No. 7,582,298, herein specifically incorporated by reference in its entirety. Using this method, several fully human anti-NPR1 antibodies (i.e., antibodies possessing human variable domains and human constant domains) were obtained.

Exemplary antibodies generated as disclosed above were designated as mAb22033, mAb22035, mAb22805, mAb22809, mAb22810, mAb25479, mAb25491, mAb25497, mAb25498, mAb25502, mAb25508, and mAb25545.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-NPR1 antibodies of the invention.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb22033 | 2 | 4 | 6 | 8 | 10 | 12 | 14 | 16 |
| mAb22035 | 18 | 20 | 22 | 24 | 26 | 28 | 30 | 32 |
| mAb22805 | 34 | 36 | 38 | 40 | 42 | 44 | 46 | 48 |
| mAb22809 | 50 | 52 | 54 | 56 | 58 | 60 | 62 | 64 |
| mAb22810 | 66 | 68 | 70 | 72 | 74 | 76 | 78 | 80 |
| mAb25479 | 82 | 84 | 86 | 88 | 90 | 92 | 94 | 96 |
| mAb25491 | 98 | 100 | 102 | 104 | 106 | 108 | 110 | 112 |
| mAb25497 | 114 | 116 | 118 | 120 | 122 | 124 | 126 | 128 |
| mAb25498 | 130 | 132 | 134 | 136 | 138 | 140 | 142 | 144 |
| mAb25502 | 146 | 148 | 150 | 152 | 154 | 156 | 158 | 160 |
| mAb25508 | 162 | 164 | 166 | 168 | 170 | 172 | 174 | 176 |
| mAb25545 | 178 | 180 | 182 | 184 | 186 | 188 | 190 | 192 |

The corresponding nucleic acid sequence identifiers are set forth in Table 2.

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb22033 | 1 | 3 | 5 | 7 | 9 | 11 | 13 | 15 |
| mAb22035 | 17 | 19 | 21 | 23 | 25 | 27 | 29 | 31 |
| mAb22805 | 33 | 35 | 37 | 39 | 41 | 43 | 45 | 47 |
| mAb22809 | 49 | 51 | 53 | 55 | 57 | 59 | 61 | 63 |
| mAb22810 | 65 | 67 | 69 | 71 | 73 | 75 | 77 | 79 |
| mAb25479 | 81 | 83 | 85 | 87 | 89 | 91 | 93 | 95 |
| mAb25491 | 97 | 99 | 101 | 103 | 105 | 107 | 109 | 111 |
| mAb25497 | 113 | 115 | 117 | 119 | 121 | 123 | 125 | 127 |

TABLE 2-continued

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| mAb25498 | 129 | 131 | 133 | 135 | 137 | 139 | 141 | 143 |
| mAb25502 | 145 | 147 | 149 | 151 | 153 | 155 | 157 | 159 |
| mAb25508 | 161 | 163 | 165 | 167 | 169 | 171 | 173 | 175 |
| mAb25545 | 177 | 179 | 181 | 183 | 185 | 187 | 189 | 191 |

Antibodies referred to herein typically have fully human variable regions, but may have human or mouse constant regions. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 2—will remain the same, and the binding properties to antigen are expected to be identical or substantially similar regardless of the nature of the Fc domain. In certain embodiments, selected antibodies with a mouse IgG1 Fc are converted to antibodies with human IgG4 Fc. In one embodiment, the IgG4 Fc domain comprises 2 or more amino acid changes as disclosed in US20100331527. In one embodiment, the human IgG4 Fc comprises a serine to proline mutation in the hinge region (S108P) to promote dimer stabilization. Unless indicated otherwise, all antibodies used in the following examples comprise a human IgG4 isotype.

Control Constructs used in the Following Examples

The following control construct (anti-NPR1 antibodies) was included in the experiments disclosed herein, for comparative purposes: "Comparator 1," a monoclonal antibody against human NPR1 having $V_H/V_L$ sequences of antibody "mAb5591" according to US Patent No. 20120114659 (Morphosys).

Example 3: Antibody Binding to NPR1 as Determined by Surface Plasmon Resonance Experimental Procedure Equilibrium dissociation constant ($K_D$) for different NPR1 reagents binding to purified anti-NPR1 monoclonal antibodies (mAbs) were determined using a real-time surface plasmon resonance based Biacore 4000 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with either mouse anti-human Fc specific mAb (GE Healthcare, # BR100839) or goat anti-human Fcγ specific polyclonal antibody (Jackson ImmunoResearch Laboratories, # BR-1008-39) to capture anti-NPR1 mAbs. Binding studies were performed on human NPR1 extracellular domain expressed with a C-terminal myc-myc-hexahistidine (hNPR1-MMH) (SEQ ID NO: 194), monkey NPR1 extracellular domain expressed with a C-terminal myc-myc-hexahistidine (mfNPR1-MMH) (SEQ ID NO: 195), mouse NPR1 extracellular domain expressed with a C-terminal myc-myc-hexahistidine (mNPR1-MMH) (SEQ ID NO: 196), human NPR1 extracellular domain expressed with a C-terminal mouse IgG2a (hNPR1-mFc) (SEQ ID NO: 197), monkey NPR1 extracellular domain expressed with a C-terminal mouse IgG2a (mfNPR1-mFc) (SEQ ID NO: 198), mouse NPR1 extracellular domain expressed with a C-terminal mouse IgG2a (mNPR1-mFc) (SEQ ID NO: 199), hNPR1-mFc+hANP, hNPR1-mFc+hBNP, mfNPR1-mFc+hANP, mfNPR1-mFc+hBNP, mNPR1-mFc+mANP, mNPR1-mFc'mBNP. Different concentrations of hNPR1-MMH, mfNPR1-MMH (100 nM-3.7 nM, 3-fold serial dilution or 100 nM-6.25 nM, 4-fold serial dilution); hNPR1-mFc, mfNPR1.mFc (100 nM-1.56 nM, 4-fold serial dilution or 100 nM -3.7 nM, 3-fold serial dilution); mNPR1.mmh (100 nM), hNPR1-mFc or mfNPR1-mFc complexed with 10-fold concentration of hANP or hBNP (100 nM, 25 nM, 6.25 nM or 100 nM-3.7 nM, 3-fold serial dilution); mNPR1.mFc complexed with 10-fold concentration of mANP or mBNP (100 nM, 25 nM or 100 nM-3.7 nM, 3-fold serial dilution) or hNPR1-hFc or hNPR1-hFc complexed with 10-fold concentration of hANP (100 nM-6.25 nM, 4-fold serial dilution) prepared in HBS-ET running buffer, were injected for 4 minutes at a flow rate of 30 μL/min while the dissociation of mAb bound different NPR1 reagents was monitored for 10 minutes in HBS-ET running buffer. At the end of each cycle, the NPR1 mAb capture surface was regenerated using either 10 sec injection of 20 mM phosphoric acid for mouse anti-human Fc specific mAb surface or 40 sec injection of 10 mM Glycine, HCl, pH1.5 for goat anti-human Fcγ specific polyclonal antibody or two 1-minute injections of 10 mM Gly pH1.5. The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60 * kd}$$

Results

Binding kinetics parameters for different NPR1 proteins binding to selected anti-NPR1 antibodies of the invention at 25° C. and 37° C. are shown in Tables 3 through 26.

TABLE 3

Binding kinetics parameters of hNPR1-MMH binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 377 ± 0.9 | 30 | 8.55E+03 | 4.06E−04 | 4.75E−08 | 28.4 |
| mAb22035 | 368 ± 0.6 | 210 | 2.03E+05 | 1.50E−04 | 7.38E−10 | 77.3 |
| mAb22805 | 356 ± 0.7 | 0 | NB$ | NB$ | NB$ | NB$ |
| mAb22809 | 359 ± 1.1 | 0 | NB$ | NB$ | NB$ | NB$ |
| mAb22810 | 386 ± 3.8 | 1 | NB$ | NB$ | NB$ | NB$ |
| mAb25479 | 338 ± 1.2 | 16 | 1.40E+04 | 6.73E−03 | 4.82E−07 | 1.7 |
| mAb25491 | 275 ± 0.9 | 37 | 2.62E+04 | 9.83E−04 | 3.76E−08 | 11.7 |
| mAb25497 | 314 ± 0.6 | 22 | 3.17E+04 | 1.67E−03 | 5.27E−08 | 6.9 |
| mAb25498 | 325 ± 0.8 | 68 | 2.25E+04 | 1.82E−03 | 8.10E−08 | 6.3 |
| mAb25502 | 349 ± 2.3 | 2 | NB$ | NB$ | NB$ | NB$ |
| mAb25508 | 296 ± 1 | 192 | 4.32E+05 | 1.34E−04 | 3.09E−10 | 86.5 |
| mAb25545 | 360 ± 0.7 | 2 | NB$ | NB$ | NB$ | NB$ |
| IgG4 Isotype Control | 315 ± 0.7 | 1 | NB$ | NB$ | NB$ | NB$ |

$indicates that no binding was observed under the current experimental conditions
*indicates that the observed binding data were inconclusive

TABLE 4

Binding kinetics parameters of hNPR1-MMH binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 473 ± 2.1 | 52 | 6.03E+03 | 8.19E−04 | 1.36E−07 | 14.1 |
| mAb22035 | 492 ± 2.3 | 284 | 2.40E+05 | 3.12E−04 | 1.30E−09 | 37.1 |
| mAb22805 | 451 ± 2 | 1 | NB$ | NB$ | NB$ | NB$ |
| mAb22809 | 466 ± 2 | −1 | NB$ | NB$ | NB$ | NB$ |
| mAb22810 | 428 ± 1.2 | 1 | NB$ | NB$ | NB$ | NB$ |
| mAb25479 | 443 ± 4.5 | 16 | 2.28E+04 | 1.57E−02 | 6.89E−07 | 0.7 |
| mAb25491 | 357 ± 1.8 | 51 | 3.56E+04 | 4.53E−03 | 1.27E−07 | 2.5 |
| mAb25497 | 402 ± 3 | 31 | 1.86E+04 | 2.58E−03 | 1.39E−07 | 4.5 |
| mAb25498 | 418 ± 2.8 | 97 | 2.25E+04 | 4.15E−03 | 1.84E−07 | 2.8 |
| mAb25502 | 452 ± 3.3 | 4 | NB$ | NB$ | NB$ | NB$ |
| mAb25508 | 397 ± 2.1 | 252 | 4.53E+05 | 2.22E−04 | 4.90E−10 | 52.1 |
| mAb25545 | 463 ± 1.7 | 7 | IC* | IC* | IC* | IC* |
| IgG4 Isotype Control | 417 ± 3.1 | 3 | NB$ | NB$ | NB$ | NB$ |

$indicates that no binding was observed under the current experimental conditions
*indicates that the observed binding data were inconclusive

TABLE 5

Binding kinetics parameters of mfNPR1-MMH binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 376 ± 0.8 | 79 | 1.79E+04 | 2.91E−04 | 1.62E−08 | 39.6 |
| mAb22035 | 368 ± 0.8 | 245 | 4.26E+05 | 1.43E−04 | 3.36E−10 | 80.8 |
| mAb22805 | 356 ± 1.1 | 0 | NB$ | NB$ | NB$ | NB$ |
| mAb22809 | 359 ± 0.9 | 0 | NB$ | NB$ | NB$ | NB$ |
| mAb22810 | 381 ± 0.8 | 1 | NB$ | NB$ | NB$ | NB$ |
| mAb25479 | 338 ± 0.5 | 41 | 2.77E+04 | 6.82E−03 | 2.46E−07 | 1.7 |
| mAb25491 | 275 ± 0.4 | 81 | 4.20E+04 | 1.28E−03 | 3.05E−08 | 9.0 |
| mAb25497 | 315 ± 0.6 | 49 | 3.78E+04 | 2.26E−03 | 5.98E−08 | 5.1 |
| mAb25498 | 327 ± 0.5 | 114 | 5.79E+04 | 1.58E−03 | 2.72E−08 | 7.3 |
| mAb25502 | 350 ± 0.9 | 3 | NB$ | NB$ | NB$ | NB$ |
| mAb25508 | 298 ± 1.1 | 213 | 7.06E+05 | 1.32E−04 | 1.87E−10 | 87.5 |
| mAb25545 | 360 ± 0.5 | 4 | IC* | IC* | IC* | IC* |
| IgG4 Isotype Control | 315 ± 0.6 | 0 | NB$ | NB$ | NB$ | NB$ |

$indicates that no binding was observed under the current experimental conditions
*indicates that the observed binding data were inconclusive

TABLE 6

Binding kinetics parameters of mfNPR1-MMH binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 470 ± 1.4 | 131 | 2.51E+04 | 6.97E−04 | 2.78E−08 | 16.6 |
| mAb22035 | 490 ± 1.3 | 319 | 5.32E+05 | 3.74E−04 | 7.02E−10 | 30.9 |
| mAb22805 | 449 ± 1.3 | 3 | NB$ | NB$ | NB$ | NB$ |
| mAb22809 | 465 ± 1 | 1 | NB$ | NB$ | NB$ | NB$ |
| mAb22810 | 426 ± 1.1 | 0 | NB$ | NB$ | NB$ | NB$ |
| mAb25479 | 440 ± 1.8 | 43 | 3.96E+04 | 1.42E−02 | 3.60E−07 | 0.8 |
| mAb25491 | 353 ± 1.2 | 106 | 5.83E+04 | 4.57E−03 | 7.84E−08 | 2.5 |
| mAb25497 | 397 ± 1.4 | 69 | 2.77E+04 | 3.84E−03 | 1.39E−07 | 3.0 |
| mAb25498 | 414 ± 1.7 | 151 | 7.07E+04 | 3.69E−03 | 5.21E−08 | 3.1 |
| mAb25502 | 449 ± 1.7 | 6 | NB$ | NB$ | NB$ | NB$ |
| mAb25508 | 394 ± 1.1 | 275 | 7.82E+05 | 2.73E−04 | 3.49E−10 | 42.3 |
| mAb25545 | 461 ± 1 | 10 | IC* | IC* | IC* | IC* |
| IgG4 Isotype Control | 413 ± 1.3 | 3 | NB$ | NB$ | NB$ | NB$ |

$indicates that no binding was observed under the current experimental conditions
*indicates that the observed binding data were inconclusive

TABLE 7

Binding kinetics parameters of mNPR1-MMH binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 376 ± 0.7 | 0 | NB$ | NB$ | NB$ | NB$ |
| mAb22035 | 368 ± 0.2 | 0 | NB$ | NB$ | NB$ | NB$ |
| mAb22805 | 358 ± 1.9 | 0 | NB$ | NB$ | NB$ | NB$ |
| mAb22809 | 358 ± 0.3 | 0 | NB$ | NB$ | NB$ | NB$ |
| mAb22810 | 378 ± 0.3 | −1 | NB$ | NB$ | NB$ | NB$ |
| mAb25479 | 338 ± 1.2 | 0 | NB$ | NB$ | NB$ | NB$ |
| mAb25491 | 276 ± 0.3 | 0 | NB$ | NB$ | NB$ | NB$ |
| mAb25497 | 315 ± 0.1 | 0 | NB$ | NB$ | NB$ | NB$ |
| mAb25498 | 326 ± 0.6 | 0 | NB$ | NB$ | NB$ | NB$ |
| mAb25502 | 349 ± 0.7 | 0 | NB$ | NB$ | NB$ | NB$ |
| mAb25508 | 296 ± 1.2 | 0 | NB$ | NB$ | NB$ | NB$ |
| mAb25545 | 359 ± 0.1 | 0 | NB$ | NB$ | NB$ | NB$ |
| IgG4 Isotype Control | 315 ± 0.1 | 0 | NB$ | NB$ | NB$ | NB$ |

$indicates that no binding was observed under the current experimental conditions
*indicates that the observed binding data were inconclusive
indicates that the conditions were not tested

TABLE 8

Binding kinetics parameters of mNPR1-MMH binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 468 ± 0.6 | 1 | NB$ | NB$ | NB$ | NB$ |
| mAb22035 | 491 ± 0.9 | 1 | NB$ | NB$ | NB$ | NB$ |
| mAb22805 | 450 ± 0.2 | 1 | NB$ | NB$ | NB$ | NB$ |
| mAb22809 | 466 ± 0.1 | 0 | NB$ | NB$ | NB$ | NB$ |
| mAb22810 | 420 ± 0.1 | −2 | NB$ | NB$ | NB$ | NB$ |
| mAb25479 | 438 ± 0.2 | 1 | NB$ | NB$ | NB$ | NB$ |
| mAb25491 | 353 ± 1.8 | 0 | NB$ | NB$ | NB$ | NB$ |
| mAb25497 | 395 ± 0.7 | 0 | NB$ | NB$ | NB$ | NB$ |
| mAb25498 | 413 ± 0.2 | 0 | NB$ | NB$ | NB$ | NB$ |
| mAb25502 | 447 ± 0.9 | 0 | NB$ | NB$ | NB$ | NB$ |
| mAb25508 | 392 ± 0.3 | 0 | NB$ | NB$ | NB$ | NB$ |
| mAb25545 | 460 ± 0.4 | 1 | NB$ | NB$ | NB$ | NB$ |
| IgG4 Isotype Control | 412 ± 0.4 | 1 | NB$ | NB$ | NB$ | NB$ |

$indicates that no binding was observed under the current experimental conditions
*indicates that the observed binding data were inconclusive
indicates that the conditions were not tested

TABLE 9

Binding kinetics parameters of hNPR1-mFc or hNPR1-hFc binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 351 ± 1.3 | 56 | 6.18E+04 | 6.38E−05 | 1.03E−09 | 181.0 |
| mAb22035 | 347 ± 1.2 | 198 | 2.25E+05 | 8.20E−05 | 3.65E−10 | 140.9 |
| mAb22805 | 331 ± 0.8 | 2 | NB$ | NB$ | NB$ | NB$ |
| mAb22809 | 327 ± 0.7 | −2 | NB$ | NB$ | NB$ | NB$ |
| mAb22810 | 380 ± 0.4 | 4 | IC* | IC* | IC* | IC* |
| mAb25479 | 327 ± 2.1 | 26 | 3.80E+04 | 8.52E−04 | 2.24E−08 | 13.6 |
| mAb25491 | 249 ± 2.8 | 36 | 1.01E+05 | 1.24E−04 | 1.24E−09 | 92.8 |
| mAb25497 | 302 ± 25.8 | 49 | 2.03E+05 | 4.83E−05 | 2.38E−10 | 239.3 |
| mAb25498 | 312 ± 0.8 | 94 | 6.98E+04 | 2.55E−04 | 3.65E−09 | 45.3 |
| mAb25502 | 321 ± 1.6 | 17 | 8.79E+04 | 8.74E−05 | 9.94E−10 | 132.1 |
| mAb25508 | 276 ± 1.5 | 211 | 7.89E+05 | 6.85E−05 | 8.68E−11 | 168.6 |

TABLE 9-continued

Binding kinetics parameters of hNPR1-mFc or hNPR1-hFc binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb25545 | 340 ± 1.1 | 7 | IC* | IC* | IC* | IC* |
| IgG4 Isotype Control | 298 ± 1.6 | −14 | NB$ | NB$ | NB$ | NB$ |

$indicates that no binding was observed under the current experimental conditions
*indicates that the observed binding data were inconclusive

TABLE 10

Binding kinetics parameters of hNPR1-mFc or hNPR1-hFc binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 423 ± 3.1 | 75 | 3.68E+04 | 1.31E−04 | 3.56E−09 | 88.2 |
| mAb22035 | 454 ± 3.6 | 257 | 6.36E+05 | 1.27E−04 | 2.00E−10 | 90.8 |
| mAb22805 | 406 ± 1.8 | 8 | NB$ | NB$ | NB$ | NB$ |
| mAb22809 | 413 ± 1.6 | −1 | NB$ | NB$ | NB$ | NB$ |
| mAb22810 | 423 ± 0.8 | 9 | IC* | IC* | IC* | IC* |
| mAb25479 | 414 ± 5.6 | 47 | 3.37E+04 | 1.39E−03 | 4.12E−08 | 8.3 |
| mAb25491 | 298 ± 1.6 | 70 | 4.19E+04 | 3.63E−04 | 8.66E−09 | 31.8 |
| mAb25497 | 344 ± 1.7 | 43 | 4.23E+04 | 3.10E−04 | 7.31E−09 | 37.3 |
| mAb25498 | 381 ± 2 | 129 | 8.86E+04 | 5.68E−04 | 6.41E−09 | 20.3 |
| mAb25502 | 396 ± 2.8 | 9 | NB$ | NB$ | NB$ | NB$ |
| mAb25508 | 353 ± 1.3 | 242 | 8.38E+05 | 1.01E−04 | 1.21E−10 | 113.9 |
| mAb25545 | 415 ± 2.8 | 15 | IC* | IC* | IC* | IC* |
| IgG4 Isotype Control | 366 ± 3.9 | −19 | NB$ | NB$ | NB$ | NB$ |

$indicates that no binding was observed under the current experimental conditions
*indicates that the observed binding data were inconclusive

TABLE 11

Binding kinetics parameters of hNPR1-mFc:hANP or hNPR1-hFc:hANP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 350 ± 0.4 | 84 | 6.03E+04 | 8.60E−05 | 1.43E−09 | 134.4 |
| mAb22035 | 347 ± 0.3 | 186 | 1.79E+05 | 7.78E−05 | 4.34E−10 | 148.4 |
| mAb22805 | 331 ± 1.8 | 84 | 4.31E+04 | 1.41E−04 | 3.28E−09 | 81.7 |
| mAb22809 | 327 ± 1.5 | 53 | 3.92E+04 | 1.93E−04 | 4.94E−09 | 59.7 |
| mAb22810 | 378 ± 0.6 | 14 | 8.31E+03 | 3.44E−04 | 4.14E−08 | 34 |
| mAb25479 | 327 ± 2.4 | 49 | 3.10E+04 | 1.09E−04 | 3.53E−09 | 105.8 |
| mAb25491 | 250 ± 1.7 | 71 | 5.22E+04 | 4.15E−05 | 7.94E−10 | 278.5 |
| mAb25497 | 292 ± 2.1 | 59 | 1.63E+05 | 4.56E−05 | 2.79E−10 | 253.1 |
| mAb25498 | 313 ± 0.6 | 52 | 4.58E+04 | 3.17E−04 | 6.93E−09 | 36.4 |
| mAb25502 | 321 ± 4.3 | 81 | 6.06E+04 | 2.53E−04 | 4.17E−09 | 45.7 |
| mAb25508 | 278 ± 4.2 | 199 | 2.64E+05 | 8.97E−05 | 3.40E−10 | 128.8 |
| mAb25545 | 341 ± 1.8 | 28 | 2.34E+04 | 4.63E−05 | 1.98E−09 | 249.7 |
| IgG4 Isotype Control | 297 ± 1.5 | −12 | NB$ | NB$ | NB$ | NB$ |

$indicates that no binding was observed under the current experimental conditions
*indicates that the observed binding data were inconclusive

TABLE 12

Binding kinetics parameters of hNPR1-mFc:hANP or hNPR1-hFc:hANP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 412 ± 1.2 | 108 | 5.79E+04 | 9.80E−05 | 1.69E−09 | 117.9 |
| mAb22035 | 444 ± 2 | 237 | 2.25E+05 | 1.14E−04 | 5.08E−10 | 101.0 |
| mAb22805 | 399 ± 1.9 | 113 | 6.01E+04 | 2.95E−04 | 4.91E−09 | 39.2 |
| mAb22809 | 406 ± 0.8 | 68 | 5.04E+04 | 1.66E−04 | 3.29E−09 | 69.5 |
| mAb22810 | 421 ± 0.8 | 26 | 1.37E+04 | 1.04E−03 | 7.55E−08 | 11 |
| mAb25479 | 408 ± 7.6 | 84 | 4.97E+04 | 1.34E−04 | 2.70E−09 | 86.1 |
| mAb25491 | 291 ± 1.3 | 96 | 5.69E+04 | 1.11E−04 | 1.95E−09 | 104.1 |
| mAb25497 | 336 ± 1.6 | 60 | 4.85E+04 | 1.02E−04 | 2.09E−09 | 113.7 |
| mAb25498 | 375 ± 1.9 | 74 | 5.30E+04 | 7.20E−04 | 1.36E−08 | 16.0 |
| mAb25502 | 388 ± 5.1 | 105 | 7.20E+04 | 4.67E−04 | 6.49E−09 | 24.7 |
| mAb25508 | 348 ± 0.8 | 230 | 2.93E+05 | 1.48E−04 | 5.06E−10 | 77.9 |
| mAb25545 | 409 ± 2.7 | 58 | 3.67E+04 | 8.61E−05 | 2.35E−09 | 134.2 |
| IgG4 Isotype Control | 358 ± 4.9 | −18 | NB$ | NB$ | NB$ | NB$ |

$indicates that no binding was observed under the current experimental conditions
*indicates that the observed binding data were inconclusive

TABLE 13

Binding kinetics parameters of hNPR1-mFc:hBNP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 350 ± 0.4 | 85 | 5.43E+04 | 6.67E−05 | 1.23E−09 | 173.2 |
| mAb22035 | 348 ± 2.9 | 194 | 1.71E+05 | 8.70E−05 | 5.08E−10 | 132.7 |
| mAb22805 | 330 ± 0.4 | 84 | 4.14E+04 | 1.52E−04 | 3.68E−09 | 75.8 |
| mAb22809 | 327 ± 0.4 | 51 | 3.28E+04 | 2.21E−04 | 6.72E−09 | 52.4 |
| mAb22810 | NT# | NT# | NT# | NT# | NT# | NT# |
| mAb25479 | 326 ± 0.5 | 50 | 2.92E+04 | 1.23E−04 | 4.21E−09 | 94.1 |
| mAb25491 | 250 ± 0.3 | 72 | 5.46E+04 | 4.96E−05 | 9.08E−10 | 232.9 |
| mAb25497 | 292 ± 0.4 | 59 | 1.53E+05 | 5.49E−05 | 3.58E−10 | 210.5 |
| mAb25498 | 313 ± 0.4 | 55 | 4.85E+04 | 2.56E−04 | 5.28E−09 | 45.1 |
| mAb25502 | 317 ± 1.5 | 78 | 6.94E+04 | 2.36E−04 | 3.40E−09 | 49.0 |
| mAb25508 | 275 ± 0.6 | 200 | 2.50E+05 | 8.57E−05 | 3.43E−10 | 134.7 |
| mAb25545 | 340 ± 0.2 | 27 | 2.30E+04 | 6.26E−05 | 2.72E−09 | 184.6 |
| IgG4 Isotype Control | 296 ± 0.5 | −11 | NB$ | NB$ | NB$ | NB$ |

$indicates that no binding was observed under the current experimental conditions
*indicates that the observed binding data were inconclusive
indicates that the conditions were not tested

TABLE 14

Binding kinetics parameters of hNPR1-mFc:hBNP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 409 ± 1.4 | 108 | 5.37E+04 | 9.60E−05 | 1.79E−09 | 120.3 |
| mAb22035 | 440 ± 0.8 | 243 | 2.32E+05 | 1.28E−04 | 5.53E−10 | 90.0 |
| mAb22805 | 398 ± 1.4 | 112 | 5.20E+04 | 3.13E−04 | 6.02E−09 | 36.9 |
| mAb22809 | 405 ± 0.5 | 63 | 4.65E+04 | 1.66E−04 | 3.56E−09 | 69.8 |
| mAb22810 | NT# | NT# | NT# | NT# | NT# | NT# |
| mAb25479 | 402 ± 0.4 | 85 | 4.27E+04 | 1.63E−04 | 3.83E−09 | 70.7 |
| mAb25491 | 289 ± 1.5 | 96 | 5.47E+04 | 1.34E−04 | 2.45E−09 | 86.2 |
| mAb25497 | 333 ± 1.1 | 59 | 4.92E+04 | 1.16E−04 | 2.35E−09 | 99.7 |
| mAb25498 | 372 ± 0.9 | 76 | 5.29E+04 | 9.48E−04 | 1.79E−08 | 12.2 |
| mAb25502 | 391 ± 0.7 | 102 | 6.03E+04 | 4.72E−04 | 7.82E−09 | 24.5 |
| mAb25508 | 347 ± 0.9 | 236 | 3.52E+05 | 1.64E−04 | 4.66E−10 | 70.3 |

TABLE 14-continued

Binding kinetics parameters of hNPR1-mFc:hBNP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb25545 | 405 ± 1.2 | 56 | 3.46E+04 | 9.84E-05 | 2.85E-09 | 117.3 |
| IgG4 Isotype Control | 354 ± 0.4 | -17 | NB$ | NB$ | NB$ | NB$ |

$indicates that no binding was observed under the current experimental conditions
*indicates that the observed binding data were inconclusive
indicates that the conditions were not tested

TABLE 15

Binding kinetics parameters of mfNPR1-mFc binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 351 ± 0.7 | 96 | 5.17E+04 | 4.85E-05 | 9.38E-10 | 238.0 |
| mAb22035 | 346 ± 0.6 | 231 | 2.44E+05 | 5.57E-05 | 2.29E-10 | 207.2 |
| mAb22805 | 331 ± 1.6 | 10 | IC* | IC* | IC* | IC* |
| mAb22809 | 328 ± 0.7 | 6 | NB$ | NB$ | NB$ | NB$ |
| mAb22810 | NT# | NT# | NT# | NT# | NT# | NT# |
| mAb25479 | 325 ± 0.7 | 54 | 3.12E+04 | 5.07E-04 | 1.62E-08 | 22.8 |
| mAb25491 | 251 ± 1.4 | 81 | 5.40E+04 | 7.54E-05 | 1.40E-09 | 153.1 |
| mAb25497 | 292 ± 1 | 76 | 1.72E+05 | 5.79E-05 | 3.37E-10 | 199.4 |
| mAb25498 | 313 ± 0.6 | 128 | 7.20E+04 | 1.77E-04 | 2.45E-09 | 65.4 |
| mAb25502 | 321 ± 1.9 | 22 | 8.83E+04 | 1.41E-04 | 1.60E-09 | 82.0 |
| mAb25508 | 276 ± 0.9 | 230 | 5.15E+05 | 5.98E-05 | 1.16E-10 | 193.3 |
| mAb25545 | 340 ± 0.7 | 13 | IC* | IC* | IC* | IC* |
| IgG4 Isotype Control | 297 ± 0.6 | 5 | NB$ | NB$ | NB$ | NB$ |

$indicates that no binding was observed under the current experimental conditions
*indicates that the observed binding data were inconclusive
indicates that the conditions were not tested

TABLE 16

Binding kinetics parameters of mfNPR1-mFc binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 415 ± 1.3 | 126 | 4.82E+04 | 9.90E-05 | 2.06E-09 | 116.7 |
| mAb22035 | 447 ± 1.5 | 291 | 4.59E+05 | 8.44E-05 | 1.84E-10 | 136.9 |
| mAb22805 | 402 ± 1.7 | 16 | IC* | IC* | IC* | IC* |
| mAb22809 | 409 ± 1.6 | 8 | NB$ | NB$ | NB$ | NB$ |
| mAb22810 | NT# | NT# | NT# | NT# | NT# | NT# |
| mAb25479 | 408 ± 1.3 | 89 | 3.82E+04 | 1.08E-03 | 2.81E-08 | 10.7 |
| mAb25491 | 294 ± 1.6 | 114 | 4.70E+04 | 1.64E-04 | 3.49E-09 | 70.4 |
| mAb25497 | 340 ± 1.1 | 79 | 4.25E+04 | 2.21E-04 | 5.20E-09 | 52.3 |
| mAb25498 | 377 ± 1.4 | 170 | 9.16E+04 | 3.72E-04 | 4.06E-09 | 31.1 |
| mAb25502 | 393 ± 1.7 | 17 | IC* | IC* | IC* | IC* |
| mAb25508 | 350 ± 1.1 | 268 | 6.34E+05 | 8.36E-05 | 1.32E-10 | 138.2 |
| mAb25545 | 410 ± 1 | 26 | 5.51E+04 | 1.44E-04 | 2.62E-09 | 80.0 |
| IgG4 Isotype Control | 360 ± 1.4 | 8 | NB$ | NB$ | NB$ | NB$ |

$indicates that no binding was observed under the current experimental conditions
*indicates that the observed binding data were inconclusive
indicates that the conditions were not tested

TABLE 17

Binding kinetics parameters of mfNPR1-mFc:hANP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 349 ± 0.5 | 133 | 6.58E+04 | 5.36E−05 | 8.15E−10 | 215.5 |
| mAb22035 | 346 ± 0.7 | 227 | 1.89E+05 | 4.66E−05 | 2.46E−10 | 247.9 |
| mAb22805 | 330 ± 0.5 | 116 | 4.84E+04 | 9.51E−05 | 1.96E−09 | 121.4 |
| mAb22809 | 327 ± 0.5 | 86 | 4.47E+04 | 1.73E−04 | 3.88E−09 | 66.6 |
| mAb22810 | NT# | NT# | NT# | NT# | NT# | NT# |
| mAb25479 | 326 ± 0.3 | 86 | 4.20E+04 | 1.03E−04 | 2.44E−09 | 112.7 |
| mAb25491 | 250 ± 0.8 | 111 | 6.01E+04 | 4.55E−05 | 7.57E−10 | 253.8 |
| mAb25497 | 292 ± 0.6 | 95 | 1.56E+05 | 3.75E−05 | 2.40E−10 | 307.7 |
| mAb25498 | 313 ± 0.4 | 81 | 4.19E+04 | 1.12E−04 | 2.68E−09 | 102.9 |
| mAb25502 | 316 ± 2.7 | 113 | 7.40E+04 | 2.64E−04 | 3.56E−09 | 43.8 |
| mAb25508 | 273 ± 0.5 | 224 | 3.14E+05 | 7.32E−05 | 2.33E−10 | 157.7 |
| mAb25545 | 339 ± 0.4 | 45 | 2.28E+04 | 5.37E−05 | 2.35E−09 | 215.1 |
| IgG4 Isotype Control | 296 ± 0.5 | 7 | NB$ | NB$ | NB$ | NB$ |

$indicates that no binding was observed under the current experimental conditions
*indicates that the observed binding data were inconclusive
indicates that the conditions were not tested

TABLE 18

Binding kinetics parameters of mfNPR1-mFc:hANP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 407 ± 1.1 | 169 | 6.80E+04 | 8.90E−05 | 1.31E−09 | 129.8 |
| mAb22035 | 438 ± 0.6 | 283 | 2.55E+05 | 7.70E−05 | 3.02E−10 | 150.1 |
| mAb22805 | 395 ± 0.3 | 153 | 6.33E+04 | 2.09E−04 | 3.30E−09 | 55.3 |
| mAb22809 | 403 ± 0.4 | 106 | 5.55E+04 | 2.05E−04 | 3.70E−09 | 56.2 |
| mAb22810 | NT# | NT# | NT# | NT# | NT# | NT# |
| mAb25479 | 401 ± 1.6 | 138 | 5.47E+04 | 2.19E−04 | 4.00E−09 | 52.8 |
| mAb25491 | 288 ± 1 | 148 | 7.10E+04 | 1.06E−04 | 1.49E−09 | 109.0 |
| mAb25497 | 332 ± 0.6 | 102 | 5.84E+04 | 1.52E−04 | 2.60E−09 | 75.9 |
| mAb25498 | 370 ± 1.5 | 114 | 5.01E+04 | 4.45E−04 | 8.89E−09 | 25.9 |
| mAb25502 | 390 ± 0.7 | 143 | 9.10E+04 | 5.24E−04 | 5.76E−09 | 22.0 |
| mAb25508 | 346 ± 0.3 | 262 | 4.11E+05 | 1.46E−04 | 3.55E−10 | 79.3 |
| mAb25545 | 404 ± 1.2 | 86 | 4.01E+04 | 8.18E−05 | 2.04E−09 | 141.2 |
| IgG4 Isotype Control | 353 ± 0.8 | 9 | NB$ | NB$ | NB$ | NB$ |

$indicates that no binding was observed under the current experimental conditions
*indicates that the observed binding data were inconclusive
indicates that the conditions were not tested

TABLE 19

Binding kinetics parameters of mfNPR1-mFc:hBNP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 349 ± 0.7 | 132 | 6.59E+04 | 5.15E−05 | 7.81E−10 | 224.2 |
| mAb22035 | 346 ± 0.3 | 231 | 2.05E+05 | 6.13E−05 | 3.00E−10 | 188.3 |
| mAb22805 | 330 ± 1.5 | 113 | 4.53E+04 | 9.60E−05 | 2.12E−09 | 120.4 |
| mAb22809 | 327 ± 0.6 | 80 | 4.14E+04 | 1.60E−04 | 3.85E−09 | 72.4 |
| mAb22810 | NT# | NT# | NT# | NT# | NT# | NT# |
| mAb25479 | 325 ± 0.1 | 86 | 3.81E+04 | 1.13E−04 | 2.95E−09 | 102.6 |
| mAb25491 | 249 ± 0.7 | 110 | 5.86E+04 | 3.71E−05 | 6.32E−10 | 311.7 |
| mAb25497 | 291 ± 0.1 | 93 | 1.40E+05 | 4.47E−05 | 3.20E−10 | 258.4 |
| mAb25498 | 312 ± 0.6 | 81 | 4.32E+04 | 1.09E−04 | 2.53E−09 | 106.0 |
| mAb25502 | 314 ± 3.4 | 110 | 6.90E+04 | 2.82E−04 | 4.08E−09 | 41.0 |
| mAb25508 | 273 ± 0.8 | 229 | 3.08E+05 | 8.91E−05 | 2.90E−10 | 129.6 |
| mAb25545 | 339 ± 0.1 | 42 | 2.39E+04 | 4.97E−05 | 2.08E−09 | 232.5 |

TABLE 19-continued

Binding kinetics parameters of mfNPR1-mFc:hBNP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | $t^{1/2}$ (min) |
|---|---|---|---|---|---|---|
| IgG4 Isotype Control | 296 ± 1.1 | 7 | NB$ | NB$ | NB$ | NB$ |

$indicates that no binding was observed under the current experimental conditions
*indicates that the observed binding data were inconclusive
indicates that the conditions were not tested

TABLE 20

Binding kinetics parameters of mfNPR1-mFc:hBNP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | $t^{1/2}$ (min) |
|---|---|---|---|---|---|---|
| mAb22033 | 406 ± 1.4 | 167 | 6.75E+04 | 8.80E−05 | 1.30E−09 | 131.3 |
| mAb22035 | 436 ± 1.1 | 286 | 2.58E+05 | 9.48E−05 | 3.68E−10 | 121.9 |
| mAb22805 | 394 ± 1 | 150 | 5.96E+04 | 2.02E−04 | 3.39E−09 | 57.2 |
| mAb22809 | 402 ± 0.9 | 99 | 5.34E+04 | 2.29E−04 | 4.29E−09 | 50.5 |
| mAb22810 | NT# | NT# | NT# | NT# | NT# | NT# |
| mAb25479 | 399 ± 0.7 | 135 | 5.30E+04 | 2.93E−04 | 5.53E−09 | 39.4 |
| mAb25491 | 286 ± 0.7 | 146 | 6.89E+04 | 1.10E−04 | 1.60E−09 | 105.0 |
| mAb25497 | 330 ± 0.5 | 100 | 5.74E+04 | 1.66E−04 | 2.90E−09 | 69.5 |
| mAb25498 | 369 ± 0 | 113 | 5.21E+04 | 4.64E−04 | 8.91E−09 | 24.9 |
| mAb25502 | 388 ± 1.5 | 139 | 8.52E+04 | 4.81E−04 | 5.65E−09 | 24.0 |
| mAb25508 | 344 ± 0.3 | 266 | 4.23E+05 | 1.50E−04 | 3.54E−10 | 77.1 |
| mAb25545 | 402 ± 0.7 | 82 | 3.71E+04 | 7.77E−05 | 2.09E−09 | 148.6 |
| IgG4 Isotype Control | 351 ± 0.5 | 9 | NB$ | NB$ | NB$ | NB$ |

$indicates that no binding was observed under the current experimental conditions
*indicates that the observed binding data were inconclusive
indicates that the conditions were not tested

TABLE 21

Binding kinetics parameters of mNPR1-mFc binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | $t^{1/2}$ (min) |
|---|---|---|---|---|---|---|
| mAb22033 | 350 ± 0.5 | 0 | NB$ | NB$ | NB$ | NB$ |
| mAb22035 | 346 ± 0.8 | −1 | NB$ | NB$ | NB$ | NB$ |
| mAb22805 | 330 ± 0.5 | 0 | NB$ | NB$ | NB$ | NB$ |
| mAb22809 | 328 ± 0.7 | 0 | NB$ | NB$ | NB$ | NB$ |
| mAb22810 | NT# | NT# | NT# | NT# | NT# | NT# |
| mAb25479 | 325 ± 0.3 | −1 | NB$ | NB$ | NB$ | NB$ |
| mAb25491 | 250 ± 1.1 | 1 | NB$ | NB$ | NB$ | NB$ |
| mAb25497 | 292 ± 0.7 | 1 | NB$ | NB$ | NB$ | NB$ |
| mAb25498 | 313 ± 1 | 0 | NB$ | NB$ | NB$ | NB$ |
| mAb25502 | 321 ± 1.1 | 1 | NB$ | NB$ | NB$ | NB$ |
| mAb25508 | 275 ± 0.7 | −1 | NB$ | NB$ | NB$ | NB$ |
| mAb25545 | 340 ± 0.2 | 0 | NB$ | NB$ | NB$ | NB$ |
| IgG4 Isotype Control | 296 ± 0.6 | 0 | NB$ | NB$ | NB$ | NB$ |

$indicates that no binding was observed under the current experimental conditions
indicates that the conditions were not tested
indicates that the conditions were not tested

TABLE 22

Binding kinetics parameters of mNPR1-mFc binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | $t^{1/2}$ (min) |
|---|---|---|---|---|---|---|
| mAb22033 | 413 ± 0.4 | 1 | NB$ | NB$ | NB$ | NB$ |
| mAb22035 | 444 ± 0.5 | 0 | NB$ | NB$ | NB$ | NB$ |
| mAb22805 | 400 ± 0.2 | 0 | NB$ | NB$ | NB$ | NB$ |
| mAb22809 | 407 ± 1 | 0 | NB$ | NB$ | NB$ | NB$ |
| mAb22810 | NT# | NT# | NT# | NT# | NT# | NT# |
| mAb25479 | 406 ± 0.3 | 2 | NB$ | NB$ | NB$ | NB$ |
| mAb25491 | 291 ± 0.9 | 1 | NB$ | NB$ | NB$ | NB$ |
| mAb25497 | 336 ± 0.7 | 1 | NB$ | NB$ | NB$ | NB$ |
| mAb25498 | 375 ± 1 | 0 | NB$ | NB$ | NB$ | NB$ |
| mAb25502 | 391 ± 0.6 | 1 | NB$ | NB$ | NB$ | NB$ |
| mAb25508 | 347 ± 0.4 | 0 | NB$ | NB$ | NB$ | NB$ |
| mAb25545 | 407 ± 0.7 | 1 | NB$ | NB$ | NB$ | NB$ |
| IgG4 Isotype Control | 359 ± 0.6 | 2 | NB$ | NB$ | NB$ | NB$ |

$indicates that no binding was observed under the current experimental conditions
indicates that the conditions were not tested

TABLE 23

Binding kinetics parameters of mNPR1-mFc:hANP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 348 ± 0.4 | 1 | NB$ | NB$ | NB$ | NB$ |
| mAb22035 | 345 ± 0.4 | 0 | NB$ | NB$ | NB$ | NB$ |
| mAb22805 | 330 ± 1.1 | 18 | 1.98E+05 | 8.39E−02 | 4.24E−07 | 0.14 |
| mAb22809 | 326 ± 0.4 | 0 | NB$ | NB$ | NB$ | NB$ |
| mAb22810 | NT# | NT# | NT# | NT# | NT# | NT# |
| mAb25479 | 324 ± 0.8 | 1 | NB$ | NB$ | NB$ | NB$ |
| mAb25491 | 249 ± 0.9 | 1 | NB$ | NB$ | NB$ | NB$ |
| mAb25497 | 290 ± 0.5 | 1 | NB$ | NB$ | NB$ | NB$ |
| mAb25498 | 311 ± 0.9 | 0 | NB$ | NB$ | NB$ | NB$ |
| mAb25502 | 317 ± 2.4 | 25 | 2.37E+05 | 7.99E−02 | 3.37E−07 | 0.14 |
| mAb25508 | 274 ± 0.8 | 0 | NB$ | NB$ | NB$ | NB$ |
| mAb25545 | 339 ± 0.3 | 1 | NB$ | NB$ | NB$ | NB$ |
| IgG4 Isotype Control | 295 ± 0.8 | 1 | NB$ | NB$ | NB$ | NB$ |

$indicates that no binding was observed under the current experimental conditions
indicates that the conditions were not tested

TABLE 24

Binding kinetics parameters of mNPR1-mFc:hANP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 402 ± 1.8 | 2 | NB$ | NB$ | NB$ | NB$ |
| mAb22035 | 435 ± 0.8 | 1 | NB$ | NB$ | NB$ | NB$ |
| mAb22805 | 392 ± 1 | 15 | IC* | IC* | IC* | IC* |
| mAb22809 | 400 ± 0.7 | 1 | NB$ | NB$ | NB$ | NB$ |
| mAb22810 | NT# | NT# | NT# | NT# | NT# | NT# |
| mAb25479 | 397 ± 1.2 | 2 | NB$ | NB$ | NB$ | NB$ |
| mAb25491 | 284 ± 0.7 | 1 | NB$ | NB$ | NB$ | NB$ |
| mAb25497 | 328 ± 0.8 | 1 | NB$ | NB$ | NB$ | NB$ |
| mAb25498 | 367 ± 0.4 | 1 | NB$ | NB$ | NB$ | NB$ |
| mAb25502 | 386 ± 2.1 | 35 | 2.64E+05 | 8.83E−02 | 3.34E−07 | 0.13 |
| mAb25508 | 343 ± 1.1 | 0 | NB$ | NB$ | NB$ | NB$ |
| mAb25545 | 401 ± 0.8 | 3 | NB$ | NB$ | NB$ | NB$ |
| IgG4 Isotype Control | 349 ± 0.5 | 2 | NB$ | NB$ | NB$ | NB$ |

$indicates that no binding was observed under the current experimental conditions
*indicates that the observed binding data were inconclusive
indicates that the conditions were not tested

TABLE 25

Binding kinetics parameters of mNPR1-mFc:hBNP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 347 ± 1.1 | 5 | NB$ | NB$ | NB$ | NB$ |
| mAb22035 | 345 ± 0.8 | 0 | NB$ | NB$ | NB$ | NB$ |
| mAb22805 | 329 ± 0.9 | 21 | 1.53E+05 | 6.82E−02 | 4.45E−07 | 0.17 |
| mAb22809 | 326 ± 1.1 | 1 | NB$ | NB$ | NB$ | NB$ |
| mAb22810 | NT# | NT# | NT# | NT# | NT# | NT# |
| mAb25479 | 325 ± 0.2 | 1 | NB$ | NB$ | NB$ | NB$ |
| mAb25491 | 249 ± 0.4 | 5 | NB$ | NB$ | NB$ | NB$ |
| mAb25497 | 291 ± 0.2 | 2 | NB$ | NB$ | NB$ | NB$ |
| mAb25498 | 312 ± 0.8 | 1 | NB$ | NB$ | NB$ | NB$ |
| mAb25502 | 318 ± 0.3 | 25 | 2.34E+05 | 5.03E−02 | 2.15E−07 | 0.23 |
| mAb25508 | 274 ± 0.6 | 1 | NB$ | NB$ | NB$ | NB$ |
| mAb25545 | 339 ± 0.4 | 3 | NB$ | NB$ | NB$ | NB$ |

TABLE 25-continued

Binding kinetics parameters of mNPR1-mFc:hBNP complex binding to NPR1 monoclonal antibodies at 25° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| IgG4 Isotype Control | 296 ± 0.6 | 2 | NB$ | NB$ | NB$ | NB$ |

$indicates that no binding was observed under the current experimental conditions.
indicates that the conditions were not tested

TABLE 26

Binding kinetics parameters of mNPR1-mFc:hBNP complex binding to NPR1 monoclonal antibodies at 37° C.

| mAb Captured | mAb Capture Level (RU) | 100 nM Ag Bound (RU) | $k_a$ (1/Ms) | $k_d$ (1/s) | KD (M) | t½ (min) |
|---|---|---|---|---|---|---|
| mAb22033 | 401 ± 0.2 | 4 | NB$ | NB$ | NB$ | NB$ |
| mAb22035 | 433 ± 0.5 | 1 | NB$ | NB$ | NB$ | NB$ |
| mAb22805 | 389 ± 0.8 | 17 | IC* | IC* | IC* | IC* |
| mAb22809 | 397± 1.3 | 1 | NB$ | NB$ | NB$ | NB$ |
| mAb22810 | NT# | NT# | NT# | NT# | NT# | NT# |
| mAb25479 | 397 ± 0.9 | 2 | NB$ | NB$ | NB$ | NB$ |
| mAb25491 | 282 ± 0.9 | 4 | NB$ | NB$ | NB$ | NB$ |
| mAb25497 | 327 ± 0.5 | 2 | NB$ | NB$ | NB$ | NB$ |
| mAb25498 | 366 ± 0.6 | 1 | NB$ | NB$ | NB$ | NB$ |
| mAb25502 | 384 ± 1.3 | 34 | 2.91E+05 | 9.98E−02 | 3.42E−07 | 0.12 |
| mAb25508 | 342 ± 0.9 | 1 | NB$ | NB$ | NB$ | NB$ |
| mAb25545 | 400 ± 0.4 | 4 | NB$ | NB$ | NB$ | NB$ |
| IgG4 Isotype Control | 348 ± 0.7 | 3 | NB$ | NB$ | NB$ | NB$ |

$indicates that no binding was observed under the current experimental conditions
*indicates that the observed binding data were inconclusive
indicates that the conditions were not tested As shown in Tables 3 to 6, selected anti-NPR1 antibodies bound to monomeric human and monkey NPR1.

As shown in Tables 9 to 20, the antibodies bound to human and monkey NPR1 dimer in both the presence and absence of ANP or BNP.

The antibodies did not bind to mouse NPR1, except mAb25502 bound to mNPR1 in the presence of ANP/BNP (Tables 21 to 26).

Example 4: Cross-Competition Between Selected Anti-NPR1 Agonist Monoclonal Antibodies Experimental Procedure Binding competition within a panel of anti-NPR1 monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH7.4 (HBS-EBT) buffer with the plate shaking at the speed of 1000 rpm. To assess whether 2 antibodies are able to compete with one another for binding to their respective epitopes, 100 nM recombinant human NPR1 expressed with a C-terminal mouse IgG2a (hNPR1-mFc; SEQ ID: 453) was first incubated with 2 µM of human ANP for at least 2 hours. Around 0.3-0.5 nm recombinant hNPR1-mFc/hANP complex was first captured by dipping anti-mouse Fc antibody coated Octet biosensor tips (Fortebio Inc, #18-5090) by submerging the biosensor tips for 45 seconds in wells containing hNPR1-mFc/hANP complex. The antigen captured biosensor tips were then saturated with the first anti-NPR1 monoclonal antibody (referred to as mAb-1) by dipping into wells containing 50 µg/mL solution of mAb-1 for 5 minutes. The biosensor tips were then dipped into wells containing 50 µg/mL solution of second anti-NPR1 monoclonal antibody (referred to as mAb-2) for 3 minutes. The biosensor tips were washed in HBS-EBT buffer between every step of the experiment. The real-time binding response was monitored during the entire course of the experiment and the binding response at the end of every step was recorded. The response of mAb-2 binding to hNPR1-mFc/hANP pre-complexed with mAb-1 was compared and competitive/non-competitive behavior of different anti-NPR1 monoclonal antibodies was determined.

Results

TABLE 27

Cross-competition between anti-NPR1 monoclonal antibodies

| mAb-1 | mAb-2 competing with mAb-1 |
|---|---|
| mAb25498 | mAb25508 |
| mAb25508 | mAb25498 |
| mAb22809 | mAb22810 |
|  | mAb22033 |
|  | mAb25491 |
|  | mAb25497 |
|  | mAb25502 |
|  | mAb25545 |

TABLE 27-continued

Cross-competition between anti-NPR1 monoclonal antibodies

| mAb-1 | mAb-2 competing with mAb-1 |
|---|---|
| mAb22033 | mAb22805 |
|  | mAb25479 |
|  | mAb22809 |
|  | mAb25491 |
|  | mAb25497 |
|  | mAb25502 |
|  | mAb25545 |
|  | mAb22805 |
|  | mAb25479 |
|  | mAb22810 |
| mAb25491 | mAb22809 |
|  | mAb22033 |
|  | mAb25497 |
|  | mAb25502 |
|  | mAb25545 |
|  | mAb22805 |
|  | mAb25479 |
|  | mAb22810 |
| mAb25497 | mAb22809 |
|  | mAb22033 |
|  | mAb25491 |
|  | mAb25502 |
|  | mAb25545 |
|  | mAb22805 |
|  | mAb25479 |
|  | mAb22810 |
| mAb25502 | mAb22809 |
|  | mAb22033 |
|  | mAb25491 |
|  | mAb25497 |
|  | mAb25545 |
|  | mAb22805 |
|  | mAb25479 |
|  | mAb22810 |
| mAb25545 | mAb22809 |
|  | mAb22033 |
|  | mAb25491 |
|  | mAb25497 |
|  | mAb25502 |
|  | mAb22805 |
|  | mAb25479 |
|  | mAb22810 |
| mAb22805 | mAb22809 |
|  | mAb22033 |
|  | mAb25491 |
|  | mAb25497 |
|  | mAb25502 |
|  | mAb25545 |
|  | mAb22810 |
| mAb25479 | mAb22809 |
|  | mAb22033 |
|  | mAb25491 |
|  | mAb25497 |
|  | mAb25502 |
|  | mAb25545 |
|  | mAb22810 |
| mAb22810 | mAb22809 |
|  | mAb25445 |

Table 27 shows the cross-competition between selected anti-NPR1 antibodies.

Example 5: Antibody Binding to Cells Expressing NPR1

Experimental Procedure

The ability of anti-human (h) NPR1 monoclonal antibodies to bind to human NPR1 (hNPR1) expressing cells with or without one of the ligands—human ANP (hANP), was determined using electrochemiluminescence (ECL) based detection.

Briefly, HEK293/hNPR1.myc.DKK expressing cells were engineered by transfecting human embryonic kidney (HEK) 293 cells with neomycin resistant pLVX.hNPR1.myc.DDK expression plasmid encoding human NPR1 (amino acids M1-G1061, UniProtKB - P16066). The non-transfected HEK293 cells have no detectable expression of NPR1 by fluorescence activated cell sorting (FACS) with commercial a-hNRP1 antibodies and were included as non-specific binding controls.

Experiments were carried out according to the following procedure. Cells from lines described above were rinsed once in 1×PBS buffer without $Ca^{2+}/Mg^{2+}$ and incubated for 10 minutes at 37° C. with Enzyme Free Cell Dissociation Solution to detach cells from a flask. All cells were washed once with 1×PBS with $Ca^{2+}/Mg^{2+}$ and counted with a Cellometer™ Auto T4 cell counter (Nexcelom Bioscience). Approximately $2.0×10^4$ HEK293/hNPR1.myc.DDK or HEK293 cells were seeded separately onto 96-well carbon electrode plates (MULTI-ARRAY high bind plate, Meso Scale Discovery (MSD, Rockville, Md.)) and incubated for 1 hour (h) at 37° C. Nonspecific binding sites were blocked by 2% BSA (w/v) in 1×PBS with $Ca^{2+}/Mg^{2+}$ for 1 h at room temperature (RT). HEK293/hNPR1.myc.DDK cells were incubated for 0.5 hour at RT in sample dilution buffer with or without 10 nM human ANP (Tocris, Minneapolis, Minn.), and HEK293 cells were incubated in sample dilution buffer only at the same conditions. Without washing, serial dilutions of anti-NPR1, COMP1 or isotype control antibodies, ranging from 1.7 pM to 100 nM, or buffer containing no antibody were added to plate-bound cells for 1 h, RT. Plates were then washed to remove unbound antibodies and/or hANP using an AquaMax2000 plate washer with a cell washing head (MDS Analytical Technologies, Sunnyvale, Calif.). The plate-bound antibodies were detected with SULFO-TAG™-conjugated goat polyclonal anti-human IgG antibody specific for heavy and light chains (Jackson Immunoresearch, West Grove, Pa.) for 1 h, RT.

After washes, plates were developed with Read Buffer (MSD, Rockville, Md.) according to manufacturer's recommended procedure and luminescent signals were recorded with a SECTOR Imager 600 (MSD, Rockville, Md.). Luminescence intensity, measured in relative light units (RLU), was recorded to indicate the binding intensity of each antibody at the range of concentrations. The ratio of signal detected with 3.7 nM antibody binding to the NPR1 engineered cells with or without 10 nM hANP compared to the same concentration of antibody binding to parental cells with no hANP added was reported as an indication of specificity of NPR1 binding. Antibodies with the binding ratio of greater than or equal to 3 were classified as specific binders and antibodies with the binding ratio less than 3 were classified as non-binders.

In addition, direct binding signals (RLU) were analyzed as a function of the antibody concentration and data were fitted with a sigmoidal (four-parameter logistic) dose-response model using R statistical package (open source). The $EC_{50}$ value, defined as the concentration of antibody at which 50% of the maximal binding signal is detected, was determined to indicate binding potency to NPR1 engineered cells with or without 10 nM hANP. $EC_{50}$ values were reported only for specific binders and marked with (–) for antibodies with ratio below 3 in Table 28.

Results

Table 28 shows binding of selected anti-NPR1 antibodies to cells engineered to express human NPR1 or NPR1-ANP complex.

TABLE 28

Anti-NPR1 Antibodies Binding to Cells Engineered to Express Human NPR1 or NPR1-ANP Complex on the Cell Surface

| Ab PID | Ratio at 3.7 nM Ab concentration of Cell Binding Signal (RLU) to HEK293/hNPR1.myc.DKK relative to parental HEK293 | | Cell Binding Potency to HEK293/ hNPR1.myc.DKK, $EC_{50}$ (M) | |
|---|---|---|---|---|
| | +10 nM hANP | 0 hANP | +10 nM hANP | 0 hANP |
| Peptide-dependent NPR1 binders | | | | |
| mAb22809 | 166 | 2 | 4.8E−10 | — |
| mAb22805 | 222 | 1 | 6.5E−10 | — |
| mAb25545 | 79 | 1 | 1.9E−09 | — |
| mAb22810 | 24 | 1 | 3.7E−09 | — |
| mAb25502 | 14 | 1 | INC | — |
| Comparator1 | 103 | 2 | 1.5E−10 | — |
| Peptide-independent NPR1 binders | | | | |
| mAb22033 | 236 | 207 | 8.2E−10 | 4.9E−10 |
| mAb25497 | 87 | 50 | 8.7E−10 | 1.5E−09 |
| mAb22035 | 220 | 151 | 8.9E−10 | 2.3E−09 |
| mAb25491 | 78 | 58 | 1.0E−09 | 1.6E−09 |
| mAb25479 | 51 | 30 | 1.2E−09 | 1.7E−09 |
| mAb25508 | 35 | 18 | 1.3E−09 | INC |
| mAb25498 | 49 | 41 | 1.8E−09 | 4.6E−09 |
| hIgG4 Isotype Control | 1 | 1 | — | — |

(INC) = inconclusive, no top plateau developed with four-parameters sigmoidal curve fit to calculate $EC_{50}$ value, but antibody specifically bound to NPR1 engineered cells with or without 10 nM hANP with ratio of equal or greater than 3

As the results in Table 28 show, all anti-NPR1 antibodies bound specifically to the hNPR1 engineered cells in the presence of 10 nM hANP with a ratio ≥2. The potency of these antibodies on HEK293/hNPR1.myc.DDK cells with 10 nM hANP ranged from $EC_{50}$ values of 0.15 nM to 3.7 nM. Five antibodies and Comparator1 specifically bound to NPR1 engineered cells only in the presence of 10 nM hANP and were classified as peptide-dependent NPR1 binders. The other seven antibodies bound to hNPR1 engineered cells with and without 10 nM hANP and these antibodies were classified as peptide-independent NPR1 binders. The potency of these antibodies on HEK293/hNPR1.myc.DDK cells with no hANP added ranged from $EC_{50}$ values of 0.49 nM to 4.6 nM.

Example 6: Activation of NPR1 by Agonist Anti-NPR1 Monoclonal Antibodies

Experimental Procedure

In order to assess the transcriptional activation of human natriuretic peptide receptor 1 (hNPR1), a stable cell line was developed by stably expressing cyclic nucleotide gated channel alpha 2 (CNGA2) and hNPR1 in HEK293. CNGA2 is a calcium channel that can be activated by cGMP, therefore, it can be used as a sensor for cGMP generation (Wunder et al. 2005, PMID: 15766716). As NPR1 is activated by the ligand and produces cGMP (Zois et al., 2014, PMID: 24820868), CNGA2 is activated and calcium influx can be measured using a fluorescent $Ca^{++}$ indicator. The cell line was sorted for high expression of hNPR1, HEK293/hNPR1.MycDDK/CNGA2.Myc HS or abbreviated as HEK293/CNGA2/hNPR1, and maintained in DMEM containing 10% FBS, NEAA, pen/strep/glut, 100 µg/mL hygromycin, and 500 µg/mL G418 sulfate.

A bioassay was performed to measure the effect of anti-hNPR1 antibodies on human NPR1 signaling in the absence of ANP. For the bioassay, HEK293/CNGA2/hNPR1 cells were seeded in black clear bottom PDL plates at 30,000 cells/well in DMEM containing 10% FBS, NEAA, pen/strep/glut and incubated at 37° C. and 5% $CO_2$ overnight. The next morning, media was removed and cells were loaded with 80 µl of FLUO4-NW assay buffer with probenecid (Thermo Scientific) for 30 min at 37° C. Purified hNPR1 antibodies or an isotype control antibody were serially diluted at 1:3 from ~0.4 nM-1 µM (8-point) or ANP at 1:3 from ~0.3 µM to 2 nM (10-point) were transferred to the assay plate using FLIPR TETRA® (Molecular Devices). Base line and response images were captured. Dosage response curve were determined based on Max-Min or Area under curve (shown here) and the results were analyzed using nonlinear regression (4-parameter logistics) with Prism™6 software (GraphPad) to obtain $EC_{50}$ values. The % activation of antibodies was calculated with the maximum range of RFU achieved by the antibody over the maximum range of RFU achieved by ANP.

Results

Table 29 shows activation of human NPR1 by anti-NPR1 antibodies.

TABLE 29

Activation of human NPR1 by anti-NPR1 antibodies

| | Expt I | | Expt II | |
|---|---|---|---|---|
| Cells | 293/CNGA2/hNPR1 | | 293/CNGA2/hNPR1 | |
| Mode | Activation | | Activation | |
| Ligand | ANP | | ANP | |
| $EC_{50}$ (pM) | 60.5-98.8 | | 78.8 | |
| Constant | None | | None | |
| Antibody | $EC_{50}$ (nM) | % Activation (vs ANP max) | $EC_{50}$ (nM) | % Activation (vs. ANP max) |
| mAb22033 | 83.7 | 129.54 | 41.6 | 129.20% |
| mAb22810 | Not tested | Not tested | 50.8 | 125.50% |
| mAb25545 | 187.9 | 123.14% | 74.1 | 122.70% |
| mAb25502 | 161.4 | 92.90% | >200 | 109.80% |
| mAb22805 | 239 | 91.61% | 112.3 | 118.90% |
| mAb22809 | 270 | 86.72% | Not tested | Not tested |
| mAb25491 | 101.8 | 74.64% | 43.4 | 103.70% |
| mAb22035 | 383.9 | 73.07% | >200 | 56.80% |
| mAb25497 | 72.62 | 71.09% | 56.4 | 103.40% |
| mAb25498 | 335.3 | 67.74% | Not tested | Not tested |
| mAb25479 | 174.3 | 66.73% | 101.9 | 82.80% |
| mAb25508 | 325.7 | 56.08% | Not tested | Not tested |
| Comparator 1 | >2000 | 53.45% | No activation | 13.80% |
| Isotype Control | No activation | −6.03% | No activation | 1.90% |

The activation of hNPR1 by selected anti-NPR1 antibodies of the invention was tested by measuring calcium flux activity in HEK293/CNGA2/hNPR1 in two experiments (Expt I and II) (Table 29). As shown in Table 29 (in Expt I), 11 purified NPR1 antibodies showed activation in Ca2+ flux, ranging from 55-130% maximum activation with $EC_{50}$s ranging 83.7-383.9 nM. 19 antibodies showed weak activation with maximum activation less than 31% (data not shown). In Expt II, 9 anti-NPR1 antibodies showed activation in Ca2+ flux ranging from 57-129% maximum activation with $EC_{50}$s of 41.6->200 nM (Table 29). ANP activated with $EC_{50}$s of 60.5-98.8 pM. No activation was observed with the control hIgG4 isotype antibody.

Example 7: Effect of a Single Dose of an Agonist Anti-NPR1 Monoclonal Antibody on Systemic Blood Pressure in Normotensive NPR1$^{hu/hu}$ Mice Experimental Procedure The objectives of this study were to assess the effects of selected NPR1 agonist antibodies on baseline systemic blood pressure in telemetered normotensive NPR1$^{hu/hu}$ mice. Male NPR1$^{hu/hu}$ (n=50) mice aged ~10-20 weeks were implanted with PA-C10 telemeters (DSI, St. Paul, Minn.) and allowed to recover for 7 days, prior to being assigned to group (Groups 1-12) (Table 30).

TABLE 30

Summary of doses and dose groups

| Group No. | Test or Control Article | Dose Level (mg/kg/dose) | Dose Volume (mL/kg) | Number of Animals Males |
|---|---|---|---|---|
| 1 | PBS control | 25 | 5 | 9 |
| 3 | mAb22035 | | | 5 |
| 4 | mAb22033 | | | 4 |
| 5 | mAb25497 | | | 3 |
| 6 | mAb22805 | | | 4 |
| 7 | mAb25545 | | | 3 |
| 8 | mAb22809 | | | 5 |
| 9 | mAb25479 | | | 4 |
| 10 | mAb25491 | | | 4 |
| 11 | mAb25502 | | | 5 |
| 12 | mAb22810 | | | 4 |

Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

The test proteins or phosphate buffered saline (PBS) were administered to the appropriate animals by single subcutaneous injection on Day 0. The dose volume for each animal was based on the most recent body weight measurement.

Systolic pressure, diastolic pressure, mean arterial pressure and heart rate were collected for 10 seconds every minute for the duration of the testing period. An acute assessment of efficacy was made with data compiled from study day 3 to study day 7. The chronic effects of NPR1 agonist antibodies were assessed with daily 24-hour data collected and averaged over 28 days. All data are presented as mean±SEM.

Results

The initial in vivo screen of NPR1 agonist antibodies demonstrated that when compared to PBS-dosed control animals from days 3 to 7 post-dose, 9 antibodies (mAb22033, mAb25479, mAb25497, mAb22805, mAb25545, mAb22809, mAb25491, mAb25502 and mAb22810) significantly reduced, and 1 antibody (mAb22035) had no effect on systemic blood pressures (FIG. 1). The magnitude of blood pressure reduction as assessed by mean (of days 3 to 7 post-dose) systolic blood pressure change from baseline ranged from −3.2±0.2 (mAb25497N) to −11.5±0.8 (mAb22810) mmHg.

Chronic effects of the NPR1 agonist antibodies were evaluated over 28 days (Table 31).

TABLE 31

28-day mean blood pressures and heart rates

| Dose Group | Systolic (mmHg) | Diastolic (mmHg) | Mean Arterial (mmHg) | Heart Rate (BPM) |
|---|---|---|---|---|
| PBS control | 0.08 ± 0.09 | 1.09 ± 0.25 | 1.19 ± 0.27 | 11.79 ± 3.17 |
| mAb25545 | −4.34 ± 0.18* | 0.13 ± 0.38* | −2.0 ± 0.46* | 5.35 ± 3.13* |
| mAb22805 | −3.90 ± 0.17* | −1.51 ± 0.30* | −3.40 ± 0.40* | 18.83 ± 2.73* |
| mAb25497 | −3.04 ± 0.20* | 2.37 ± 0.36* | 1.04 ± 0.44 | 12.07 ± 2.64* |
| mAb22035 | 3.80 ± 0.32* | 2.05 ± 0.22* | 2.95 ± 0.26* | 2.86 ± 2.33* |
| mAb22033 | −11.07 ± 0.59* | −4.55 ± 0.38* | −8.01 ± 0.48* | −2.14 ± 2.83* |
| mAb22810 | −7.88 ± 0.57* | −2.24 ± 0.31* | −5.21 ± 0.42* | −6.10 ± 2.96* |
| mAb25502 | −3.63 ± 0.49* | −0.41 ± 0.40* | −2.13 ± 0.44* | −14.27 ± 2.87* |
| mAb22809 | −2.01 ± 0.58* | 2.95 ± 0.70* | 0.30 ± 0.62 | 3.95 ± 2.33* |
| mAb25491 | −4.90 ± 0.35* | −1.22 ± 0.26* | −3.19 ± 0.30* | −12.9 ± 3.22* |
| mAb25479 | −3.44 ± 0.50* | 0.51 ± 0.42* | −1.60 ± 0.44* | −4.01 ± 3.03* |

Telemetered normotensive NPR1$^{hu/hu}$ mice were randomized into groups based off of body weight. Animals were given a single 25 mg/kg subcutaneous injection of NPR1 agonist mAb or PBS control as described in Table 1. All values are mean ± SEM, n = 3-9 per group. Statistics—two way ANOVA with Dunnett's;
*p < .05 vs. PBS control Following a single subcutaneous injection on day 0, one antibody (mAb22035) significantly increased pressures by ~4-7 mmHg, while the remaining antibodies reduced systemic blood pressures 2 to 11 mmHg in normotensive NPR1$^{hu/hu}$ mice. Heart rate responses to both increased and decreased systemic blood pressures were variable, with some groups increasing and others decreasing.

Example 8: Dose Effect of an Agonist Anti-NPR1 Monoclonal Antibody on Systemic Blood Pressure in Normotensive NPR1$^{hu/hu}$ Mice Experimental Procedure The objective of this study was to assess a dose response of the NPR1 agonist antibody mAb22033 on systemic blood pressure in telemetered normotensive NPR1$^{hu/hu}$ mice. Male NPR1$^{hu/hu}$ (n=30) mice aged ~20 weeks were implanted with PA-C10 telemeters (DSI, St. Paul, Minn.) and allowed to recover for 7 days, prior to being assigned to group (Groups 1-5) (Table 32).

TABLE 32

Summary of doses and dose groups

| Group No. | Test or Control Article | Dose Level (mg/kg/dose) | Dose Volume (mL/kg) | Number of Animals Males |
|---|---|---|---|---|
| 1 | IgG4 isotype control | 25 | 5 | 6 |
| 2 | mAb22033 | 1 | 5 | 7 |
| 3 | mAb22033 | 5 | 5 | 6 |
| 4 | mAb22033 | 25 | 5 | 7 |
| 5 | mAb22033 | 50 | 5 | 7 |

Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

The test proteins were administered to the appropriate animals once on day 0 via subcutaneous injection. The dose volume for each animal was based on the most recent body weight measurement. For urine and serum biomarker assessment, urine was collected on day 28 and blood samples were collected on study day 14 and upon termination. Echocardiography was performed on day 28, prior to diuresis.

Systolic pressure, diastolic pressure, mean arterial pressure, and heart rate were collected for 10 seconds every minute for the duration of the testing period. Graphically displayed telemetry data were obtained from animals with viable signals for the duration of the in-life portion of the study.

Results

Figure 2:
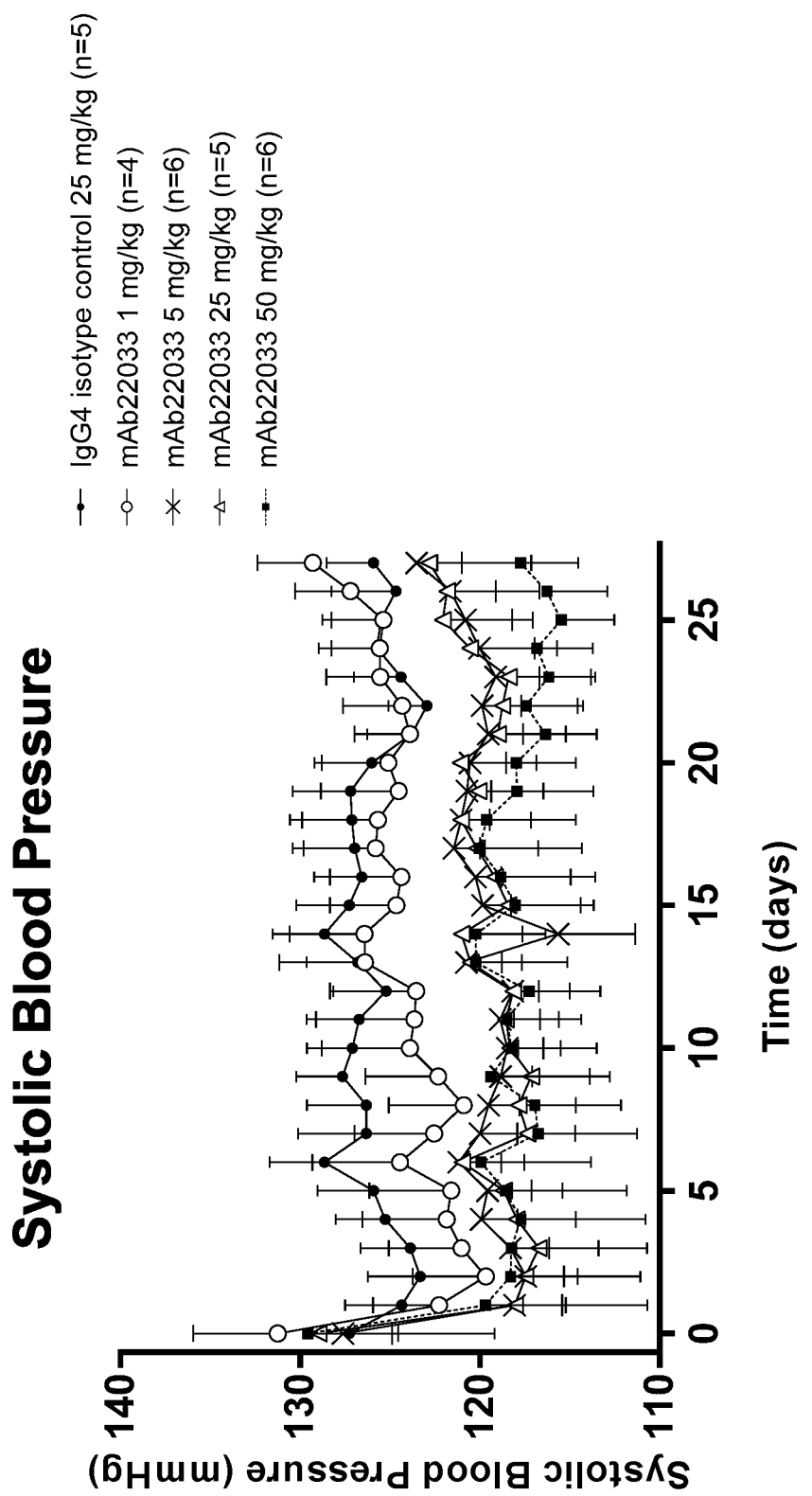
FIG. 2 shows the effect of anti-NPR1 antibody mAb22033 on systolic blood pressure in normotensive NPR1$^{hu/hu}$ mice. Telemetered normotensive NPR1$^{hu/hu}$ mice were randomized into five groups of equal body weight and given a single subcutaneous injection of mAb22033 at the doses listed in Table 32. An IgG4 antibody was used as isotype control. All values are mean±SEM, n=4-6 per group. Statistics—two-way ANOVA with Dunnett's.
Figure 3:
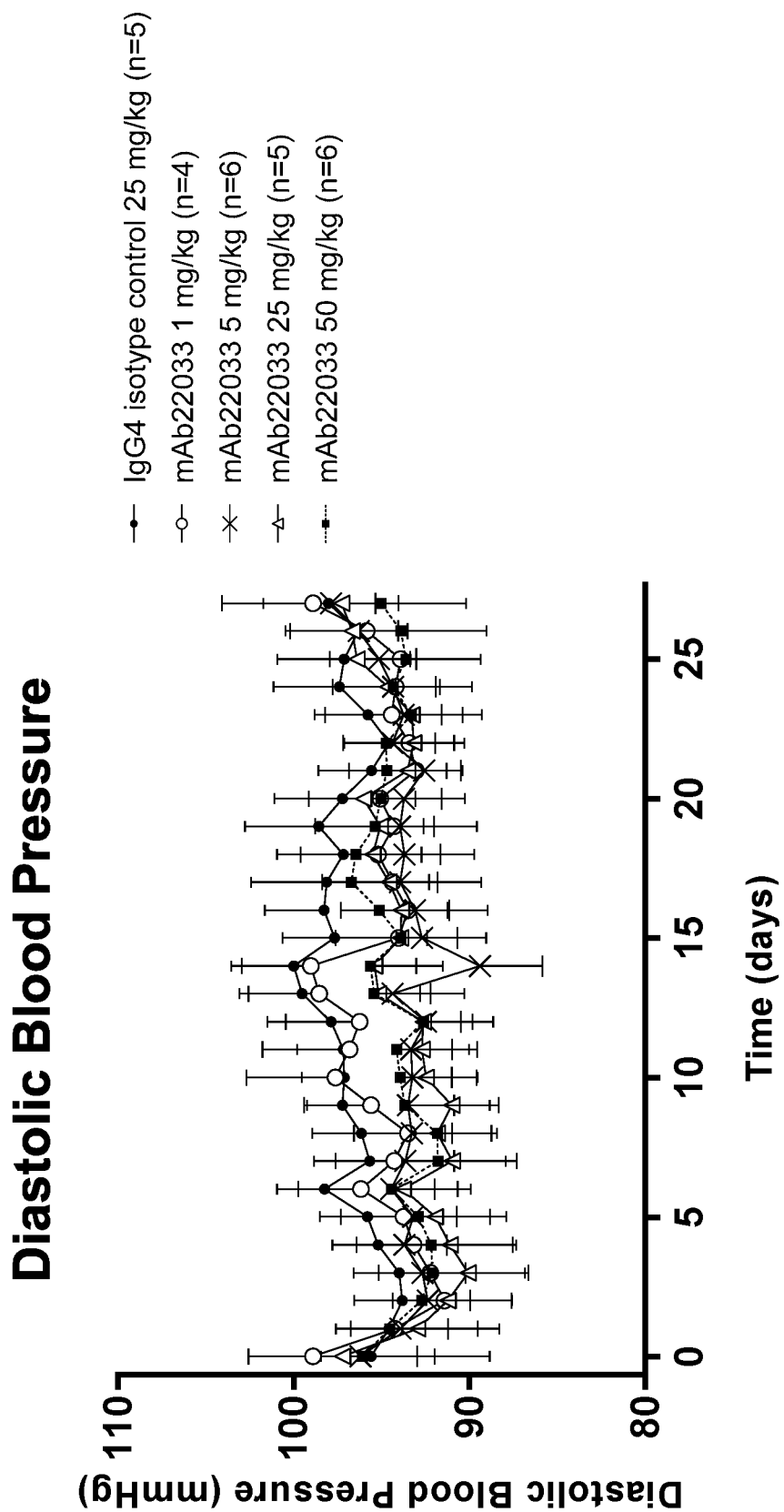
FIG. 3 shows the effect of anti-NPR1 antibody mAb22033 on diastolic blood pressure in normotensive NPR1$^{hu/hu}$ mice. Telemetered normotensive NPR1$^{hu/hu}$ mice were randomized into five groups of equal body weight and given a single subcutaneous injection of mAb22033 at the doses listed in Table 32. An IgG4 antibody was used as isotype control. All values are mean±SEM, n=4-6 per group. Statistics—two-way ANOVA with Dunnett's.
Figure 4:
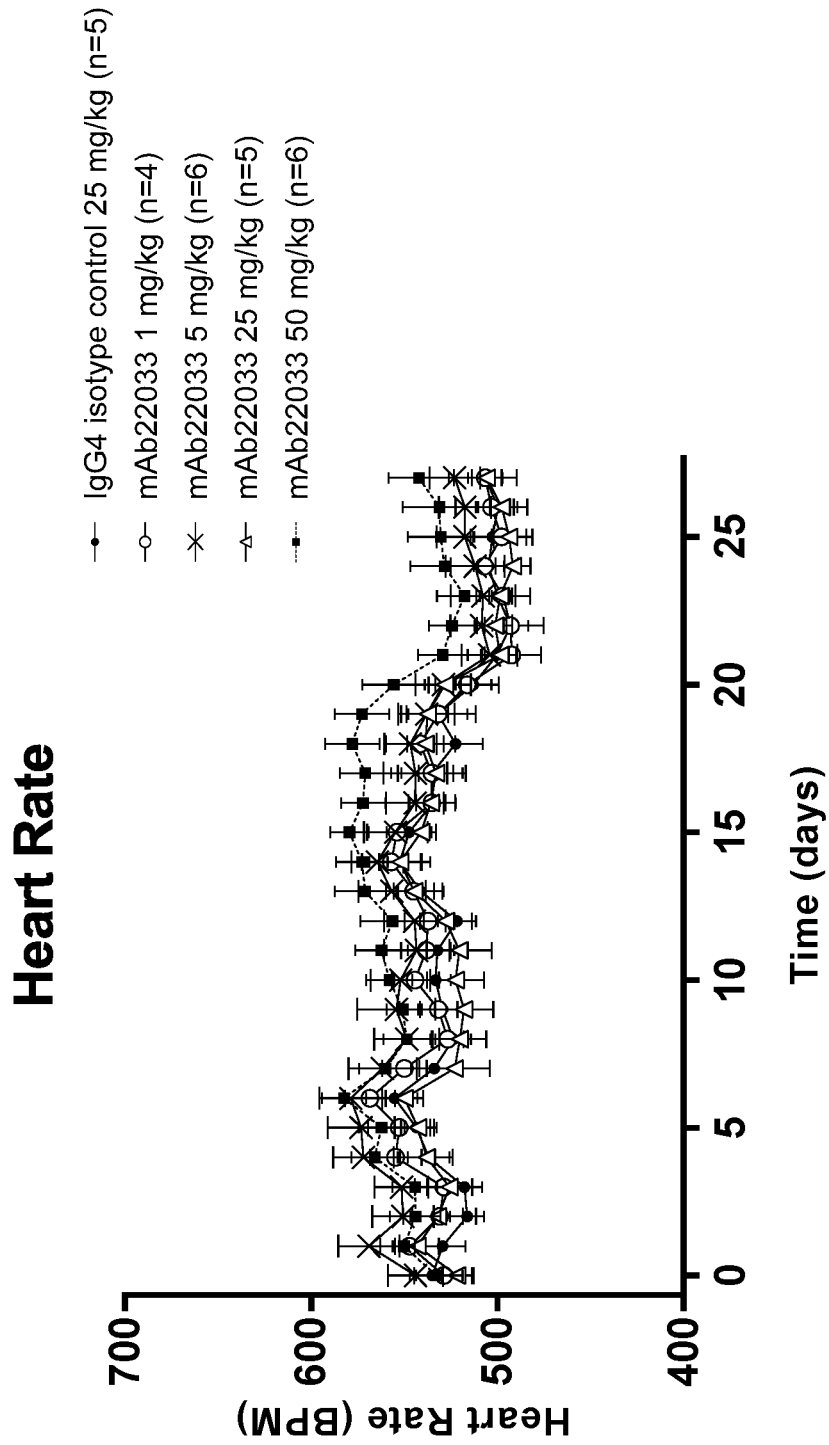
FIG. 4 shows the effect of anti-NPR1 antibody mAb22033 on heart rate in normotensive NPR1$^{hu/hu}$ mice. Telemetered normotensive NPR1$^{hu/hu}$ mice were randomized into five groups of equal body weight and given a single subcutaneous injection of mAb22033 at the doses listed in Table 32. An IgG4 antibody was used as isotype control. All values are mean±SEM, n=4-6 per group. Statistics—two-way ANOVA with Dunnett's.
Figure 5:
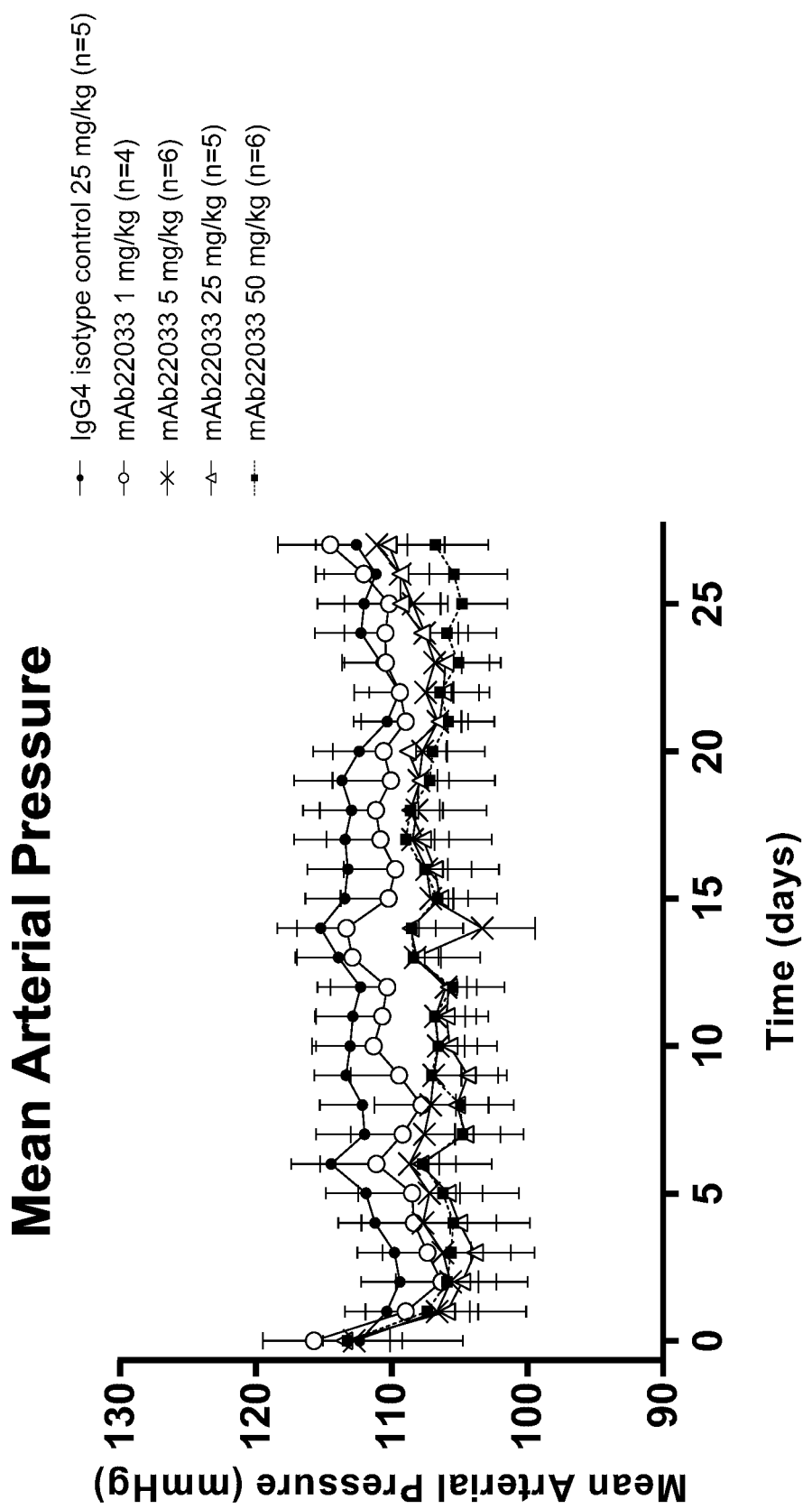
FIG. 5 shows the effect of anti-NPR1 antibody mAb22033 on mean arterial blood pressure in normotensive NPR1$^{hu/hu}$ mice. Telemetered normotensive NPR1$^{hu/hu}$ mice were randomized into five groups of equal body weight and given a single subcutaneous injection of mAb22033 at the doses listed in Table 32. An IgG4 antibody was used as isotype control. All values are mean±SEM, n=4-6 per group. Statistics—two-way ANOVA with Dunnett's.

Blood pressures (FIGS. 2, 3 and 5) were reduced 10-15 mmHg for up to 4 weeks after a single dose of mAb22033 to normotensive NPR1$^{hu/hu}$ mice. Peak pressure reductions for all doses were similar, with the duration of blood pressure effect being approximately 10 days at 1 mg/kg and longer than 28 days for 50 mg/kg.

TABLE 33

28-day Mean Blood Pressures and Heart Rate

| Dose Group: | Systolic (mmHg) | Diastolic (mmHg) | Mean Arterial (mmHg) | Heart Rate (BPM) |
|---|---|---|---|---|
| IgG4 isotype control (25 mg/kg) | 126 ± 0.3 | 97.0 ± 0.3 | 112.2 ± 0.3 | 524.9 ± 3.2 |
| mAb22033 (1 mg/kg) | 124.4 ± 0.5 | 95.1 ± 0.4 | 110.4 ± 0.4 | 530.6 ± 4.0 |
| mAb22033 (5 mg/kg) | 120.0 ± 0.4**** | 93.8 ± 0.3** | 107.6 ± 0.3**** | 543.4 ± 4.0**** |
| mAb22033 (25 mg/kg) | 119.7 ± 0.5**** | 93.7 ± 0.4* | 107.1 ± 0.4**** | 524.5 ± 3.4 |
| mAb22033 (50 mg/kg) | 118.5 ± 0.5**** | 94.2 ± 0.3* | 106.8 ± 0.3**** | 553.6 ± 3.5**** |

Telemetered normotensive NPR1$^{hu/hu}$ mice were randomized into five groups of equal body weight and given a single subcutaneous injection of mAb22033 at the doses listed in Table 1. An IgG4 antibody was used as isotype control. All values are mean ± SEM, n = 6-7 per group. Statistics—two way ANOVA with Dunnett's;
*$p < .05$ vs. IgG4 isotype control,
**$p < .01$ vs. IgG4 isotype control;
***$p < .001$ vs. IgG4 isotype control;
****$p < .0001$ vs. IgG4 isotype control Urinary cGMP concentrations (Table 34) were significantly increased on day 28 in the 50 mg/kg group, with all other doses being of a similar level to controls.

TABLE 34

Urine and serum markers

| Dose Group: | Urine Volume (mL/day) | Urinary cGMP (mmol/day) | Serum NTproANP (nmol/L)— Day 14 | Serum NTproANP (nmol/L)— Day 29 |
|---|---|---|---|---|
| IgG4 isotype control (25 mg/kg) | 1.4 ± 0.2 | 5.0 ± 1.3 | 0.21 ± .06 | 0.49 ± 0.17 |
| mAb22033 (1 mg/kg) | 1.2 ± 0.2 | 5.2 ± 1.3 | 0.35 ± 0.11 | 0.52 ± 0.12 |
| mAb22033 (5 mg/kg) | 0.9 ± 0.1 | 3.7 ± 0.8 | 0.20 ± 0.08 | 0.20 ± 0.05 |
| mAb22033 (25 mg/kg) | 1.2 ± 0.2 | 5.9 ± 0.8 | 0.14 ± 0.06 | 0.24 ± 0.06 |
| mAb22033 (50 mg/kg) | 1.4 ± 0.2 | 11.9 ± 2.1** | 0.26 ± 0.08 | 0.56 ± 0.20 |

Telemetered normotensive NPR1$^{hu/hu}$ mice were randomized into five groups of equal body weight and given a single subcutaneous injection of mAb22033 at the doses listed in Table 1. An IgG4 antibody was used as isotype control. All values are mean ± SEM, n = 6-7 per group. Statistics—one way ANOVA with Dunnett's;
**$p < .01$ vs. IgG4 isotype control Relative heart weight (Table 35) was lower in the 50 mg/kg group, with trending reductions in the 1, 5 and 25 mg/kg groups. No significant effects on body weight (Table 35), absolute heart weight (Table 35), standard serum (ALT, AMYLAS, AST, CHOL, CKNAC, CREA, DHDL, IP, TRIG, TP, UA, UN, MG, NEFA) or urine (ALB, GLUH, CREA, PRO, CA, IP, MG, UN, AMYLAS, UA, NA, K, CL) chemistries were observed.

TABLE 35

Terminal Body and Organ Weights

| Dose Group: | Terminal Body Weight (g) | Heart Weight (mg) | Heart Weight:Tibia Length | Heart Weight:Body Weight |
|---|---|---|---|---|
| IgG4 isotype control (25 mg/kg) | 33.1 ± 1.7 | 0.143 ± 0.003 | 0.0079 ± 0.0002 | 0.0043 ± 0.0001 |
| mAb22033 (1 mg/kg) | 34.5 ± 2.3 | 0.140 ± 0.005 | 0.0078 ± 0.0002 | 0.0041 ± 0.0001 |
| mAb22033 (5 mg/kg) | 34.3 ± 1.4 | 0.131 ± 0.006 | 0.0075 ± 0.0004 | 0.0039 ± 0.0003 |
| mAb22033 (25 mg/kg) | 32.4 ± 1.4 | 0.126 ± 0.006 | 0.0071 ± 0.0003 | 0.0039 ± 0.0002 |
| mAb22033 (50 mg/kg | 34.3 ± 2.1 | 0.124 ± 0.004 | 0.0069 ± 0.0002 | 0.0037 ± 0.0002* |

Figure 6B:
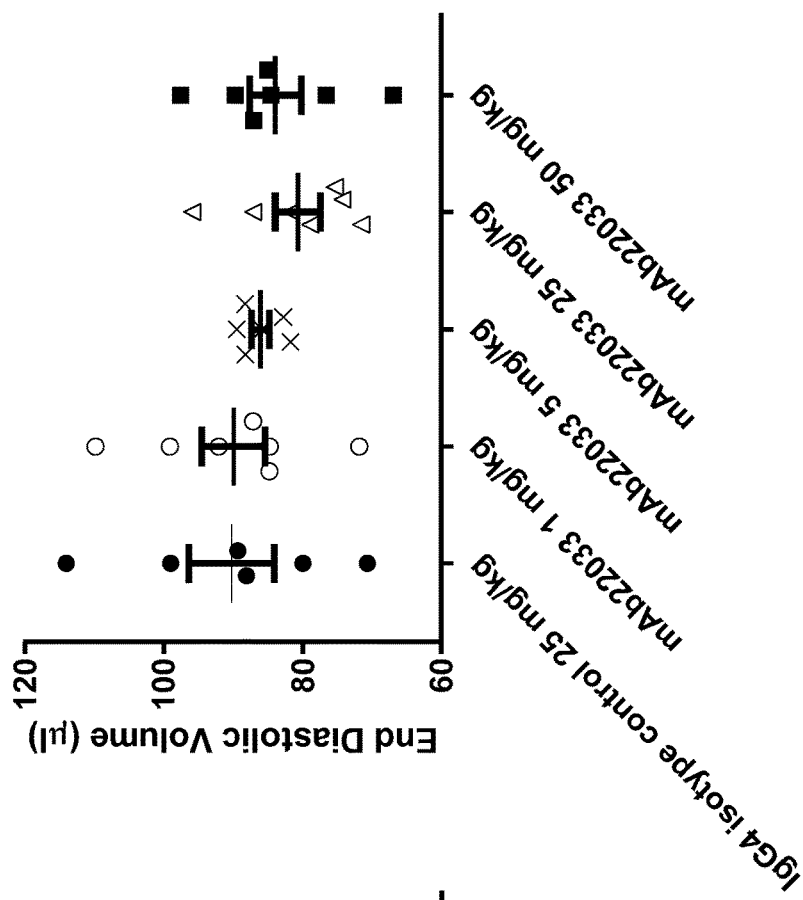
FIGS. 6A and 6B show the effect of anti-NPR1 antibody mAb22033 on left ventricular function in normotensive NPR1$^{hu/hu}$ mice.
Figure 6A:
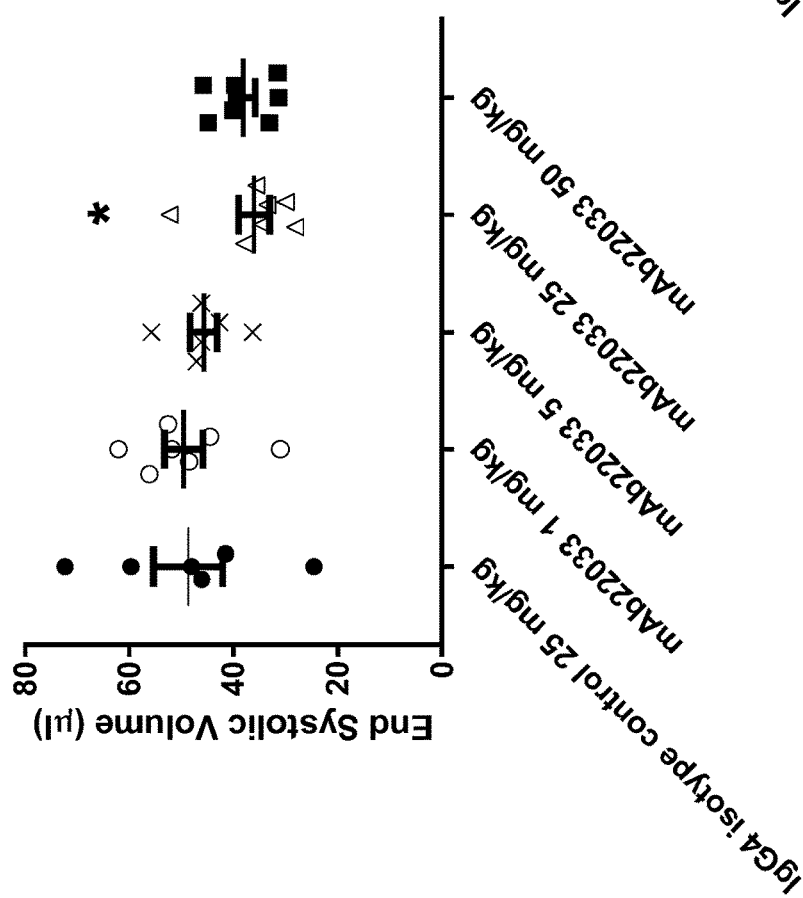
Figures 7A, 7B:
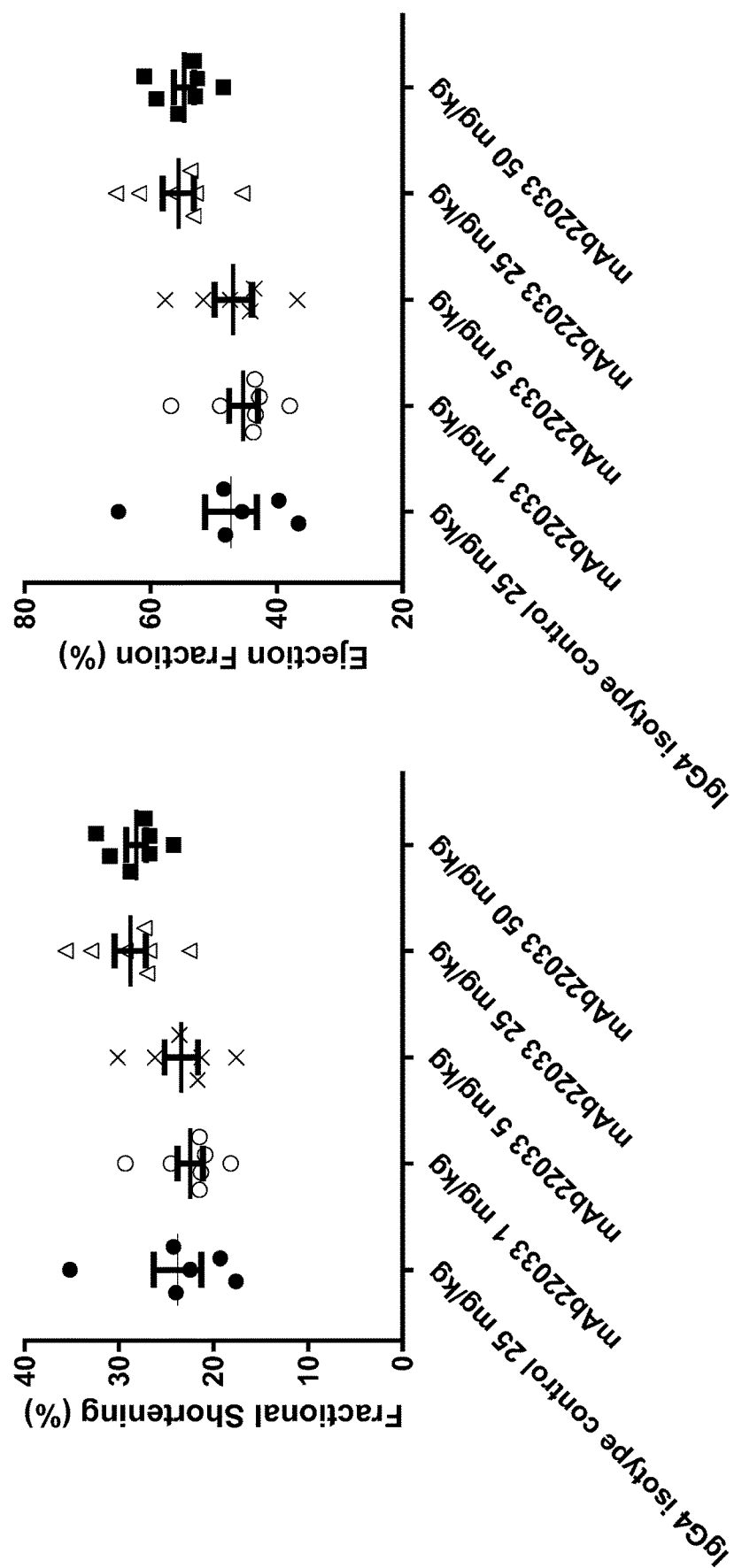
FIGS. 7A and 7B show the effect of anti-NPR1 antibody mAb22033 on left ventricular function in normotensive NPR1$^{hu/hu}$ mice.

Telemetered normotensive NPR1$^{hu/hu}$ mice were randomized into five groups of equal body weight and given a single subcutaneous injection of mAb22033 at the doses listed in Table 1. An IgG4 antibody was used as isotype control. All values are mean ± SEM, n = 6-7 per group. Statistics—one way ANOVA with Dunnett's;
*p < .05 vs. IgG4 isotype control Myocardial function (FIGS. 6 and 7A) was enhanced following administration of mAb22033, with a statistically significant reduction of end systolic volume noted in the 25 mg/kg dose group (FIG. 7A), and trending increase in both fractional shortening (FIG. 7C) and ejection fraction (FIG. 7B), most apparent in the 25 and 50 mg/kg groups.

The key findings are that the NPR1 agonist mAb, mAb22033 produced significant reductions in systolic and mean arterial blood pressures that lasted for up to 28 days. A compensatory increase in heart rate was observed in all groups initially, with a persistent minor increase in the 50 mg/kg mAb22033 dose group compared to isotype control mAb.

Example 9: Effect of a Single Dose of an Agonist Anti-NPR1 Monoclonal Antibody on Systemic Blood Pressure in Hypertensive NPR1$^{hu/hu}$ Mice Experimental Procedure The objectives of this study were to assess the effects of a single dose of an NPR1 agonist antibody (mAb22033 or mAb22810) on systemic blood pressure in telemetered angiotensin II-(Ang II)-induced hypertensive NPR1$^{hu/hu}$ mice. Male NPR1$^{hu/hu}$ (n=36) mice aged ~13 weeks were implanted with PA-C10 telemeters (DSI, St. Paul, Minn.) and allowed to recover for 7 days, prior to being assigned to group (Groups 1-6) (Table 36).

TABLE 36

Summary of doses and dose groups

| Group No. | Test or Control Article | Dose Level (mg/kg) | Dose Volume (mL/kg) | Number of Animals Males |
|---|---|---|---|---|
| 1 | IgG4 isotype control | 25 | 5 | 5 |
| 2 | mAb22033 | 1 | 5 | 4 |
| 3 | mAb22033 | 5 | 5 | 5 |

TABLE 36-continued

Summary of doses and dose groups

| Group No. | Test or Control Article | Dose Level (mg/kg) | Dose Volume (mL/kg) | Number of Animals Males |
|---|---|---|---|---|
| 4 | mAb22033 | 25 | 5 | 6 |
| 5 | mAb22810 | 5 | 5 | 5 |
| 6 | mAb22810 | 19 | 5 | 6 |

Animals were then implanted with osmotic minipumps (Alzet Micro-Osmotic Pump; Model 1004; Lot 10335-14). Minipumps were filled with Angiotensin II acetate salt (Bachem; Lot #1066804) and set to a mean pumping rate of 0.11 μL/hr for delivery of 1.5 mg/kg/day Ang II. Minipumps were implanted subcutaneously in the scapular region 3 days prior to initiation of dosing. Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

The test proteins were administered subcutaneously to the appropriate animals once on day 3 via subcutaneous injection. The dose volumes for each animal were based on the most recent body weight measurement.

Systolic pressure, diastolic pressure, mean arterial pressure, and heart rate were collected for 10 seconds every minute for the duration of the testing period. Urines were collected on day 14 and 20.

Results

Figure 8:
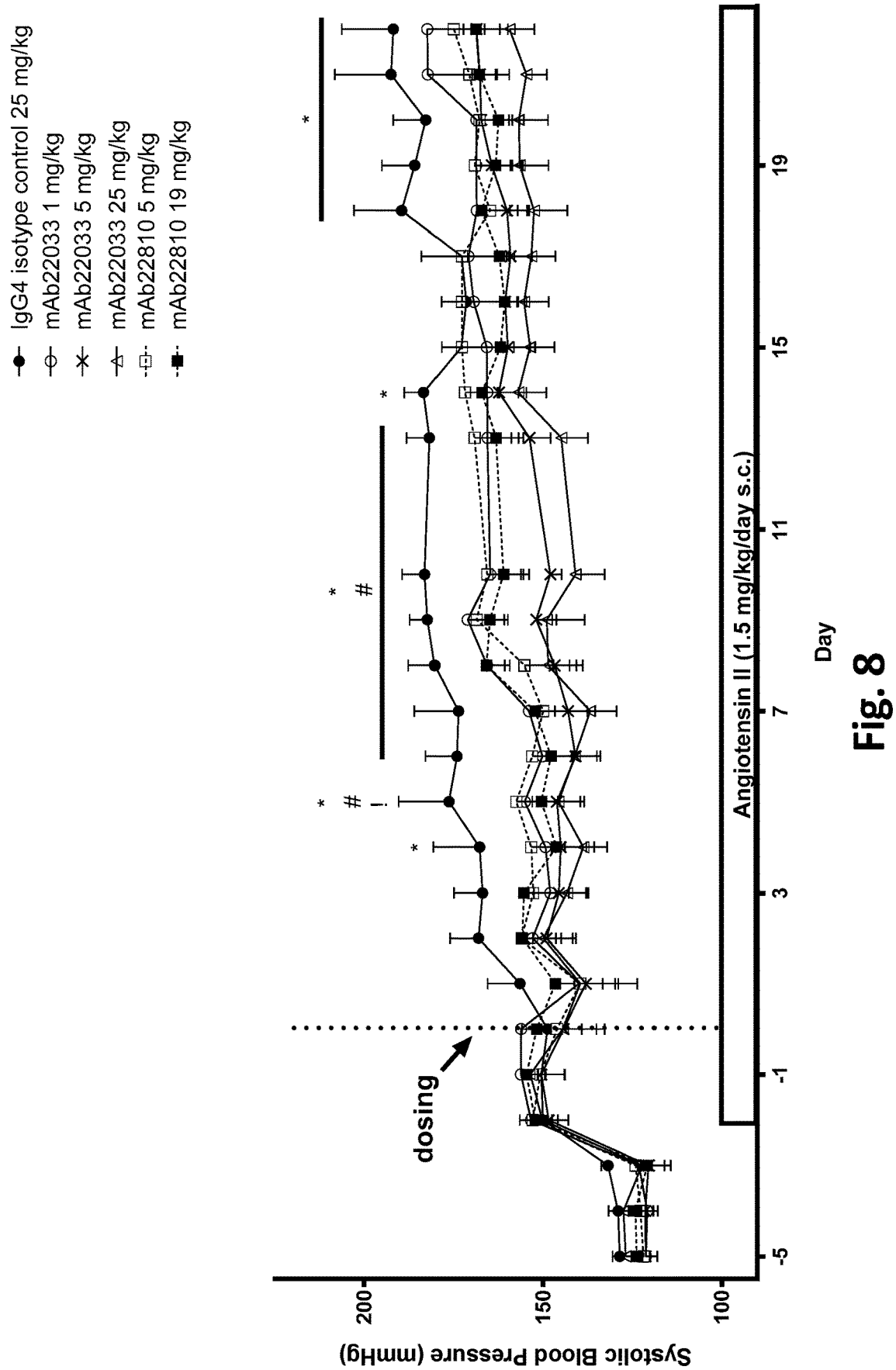
FIG. 8 shows the effect of a single dose of 2 anti-NPR1 antibodies on systolic blood pressure in hypertensive NPR1$^{hu/hu}$ mice. Telemetered hypertensive NPR1$^{hu/hu}$ mice were randomized into six groups of equal systolic blood pressures and administered a single subcutaneous dose of mAb22033 or mAb22810 at the doses listed in Table 36. An IgG4 antibody was used as isotype control. All values are mean ±SEM, n=4-6 per group. Statistics—two-way ANOVA with Dunnett's; *p<0.05 mAb22033 25 mg/kg vs. control; #p<0.05 mAb22033 5 mg/kg vs. control; !p<0.05 mAb22810 19 mg/kg vs. control.
Figure 9:
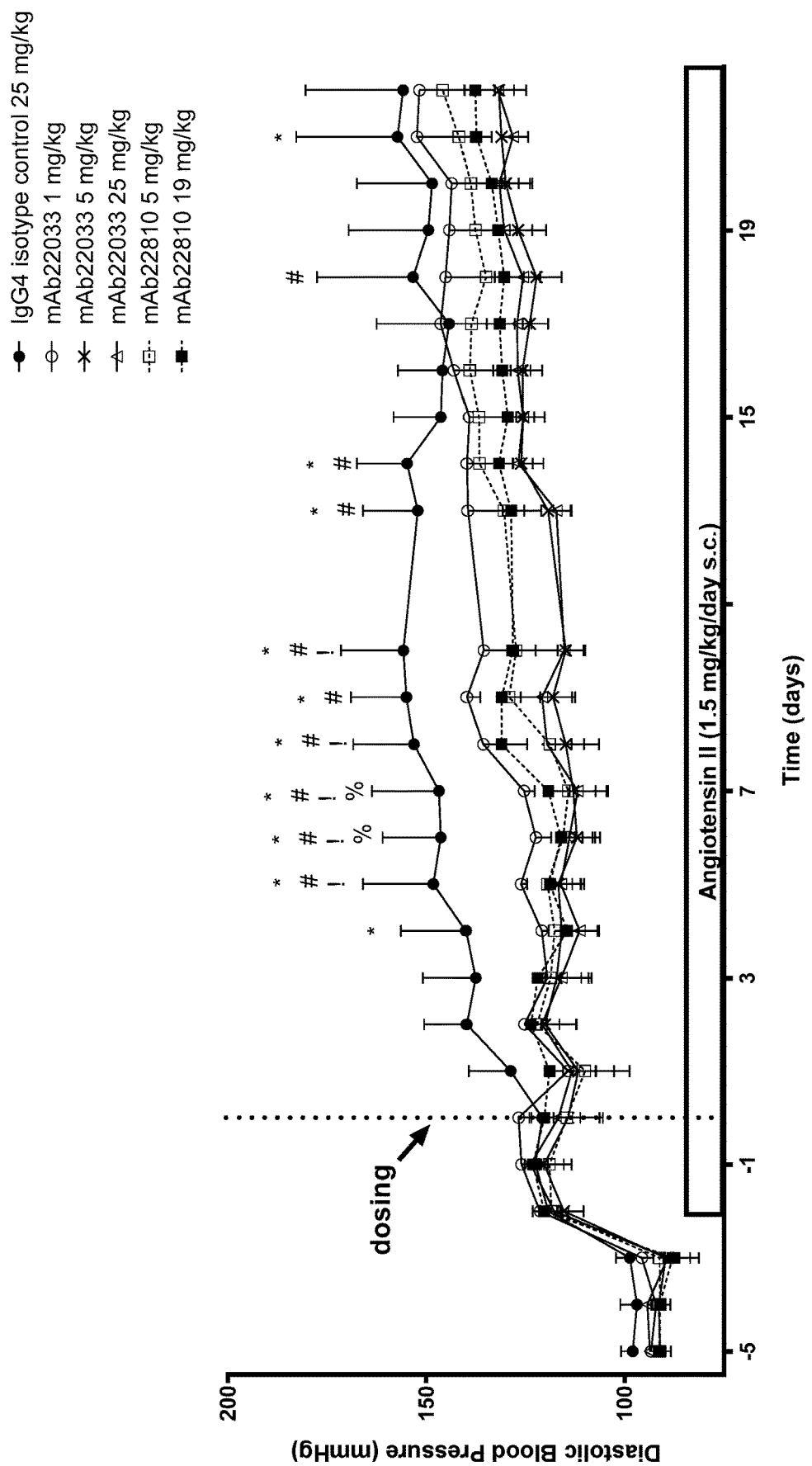
FIG. 9 shows the effect of a single dose of 2 anti-NPR1 antibodies on diastolic blood pressure in hypertensive NPR1$^{hu/hu}$ mice. Telemetered hypertensive NPR1$^{hu/hu}$ mice were randomized into six groups of equal systolic blood pressures and administered a single subcutaneous dose of mAb22033 or mAb22810 at the doses listed in Table 36. An IgG4 antibody was used as isotype control. All values are mean ±SEM, n=3-6 per group. Statistics—two-way ANOVA with Dunnett's; *p<0.05 mAb22033 25 mg/kg vs. control; #p<0.05 mAb22033 5 mg/kg vs. control; !p<0.05 mAb22810 19 mg/kg vs. control; % p<0.05 mAb22810 5 mg/kg vs. control.
Figure 11:
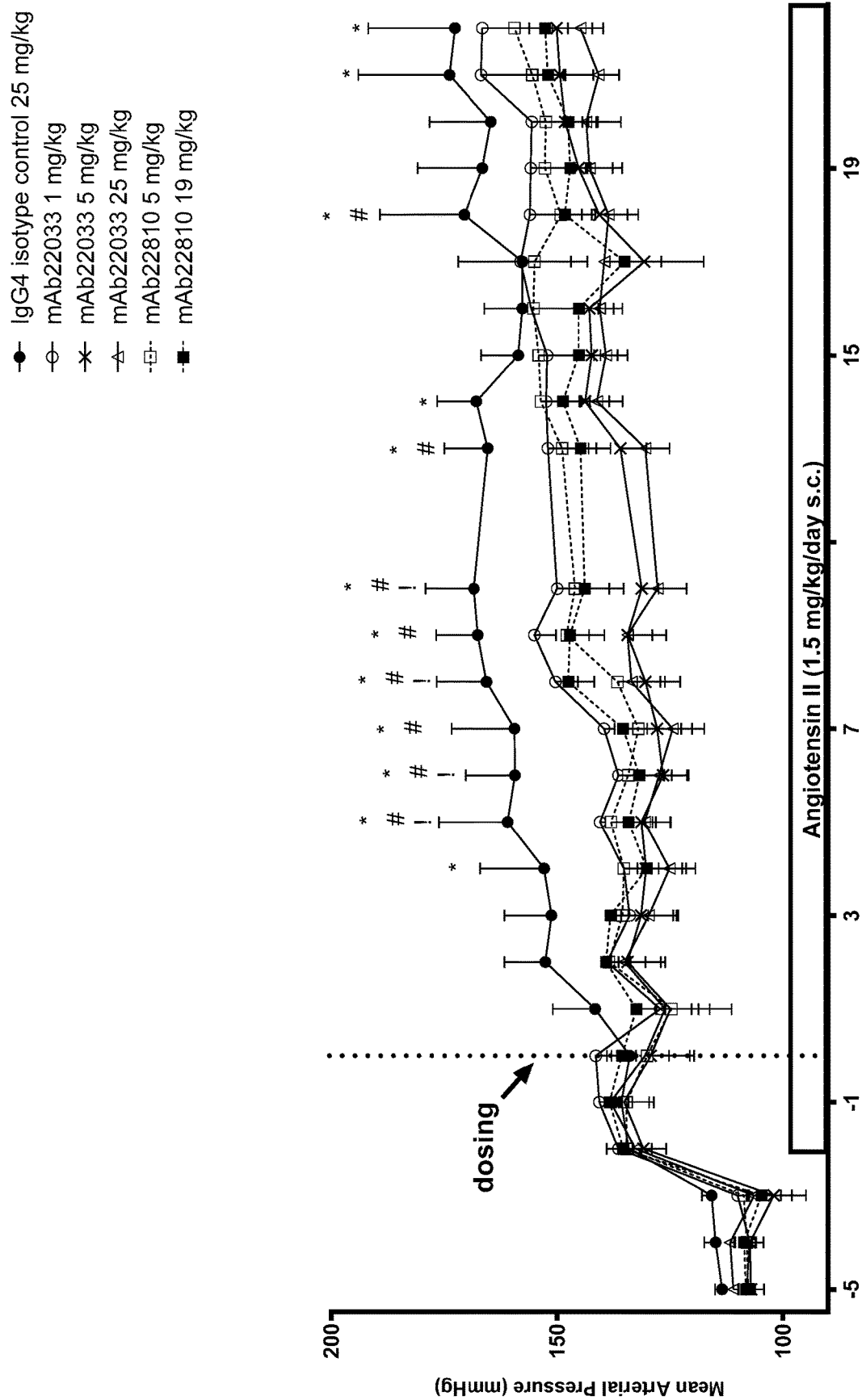
FIG. 11 shows the effect of a single dose of 2 anti-NPR1 antibodies on mean arterial blood pressure in hypertensive NPR1$^{hu/hu}$ mice. Telemetered hypertensive NPR1$^{hu/hu}$ mice were randomized into six groups of equal systolic blood pressures and administered a single subcutaneous dose of mAb22033 or mAb22810 at the doses listed in Table 36. An IgG4 antibody was used as isotype control. All values are mean ±SEM, n=3-6 per group. Statistics—two-way ANOVA with Dunnett's; *p<0.05 mAb22033 25 mg/kg vs. control; #p<0.05 mAb22033 5 mg/kg vs. control; !p<0.05 mAb22810 19 mg/kg vs. control.

A single dose of an NPR1 agonist mAb (mAb22033 or mAb22810) significantly reduced systemic blood pressures (FIGS. 8, 9 and 11) when administered to angiotensin-II-induced hypertensive NPR1$^{hu/hu}$ mice. Mean 23-day blood pressures (Table 37) were all significantly lower in animals that received either mAb22033 or mAb22810, compared to IgG4 isotype control.

TABLE 37

23-day Mean Blood Pressures and Heart Rates

| Dose Group: | Systolic (mmHg) | Diastolic (mmHg) | Mean Arterial (mmHg) | Heart Rate (BPM) |
|---|---|---|---|---|
| IgG4 isotype control (25 mg/kg) | 176 ± 2 | 147 ± 2 | 155 ± 2 | 507 ± 4 |
| mAb22033 (1 mg/kg) | 163 ± 2**** | 134 ± 2**** | 147 ± 2 | 541 ± 4**** |
| mAb22033 (5 mg/kg) | 153 ± 2**** | 120 ± 1**** | 132 ± 4**** | 547 ± 7**** |
| mAb22033 (25 mg/kg) | 149 ± 2**** | 121 ± 1**** | 131 ± 4**** | 544 ± 7**** |

TABLE 37-continued

23-day Mean Blood Pressures and Heart Rates

| Dose Group: | Systolic (mmHg) | Diastolic (mmHg) | Mean Arterial (mmHg) | Heart Rate (BPM) |
|---|---|---|---|---|
| mAb22810 (5 mg/kg) | 162 ± 2**** | 128 ± 2**** | 145 ± 2* | 532 ± 5** |
| mAb22810 (19 mg/kg) | 159 ± 2**** | 127 ± 2**** | 139 ± 3*** | 532 ± 4** |

All values are mean ± SEM, n = 3-6 per group. Statistics—two way ANOVA with Dunnett's;
*$p < .05$ vs. IgG4 isotype control;
**$p < .01$ vs. IgG4 isotype control;
***$p < 0.001$ vs. IgG4 isotype control;
****$p < .0001$ vs. IgG4 isotype control

TABLE 38

Urine and Serum Biomarkers

| Dose Group: | Urine Volume (mL/day)— Day 14 | Urinary cGMP (mmol/day)— Day 14 | Urine Volume (mL/day)— Day 20 | Urinary cGMP (mmol/day)— Day 20 | Plasma NTproANP (nmol/L)— Day 20 |
|---|---|---|---|---|---|
| IgG4 isotype control (25 mg/kg) | 2.2 ± 0.7 | 8.7 ± 2.5 | 5.2 ± 0.9 | 13.9 ± 3.1 | 0.7 ± 0.1 |
| mAb22033 (1 mg/kg) | 3.0 ± 0.7 | 13.8 ± 2.3 | 6.6 ± 0.6 | 23.4 ± 2.8 | 0.8 ± 0.2 |
| mAb22033 (5 mg/kg) | 1.3 ± 0.5 | 11.0 ± 3.2 | 3.9 ± 0.3 | 20.8 ± 0.8 | 1.0 ± 0.3 |
| mAb22033 (25 mg/kg) | 2.1 ± 0.3 | 23.5 ± 5.3* | 5.6 ± 0.8 | 44.9 ± 7.8*** | 1.5 ± 0.2 |
| mAb22810 (5 mg/kg) | 1.5 ± 0.4 | 8.3 ± 2.0 | 4.1 ± 0.8 | 19.2 ± 5.3 | 1.3 ± 0.4 |
| mAb22810 (19 mg/kg) | 2.3 ± 0.3 | 13.6 ± 1.8 | 4.9 ± 0.7 | 18.8 ± 1.9 | 1.0 ± 0.2 |

All values are mean ± SEM, n = 3-6 per group. Statistics—one way ANOVA with Dunnett's.
*$p < .05$ vs. IgG4 isotype control;
***$p < .001$ vs. IgG4 isotype control

TABLE 39

Terminal Body and Organ Weights

| Dose Group: | Terminal Body Weight (g) | Heart Weight (mg) | Heart Weight:Tibia Length | Heart Weight:Body Weight |
|---|---|---|---|---|
| IgG4 isotype control (25 mg/kg) | 29 ± 1 | 0.166 ± 0.011 | 0.0093 ± 0.0006 | 0.0057 ± 0.0003 |
| mAb22033 (1 mg/kg) | 32 ± 1 | 0.168 ± 0.005 | 0.0094 ± 0.0004 | 0.0053 ± 0.0003 |
| mAb22033 (5 mg/kg) | 29 ± 2 | 0.149 ± 0.017 | 0.0085 ± 0.0009 | 0.0051 ± 0.0005 |
| mAb22033 (25 mg/kg) | 32 ± 1 | 0.162 ± 0.008 | 0.0090 ± 0.0004 | 0.0051 ± 0.0002 |
| mAb22810 (5 mg/kg) | 30 ± 1 | 0.150 ± 0.004 | 0.0084 ± 0.0002 | 0.0050 ± 0.0001 |
| mAb22810 (19 mg/kg) | 30 ± 1 | 0.146 ± 0.015 | 0.0082 ± 0.0008 | 0.0049 ± 0.0003 |

Figure 10:
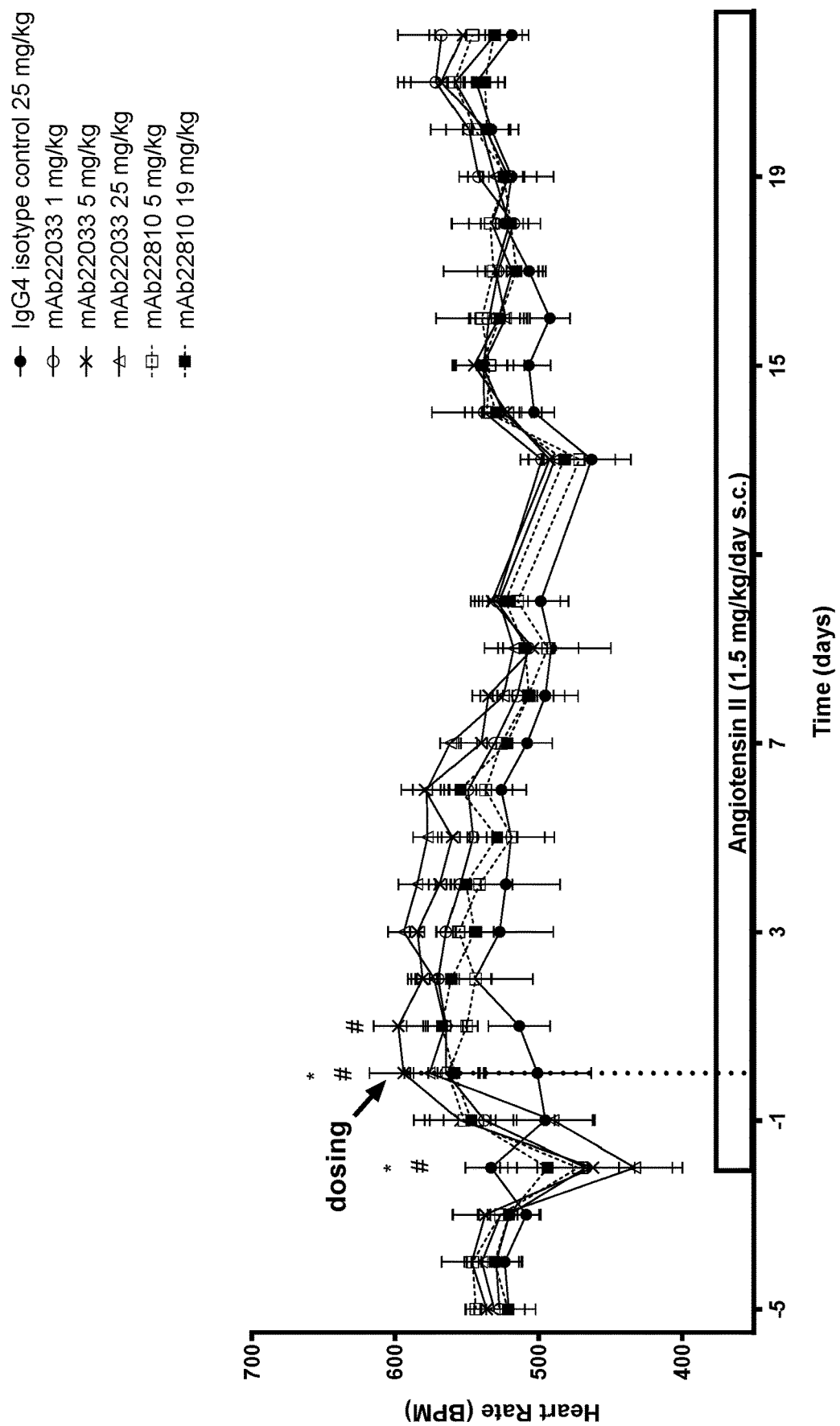
FIG. 10 shows the effect of a single dose of 2 anti-NPR1 antibodies on heart rate in hypertensive NPR1$^{hu/hu}$ mice. Telemetered hypertensive NPR1$^{hu/hu}$ mice were randomized into six groups of equal systolic blood pressures and administered a single subcutaneous dose of mAb22033 or mAb22810 at the doses listed in Table 36. An IgG4 antibody was used as isotype control. All values are mean ±SEM, n=3-6 per group. Statistics—two-way ANOVA with Dunnett's; *p<0.05 mAb22033 25 mg/kg vs. control; #p<0.05 mAb22033 5 mg/kg vs. control.

All values are mean ± SEM, n = 3-6 per group. Statistics—two way ANOVA with Dunnett's Heart rate effects (FIG. 10) were significantly increased acutely, with a more modest increase chronically. Mean 23-day heart rates (Table 37) were significantly higher across all test article-administered groups compared to isotype control animals. Urinary cGMP levels trended higher in most groups administered either mAb22033 or mAb22810, with animals in the 25 mg/kg mAb22033 having significantly increased urine cGMP levels compared to IgG isotype control animals at days 14 and 20 (Table 38). No effects on body weight or absolute or relative organ weights were observed (Table 39).

Example 10: Effect of Repeat Doses of an Agonist Anti-NPR1 Monoclonal Antibody on Systemic Blood Pressure in Hypertensive NPR1$^{hu/hu}$ Mice Experimental Procedure The objectives of this study were to assess the effects of repeat dosing of the NPR1 agonist antibody mAb22033 on systemic blood pressure in telemetered angiotensin II-(Ang II)-induced hypertensive NPR1$^{hu/hu}$ mice. Male NPR1$^{hu/hu}$ (n=30) mice aged ~26 weeks were implanted with PA-C10 telemeters (DSI, St. Paul, Minn.) and allowed to recover for 7 days, prior to being assigned to group (Groups 1-5) (Table 40).

TABLE 40

Summary of Doses and Dose Groups

| Group No. | Test or Control Article | Dose Level (mg/kg/dose) | Dose Volume (mL/kg) | Number of Animals Males |
|---|---|---|---|---|
| 1 | IgG4 isotype control | 25 | 5 | 6 |
| 2 | mAb22033 | 1 | 5 | 6 |
| 3 | mAb22033 | 5 | 5 | 6 |

TABLE 40-continued

Summary of Doses and Dose Groups

| Group No. | Test or Control Article | Dose Level (mg/kg/dose) | Dose Volume (mL/kg) | Number of Animals Males |
|---|---|---|---|---|
| 4 | mAb22033 | 25 | 5 | 6 |
| 5 | mAb22033 | 50* | 5 | 6 |

*single dose

Animals were then implanted with osmotic minipumps (Alzet Micro-Osmotic Pump; Model 1004; Lot 10335-14). Minipumps were filled with Angiotensin II acetate salt (Bachem; Lot #1066804) and set to a mean pumping rate of 0.11 µL/hr for delivery of 1.5 mg/kg/day Ang II. Minipumps were implanted subcutaneously in the scapular region 7 days prior to initiation of dosing. Animals were individually housed under standard conditions (Temperatures of 64° F. to 84° F. (18° C. to 29° C.); relative humidity of 30% to 70%) and a 12-hour light/12-hour dark cycle was maintained. Food (Research Diets Standard pellet chow) and water were provided ad libitum.

Animals were stratified to group based off of systolic blood pressures. The test proteins were administered to the appropriate animals either once on day 0 (Group 5) or twice weekly for three weeks (Groups 1-4) beginning on day 6 via subcutaneous injection. The dose volumes for each animal were based on the most recent body weight measurement.

Systolic pressure, diastolic pressure, mean arterial pressure, and heart rate were collected for 10 seconds every minute for the duration of the testing period.

Results

Figure 12:
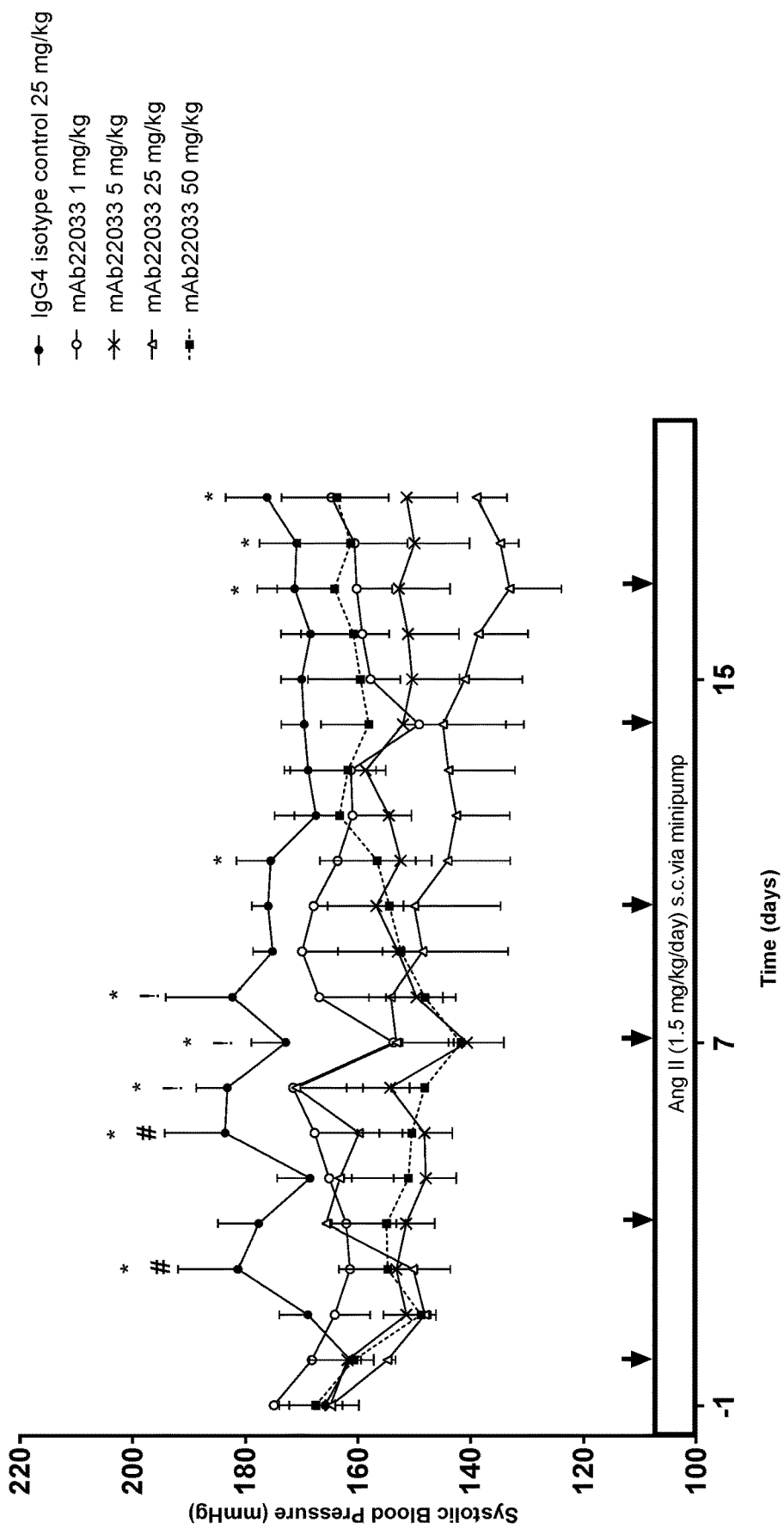
FIG. 12 shows the effect of single and repeated doses of an anti-NPR1 antibody on systolic blood pressure in hypertensive NPR1$^{hu/hu}$ mice. Telemetered hypertensive NPR1$^{hu/hu}$ mice were randomized into five groups of equal systolic blood pressures and administered either a single subcutaneous dose or twice weekly for 3 weeks of mAb22033 at the doses listed in Table 40. An IgG4 antibody was used as isotype control. All values are mean ±SEM, n=3-6 per group. The arrows represent the doses administered to the mice. Statistics—two-way ANOVA with Dunnett's; *p<0.05 mAb22033 25 mg/kg vs. control; #p<0.05 mAb22033 5 mg/kg vs. control; !p<0.05 mAb22033 50 mg/kg vs. control.
Figure 13:
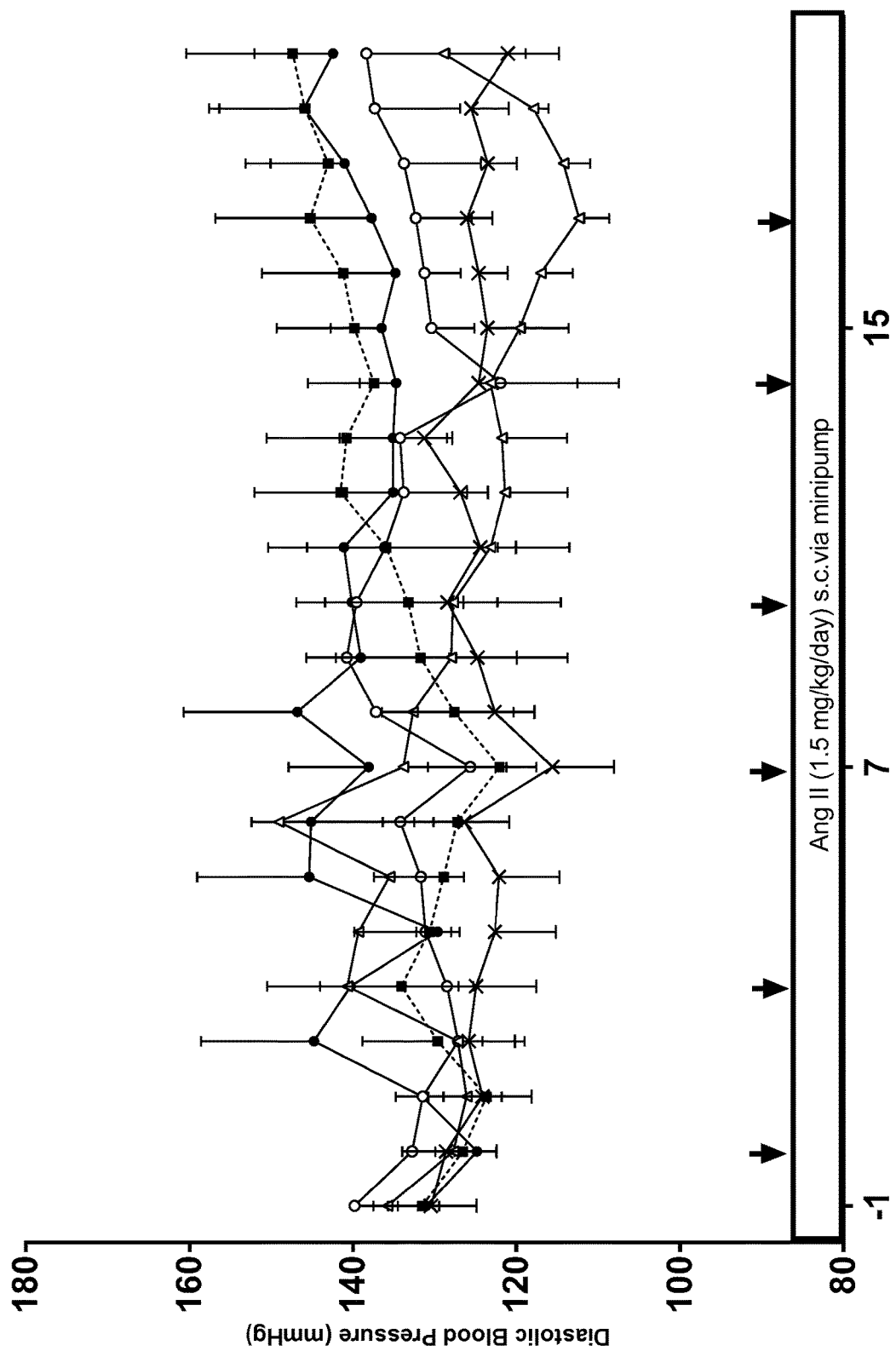
FIG. 13 shows the effect of single and repeated doses of an anti-NPR1 antibody on diastolic blood pressure in hypertensive NPR1$^{hu/hu}$ mice. Telemetered hypertensive NPR1$^{hu/hu}$ mice were randomized into five groups of equal systolic blood pressures and administered either a single subcutaneous dose or twice weekly for 3 weeks of mAb22033 at the doses listed in Table 40. An IgG4 antibody was used as isotype control. All values are mean ±SEM, n=3-6 per group. The arrows represent the doses administered to the mice. Statistics—two-way ANOVA with Dunnett's.
Figure 15:
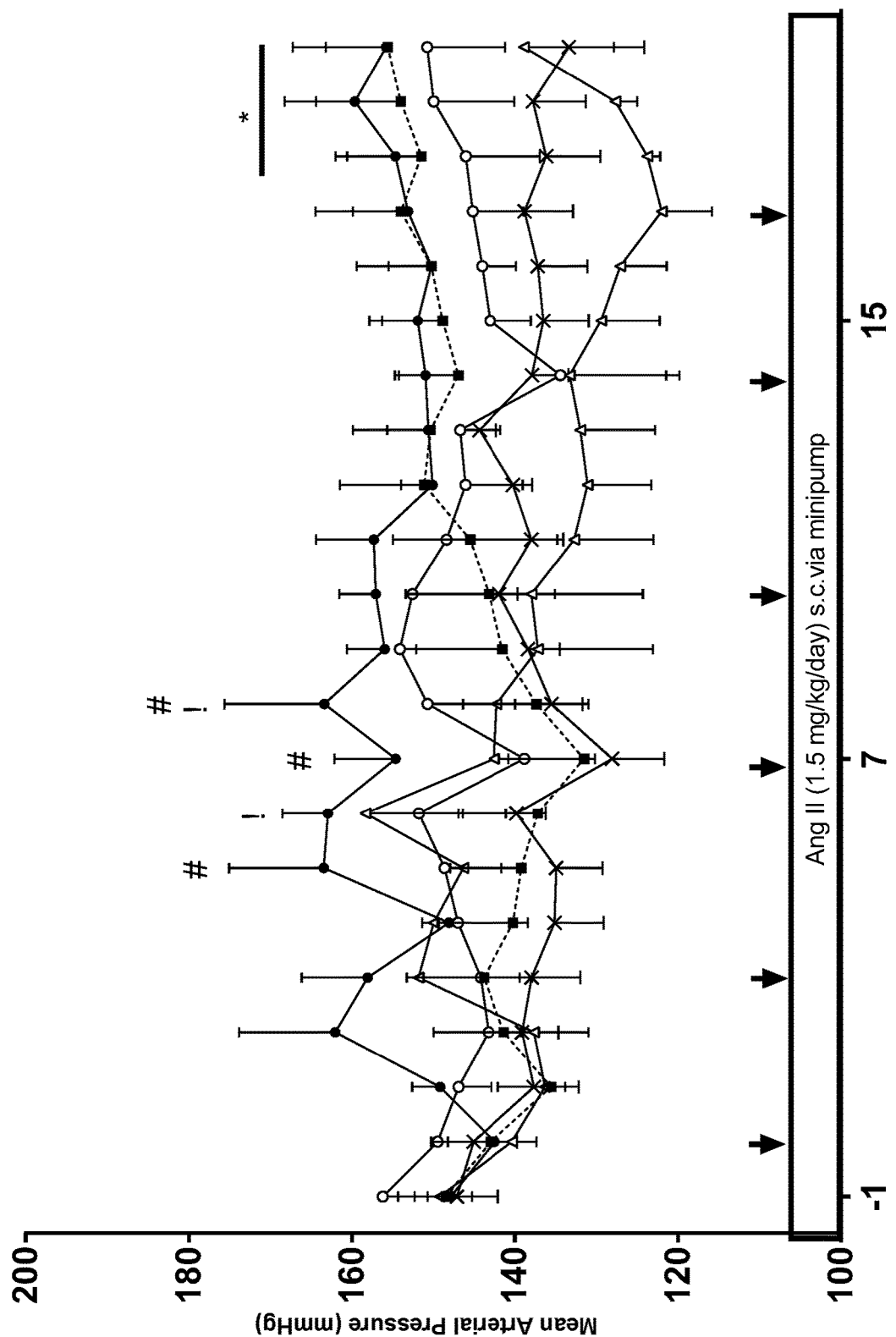
FIG. 15 shows the effect of single and repeated doses of an anti-NPR1 antibody on mean arterial blood pressure in hypertensive NPR1$^{hu/hu}$ mice. Telemetered hypertensive NPR1$^{hu/hu}$ mice were randomized into five groups of equal systolic blood pressures and administered either a single subcutaneous dose or twice weekly for 3 weeks of mAb22033 at the doses listed in Table 40. An IgG4 antibody was used as isotype control. All values are mean ±SEM, n=3-6 per group. The arrows represent doses administered to the mice. Statistics—two-way ANOVA with Dunnett's; *p<0.05 mAb22033 25 mg/kg vs. control; #p<0.05 mAb22033 5 mg/kg vs. control; !p<0.05 mAb22033 50 mg/kg vs. control.

Single or repeat doses of the NPR1 agonist mAb mAb22033 reduced systemic blood pressures (FIGS. 12, 13 and 15) back to near normotensive levels in angiotensin-II-induced hypertensive NPR1$^{hu/hu}$ mice. Repeated doses of 1, 5 or 25 mg/kg mAb22033 dose-dependently reduced systolic blood pressures, with peak reductions relative to individual group baselines of 11, 19 and 39 mmHg, respectively after three weeks of twice weekly dosing. A single dose of 50 mg/kg reduced systolic blood pressure 31 mmHg by day 7, with a gradual return to more hypertensive levels thereafter. Mean 21-day blood pressures (Table 41) were all significantly lower in animals that received either single or repeated doses of mAb22033, compared to IgG4 isotype control.

TABLE 41

21-day Mean Blood Pressures and Heart Rates

| Dose Group: | Systolic (mmHg) | Diastolic (mmHg) | Mean Arterial (mmHg) | Heart Rate (BPM) |
|---|---|---|---|---|
| IgG4 isotype control (25 mg/kg) | 173.4 ± 1.3 | 138.6 ± 0.7 | 154.9 ± 1.2 | 538.2 ± 1.8 |
| mAb22033 (1 mg/kg) | 163.0 ± 1.2** | 132.9 ± 1.0 | 146.8 ± 1.0** | 532.5 ± 3.2 |
| mAb22033 (5 mg/kg) | 151.9 ± 0.9**** | 124.7 ± 0.7**** | 137.8 ± 0.8**** | 524.8 ± 3.5** |
| mAb22033 (25 mg/kg) | 149.1 ± 2.2**** | 127.0 ± 2.0*** | 137.1 ± 2.0**** | 511.3 ± 2.9**** |
| mAb22033 (50 mg/kg)*single dose* | 156.2 ± 1.4**** | 135.0 ± 1.7 | 144.9 ± 1.5**** | 552.4 ± 3.1** |

All values are mean ± SEM, n = 3-6 per group. Statistics—two way ANOVA with Dunnett's;
**p < .01 vs. IgG4 isotype control;
***p < .001 vs. IgG4 isotype control;
****p < .0001 vs. IgG4 isotype control

TABLE 42

Terminal Body and Organ Weights

| Dose Group: | Terminal Body Weight (g) | Heart Weight (mg) | Heart Weight: Tibia Length | Heart Weight: Body Weight |
|---|---|---|---|---|
| IgG4 isotype control (25 mg/kg) | 30.9 ± 1.5 | 0.165 ± 0.006 | 0.0091 ± 0.00032 | 0.0054 ± 0.0002 |
| mAb22033 (1 mg/kg) | 31.1 ± 1.1 | 0.151 ± 0.007 | 0.0084 ± 0.00043 | 0.0049 ± 0.0002 |
| mAb22033 (5 mg/kg) | 29.6 ± 1.0 | 0.149 ± 0.004 | 0.0082 ± 0.00020 | 0.0050 ± 0.0001 |
| mAb22033 (25 mg/kg) | 32.4 ± 1.9 | 0.165 ± 0.012 | 0.009 ± 0.00067 | 0.0051 ± 0.0003 |
| mAb22033 (50 mg/kg)* single dose* | 31.0 ± 1.3 | 0.153 ± 0.006 | 0.0085 ± 0.00034 | 0.0050 ± 0.0003 |

All values are mean ± SEM,
n = 3-6 per group.
Statistics-one way ANOVA with Dunnett's

TABLE 43

Urine and Serum Markers

| Dose Group: | Urine Volume (mL/day) | Urinary cGMP (mmol/day) | Serum NTproANP (nmol/L)-Day 20 | Serum NTproANP (nmol/L)-Day 29 |
|---|---|---|---|---|
| IgG4 isotype control (25 mg/kg) | 2.74 ± 0.74 | 30.5 ± 6.3 | 0.58 ± 0.05 | 0.57 ± 0.09 |
| mAb22033 (1 mg/kg) | 3.08 ± 0.51 | 61.6 ± 20.4 | 0.75 ± 0.03 | 0.51 ± 0.05 |
| mAb22033 (5 mg/kg) | 2.48 ± 0.68 | 36.6 ± 10.4 | 0.45 ± .013 | 0.36 ± 0.08 |
| mAb22033 (25 mg/kg) | 3.2 ± 0.80 | *106.3 ± 25.4* | 0.59 ± 0.13 | 0.63 ± 0.14 |
| mAb22033 (50 mg/kg)* single dose* | 3.27 ± 0.89 | 52.8 ± 21.5 | 0.56 ± 0.18 | 1.27 ± 0.43 |

Figure 14:
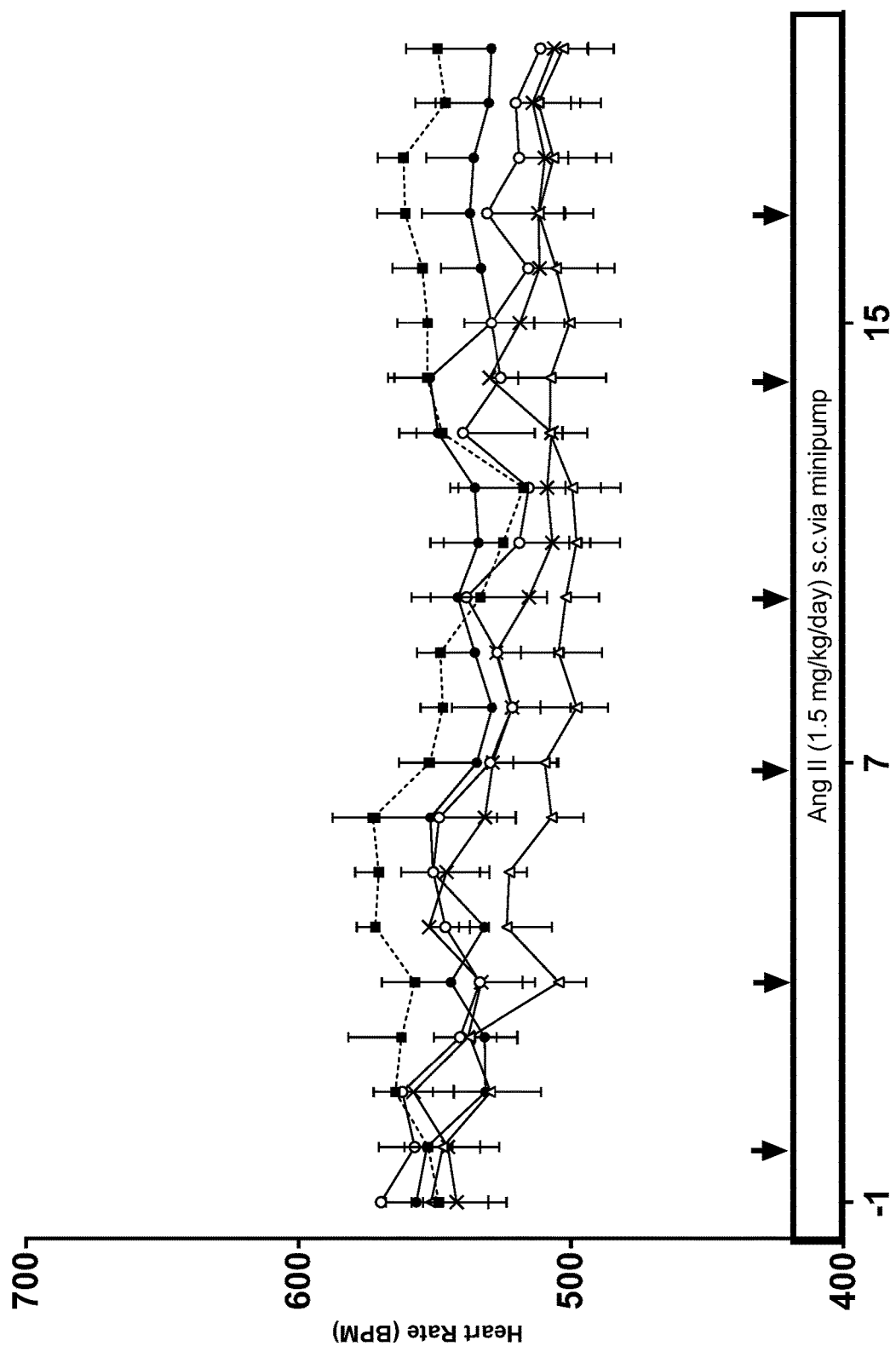
FIG. 14 shows the effect of single and repeated doses of an anti-NPR1 antibody on heart rate in hypertensive NPR1$^{hu/hu}$ mice. Telemetered hypertensive NPR1$^{hu/hu}$ mice were randomized into five groups of equal systolic blood pressures and administered either a single subcutaneous dose or twice weekly for 3 weeks of mAb22033 at the doses listed in Table 40. An IgG4 antibody was used as isotype control. All values are mean ±SEM, n=3-6 per group. The arrows represent doses administered to the mice. Statistics—two-way ANOVA with Dunnett's.
Figure 16A:
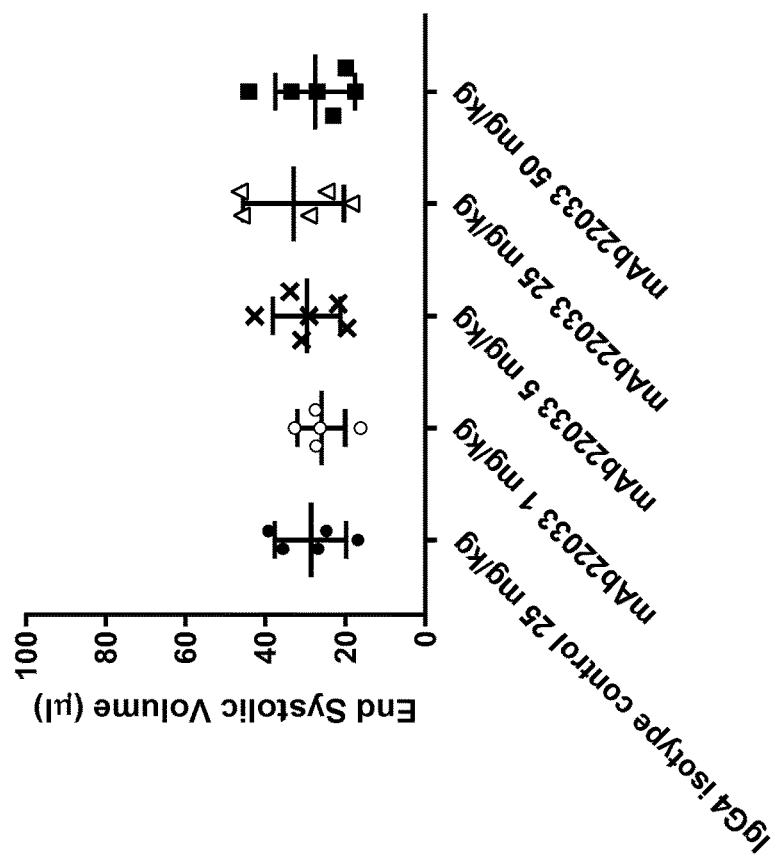
FIGS. 16A and 16B show the effects of single and repeated doses of an anti-NPR1 antibody on cardiac function in hypertensive NPR1$^{hu/hu}$ mice.
Figure 16B:
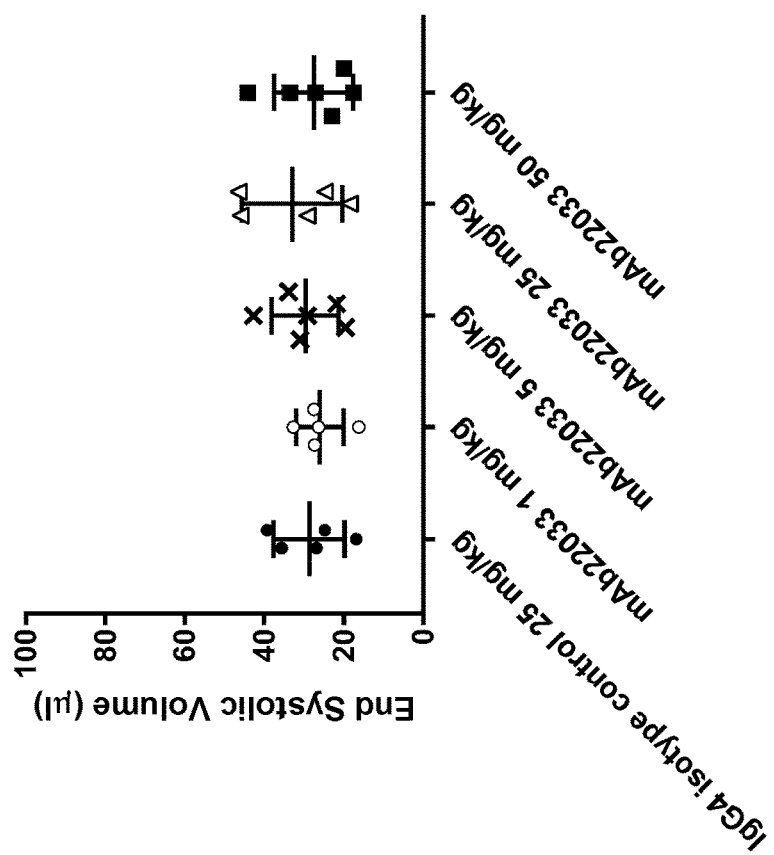
Figure 17B:
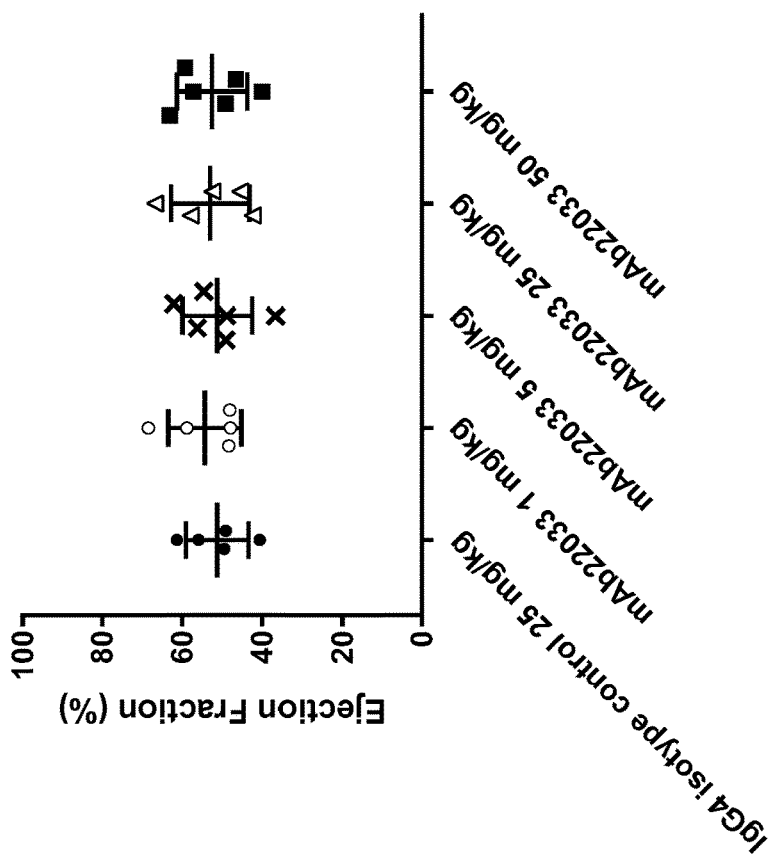
FIGS. 17A and 17B show the effects of single and repeated doses of an anti-NPR1 antibody on cardiac function in hypertensive NPR1$^{hu/hu}$ mice.
Figure 17A:
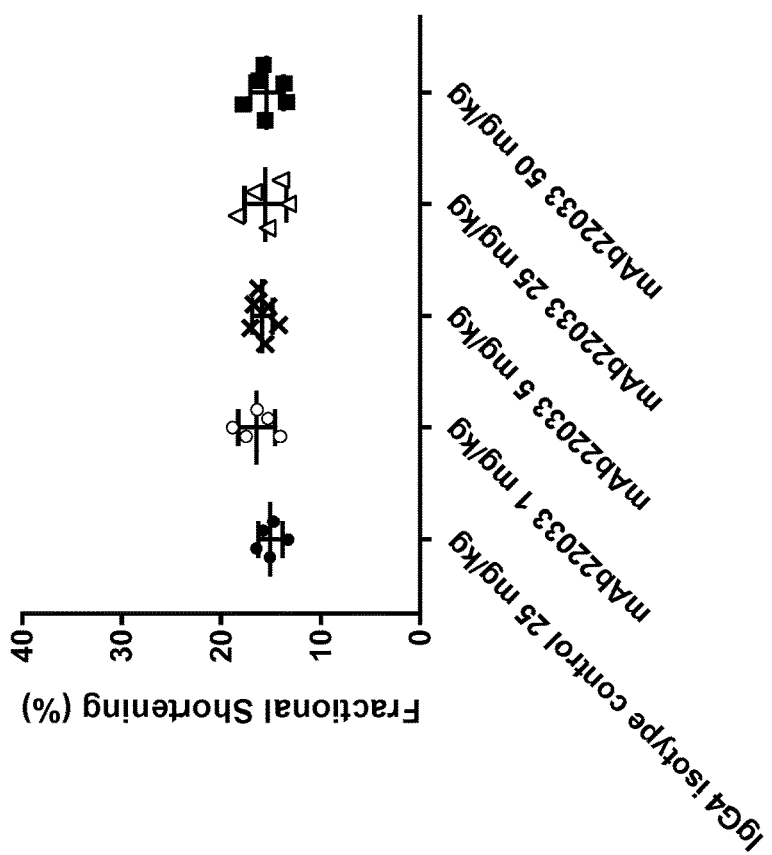

All values are mean ± SEM,
n = 3-6 per group.
Statistics-one way ANOVA with Dunnett's.
*p < .05 vs. IgG4 isotype control Acute effects of mAb22033 were analyzed, with pressure reductions of 10-20 mmHg within 24 hours of the first dose. Heart rate effects (FIG. 14) were variable, with higher and lower values being observed over the 21-day dosing period. Mean 21-day heart rates (Table 41) were significantly lower in the 5 and 25 mg/kg repeat dose groups, and trended higher in the single 50 mg/kg dose group. Urinary cGMP levels were significantly increased in the 25 mg/kg repeat dose group, with all other groups showing trending, non-statistically significant increases compared to IgG4 isotype control mAb dosed animals (Table 43). No effects on body weight, absolute or relative organ weights, standard serum or urine chemistries or cardiac function were observed (Table 42 and FIGS. 16-17).

Example 11: Effect of Anti-NPR1 Agonist Antibodies on Body Weight, Metabolic Rate and Glucose Homeostasis in Diet-Induced Obese (DIO) Mice Experiment 1

In this experiment, the effect of mAb22810 NPR1 agonist mAb on body weight, metabolic rate and glucose homeostasis in diet-induced obese (DIO) mice was tested.

Thirty, male NPR1$^{hu/hu}$ mice were placed on a 60% high-fat diet for 10 weeks, then randomized into three groups (n=10 per group): Isotype control (human IgG4) antibody, NPR1 agonist antibody mAb22810 or hFc.FGF21. FGF21 is a molecule that has been proven to improve glucose tolerance, increase energy expenditure and lower body weight in obese mice models (Véniant MM, Endocrinology, 2012, PMID: 22798348). It was used as a positive control in this study for the endpoints. Treatments were administered in saline vehicle by subcutaneous injection (S.C.) either weekly (for the control antibody and mAb22810) or twice weekly (for hFc.FGF21). Table 44 lists the groups, number of animals and doses in the study.

TABLE 44

Summary of treatment groups

| Group | Treatment | Dose | Dosing Schedule | Mice |
|---|---|---|---|---|
| 1 | Control mAb | 25 mg/kg | 1×/week, S.C. | 10 |
| 2 | mAb22810 | 25 mg/kg | 1×/week, S.C. | 10 |
| 3 | hFc.FGF21 | 3.2 mg/kg | 2×/week, S.C. | 10 |

Individual body weights were recorded prior to dosing and twice per week thereafter. During the second week of the study, mice were put into metabolic cages to assess energy expenditure. Oral glucose tolerance was assessed during the third week of the study and body composition was measured after six weeks of treatment by EchoMRI.

Figure 18A:
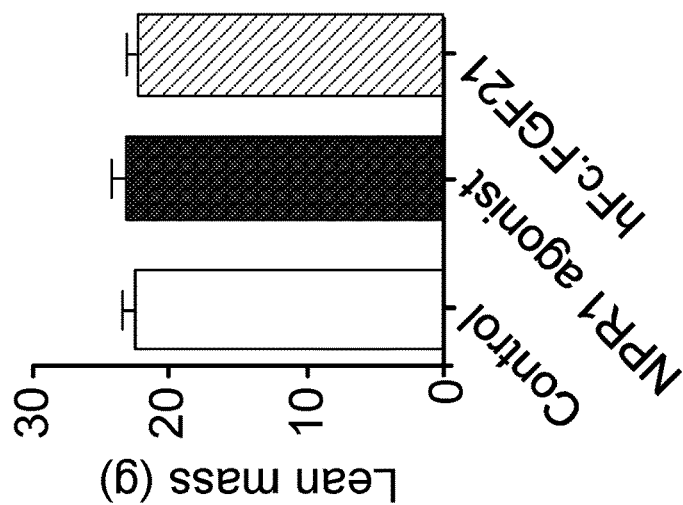
FIG. 18A shows changes in body weight following administration of mAb22810 NPR1 agonist mAb, hFc.FGF21 or an isotype control mAb.
Figure 18B:
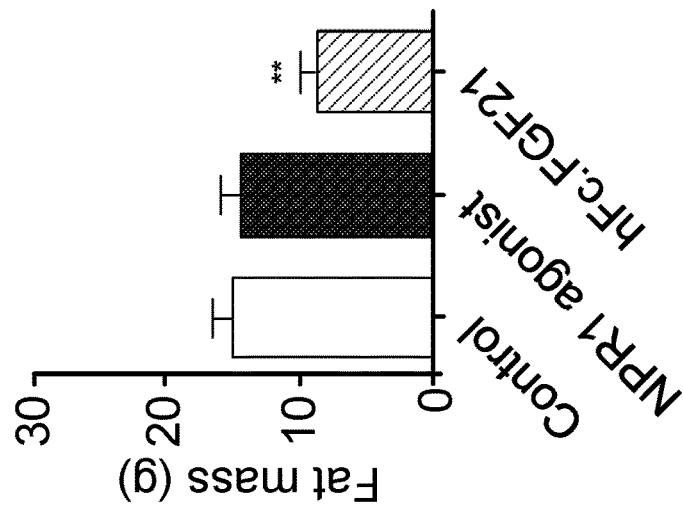
FIG. 18B and FIG. 18C show total fat and total lean mass, respectively, after six weeks of treatment as measured by EchoMRI. NPR1 humanized mice were made obese by placing them on a 60% high-fat diet for 10 weeks. Following this period, mice were randomized into three groups of equal body weight and given a subcutaneous injection of treatments at the doses and frequencies listed in Table 44. A human IgG4 antibody was used as isotype control. All values are mean ±SEM, n=10 per group. *=P<0.05 vs isotype control; **=P<0.01 vs isotype control. Statistics by two-way ANOVA+Tukey for the body weights, one-way ANOVA+Bonferonni for the fat and lean mass.
Figure 18C:
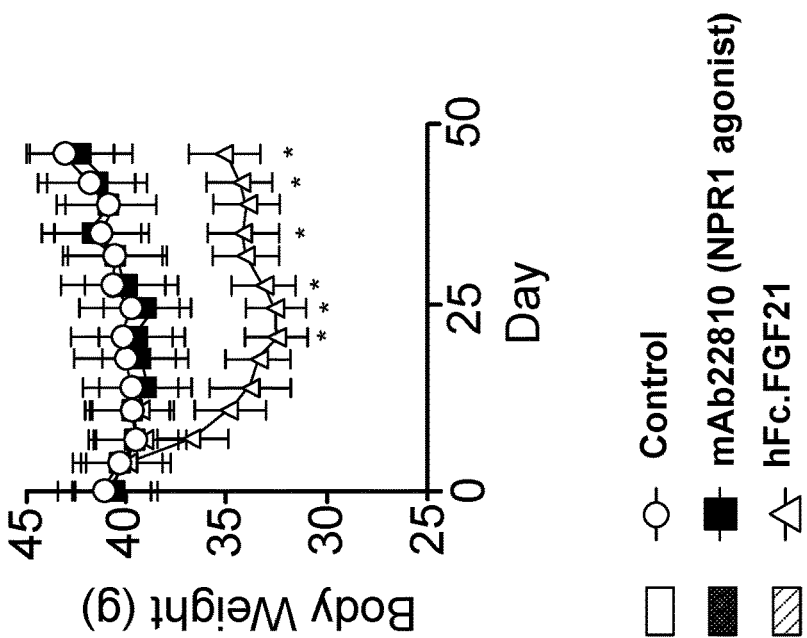

FIG. 18A shows changes in body weight following administration of mAb22810 NPR1 agonist mAb, hFc.FGF21 or an isotype control mAb. FIG. 18B and FIG. 18C show total fat and total lean mass respectively after six weeks of treatment as measured by EchoMRI. The key findings are that while the hFc.FGF21 molecule produced significant reductions in body weight and adiposity over the treatment period, the mAb22810 NPR1 agonist antibody did not.

Figure 19C:
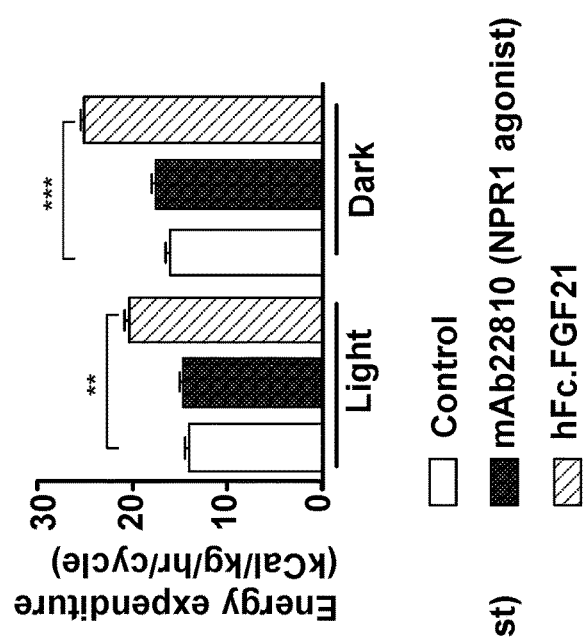
FIGS. 19A, 19B, and 19C show changes in VO$_2$ (FIG. 19A), VCO$_2$ (FIG. 19B) or Energy Expenditure (FIG. 19C) broken down as the average of each day/night cycle after one week of treatment with either mAb22810 NPR1 agonist mAb, hFc.FGF21 or an isotype control mAb. After one week of treatment, mice from each group were placed in a Columbia Instruments metabolic cage system (CLAMS) for one week to record metabolic parameters. Mice were acclimated to the cages for one week prior to measurement to minimize stress. A human IgG4 antibody was used as isotype control. All values are mean ±SEM, n=5-6 per group. =P<0.01 vs isotype control, *=P<0.001 vs isotype control. Statistics by one-way ANOVA+Bonferonni.
Figure 19B:
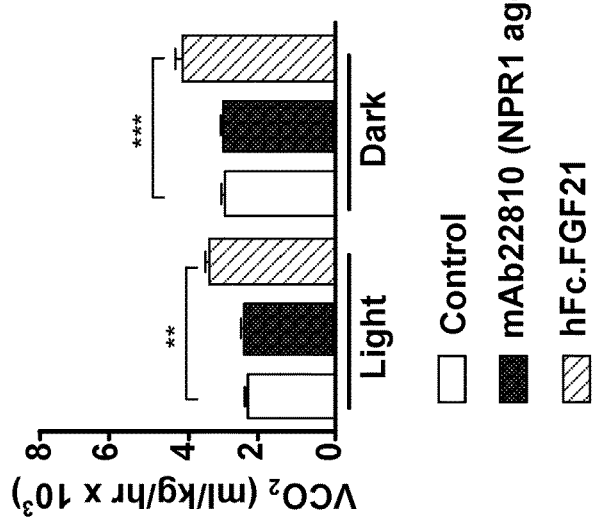
Figure 19A:
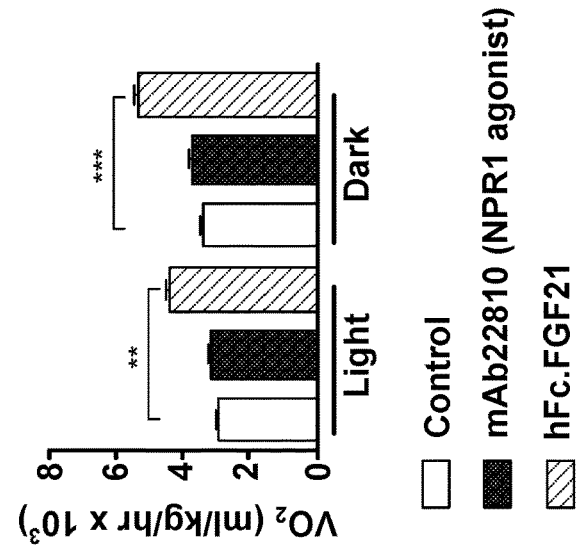

FIGS. 19A-C show changes in VO$_2$ (A), VCO$_2$ (B) or Energy Expenditure (C) broken down as the average of each day/night cycle after one week of treatment with either mAb22810 NPR1 agonist mAb, hFc.FGF21 or an isotype control mAb. The key findings are that while the hFc.FGF21 molecule produced significant increases in VO$_2$, VCO$_2$ and energy expenditure over the treatment period, the mAb22810 NPR1 agonist antibody did not.

Figure 20B:
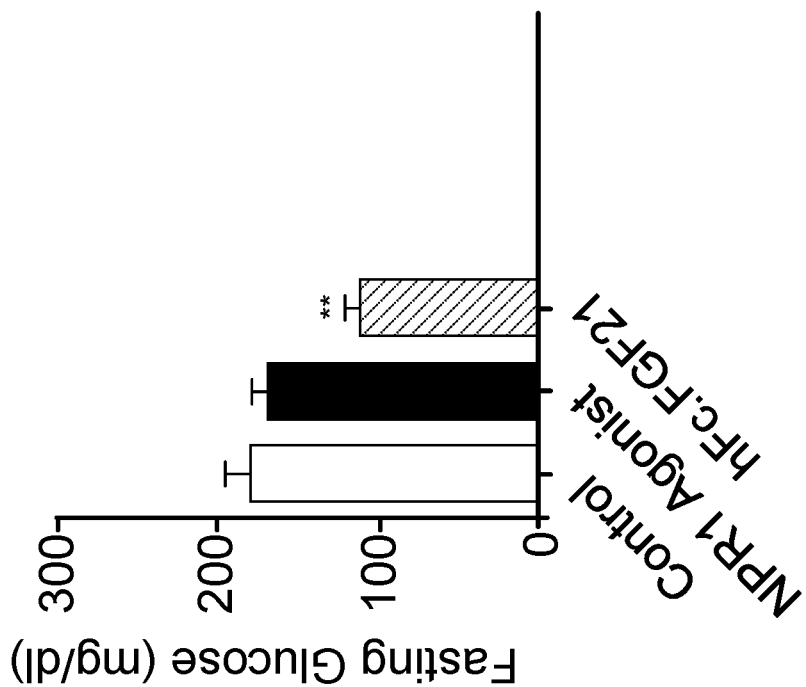
FIG. 20B shows glucose levels following an overnight fast as recorded at the start of the study in A. After two weeks of treatment, mice from each group were fasted overnight in clean cages and given an oral glucose load of 2 g/kg the following morning. Glucose was then recorded by tail vein using a hand-held glucometer at T0, T15, T30, T60, T90 and T120. A human IgG4 antibody was used as isotype control. All values are mean ±SEM, n=10 per group. hFc.FGF21 group: =P<0.01 vs isotype control, *=P<0.001 vs isotype control, ****=P<0.0001 vs isotype control. mAb22810 group: ++=P<0.01 vs isotype control. Statistics by two-way ANOVA+Bonferonni for the oGTT, one-way ANOVA+Bonferonni for the fasting glucose.
Figure 20A:
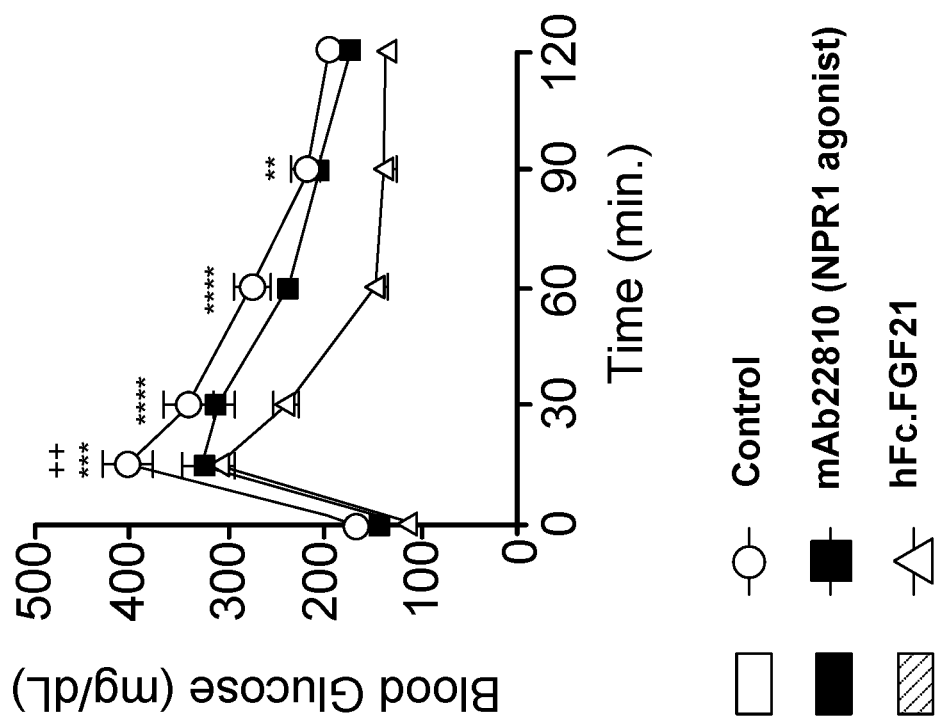
FIG. 20A shows changes in glucose tolerance as measured by an oral glucose tolerance test (2 g/kg glucose) after two weeks of treatment with either mAb22810 NPR1 agonist mAb, hFc.FGF21 or an isotype control mAb.

FIG. 20A shows changes in glucose tolerance as measured by an oral glucose tolerance test (2 g/kg glucose) after two weeks of treatment with either mAb22810 NPR1 agonist mAb, hFc.FGF21 or an isotype control mAb. FIG. 20B shows glucose levels following an overnight fast as recorded at the start of the study in A. The key findings are that both the mAb22810 and hFc.FGF21 molecules produced significant improvements in glucose tolerance after two weeks. Furthermore, the improvement in glucose tolerance by mAb22810 was independent of changes in body weight or energy expenditure (as shown in FIGS. 18 and 19).

Experiment 2

This experiment describes the effect of mAb22033 NPR1 agonist mAb on body weight, metabolic rate and glucose homeostasis in diet-induced obese (DIO) mice.

Thirty, male NPR1$^{hu/hu}$ mice were placed on a 60% high-fat diet for 10 weeks, then randomized into three groups (n=10 per group): Isotype control (human IgG4) antibody, NPR1 agonist antibody mAb22033 or hFc.FGF21 as a positive control. Treatments were administered in saline vehicle by subcutaneous injection (S.C.) either weekly (for the control antibody and mAb22033) or twice weekly (for hFc.FGF21). Table 45 lists the groups, number of animals and doses in the study.

TABLE 45

Summary of treatment groups

| Group | Treatment | Dose | Dosing Schedule | Mice |
|---|---|---|---|---|
| 1 | Control mAb | 25 mg/kg | 1×/week, S.C. | 10 |
| 2 | mAb22033 | 25 mg/kg | 1×/week, S.C. | 10 |
| 3 | hFc.FGF21 | 3.2 mg/kg | 2×/week, S.C. | 10 |

Individual body weights were recorded prior to dosing and twice per week thereafter. During the second week of the study, mice were put into metabolic cages to assess energy expenditure. Oral glucose tolerance was assessed during the fourth week of the study and body composition was measured after six weeks of treatment by EchoMRI.

Figure 21C:
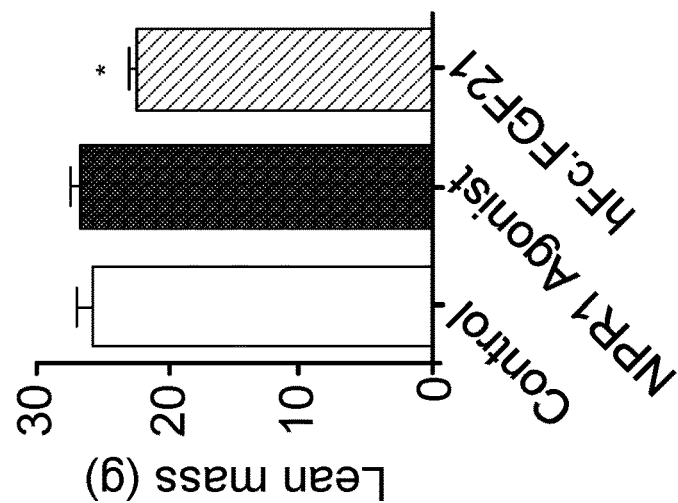
FIG. 21B and FIG. 21C show total fat and total lean mass respectively after six weeks of treatment as measured by EchoMRI. NPR1 humanized mice were made obese by placing them on a 60% high-fat diet for 10 weeks. Following this period, mice were randomized into three groups of equal body weight and given a subcutaneous injection of treatments at the doses and frequencies listed in Table 45. A human IgG4 antibody was used as isotype control. All values are mean ±SEM, n=10 per group. *=P<0.05 vs isotype control, ****=P<0.0001 vs isotype control. Statistics by two-way ANOVA+Tukey for the body weights, one-way ANOVA+Bonferonni for the fat and lean mass.
Figure 21B:
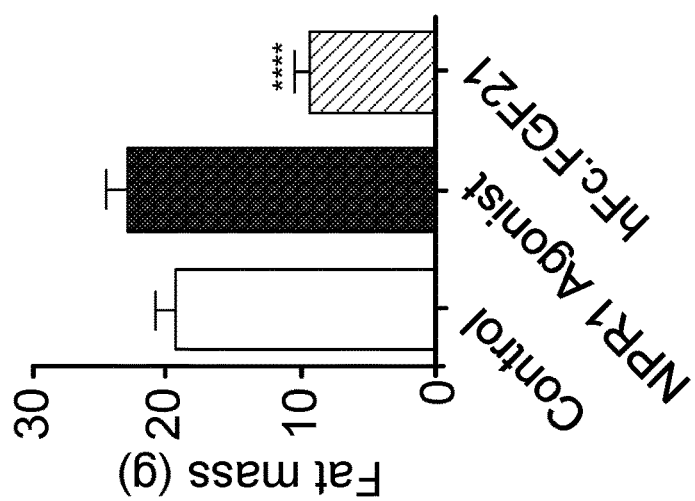
Figure 21A:
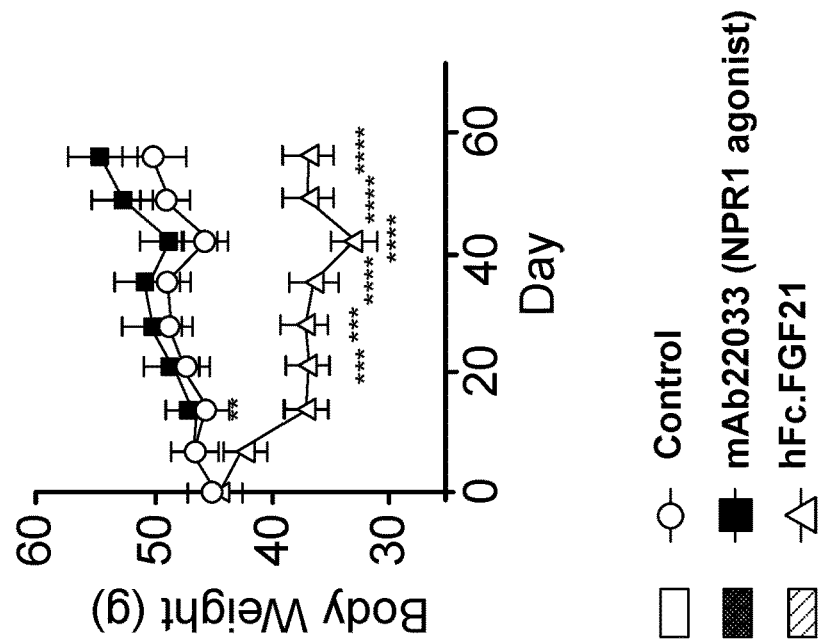
FIG. 21A shows changes in body weight following administration of mAb22033 NPR1 agonist mAb, hFc.FGF21 or an isotype control mAb.

FIG. 21A shows changes in body weight following administration of mAb22033 NPR1 agonist mAb, hFc.FGF21 or an isotype control mAb. FIG. 21B and FIG. 21C show total fat and total lean mass respectively after six weeks of treatment as measured by EchoMRI. The key findings are that while the hFc.FGF21 molecule produced significant reductions in body weight and adiposity over the treatment period, the mAb22033 NPR1 agonist antibody did not.

FIGS. 22A-C show changes in VO$_2$ (A), VCO$_2$ (B) or Energy Expenditure (C) broken down as the average of each day/night cycle after one week of treatment with either mAb22033 NPR1 agonist mAb, hFc.FGF21 or an isotype control mAb. The key findings are that while the hFc.FGF21 molecule produced significant increases in VO$_2$, VCO$_2$ and energy expenditure over the treatment period, the mAb22033 NPR1 agonist antibody did not.

Figure 23B:
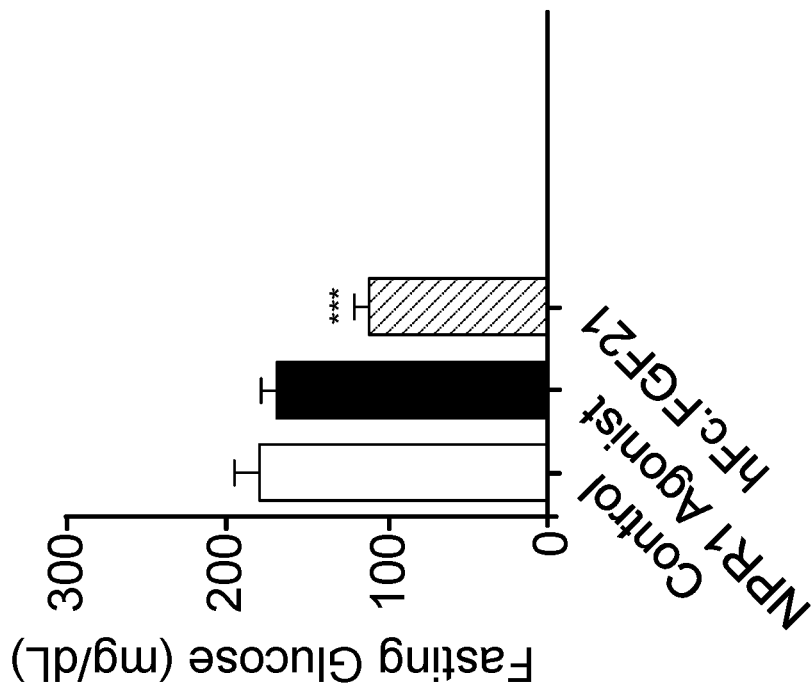
FIGS. 23A and 23B show the effects of anti-NPR1 antibody mAb22033 on glucose tolerance, as shown by blood glucose (FIG. 23A) and fasting glucose (FIG. 23B) levels. After four weeks of treatment, mice from each group were fasted overnight in clean cages and given an oral glucose load of 2 g/kg the following morning. Glucose was then recorded by tail vein using a hand-held glucometer at T0, T15, T30, T60, T90 and T120. A human IgG4 antibody was used as isotype control. All values are mean ±SEM, n=10 per group. hFc.FGF21 group: *=P<0.001 vs isotype control, **=P<0.0001 vs isotype control. mAb22033 group: +=P<0.05 vs isotype control, ++=P<0.01 vs isotype control. Statistics by two-way ANOVA+Bonferonni for the oGTT, one-way ANOVA+Bonferonni for the fasting glucose.
Figure 23A:
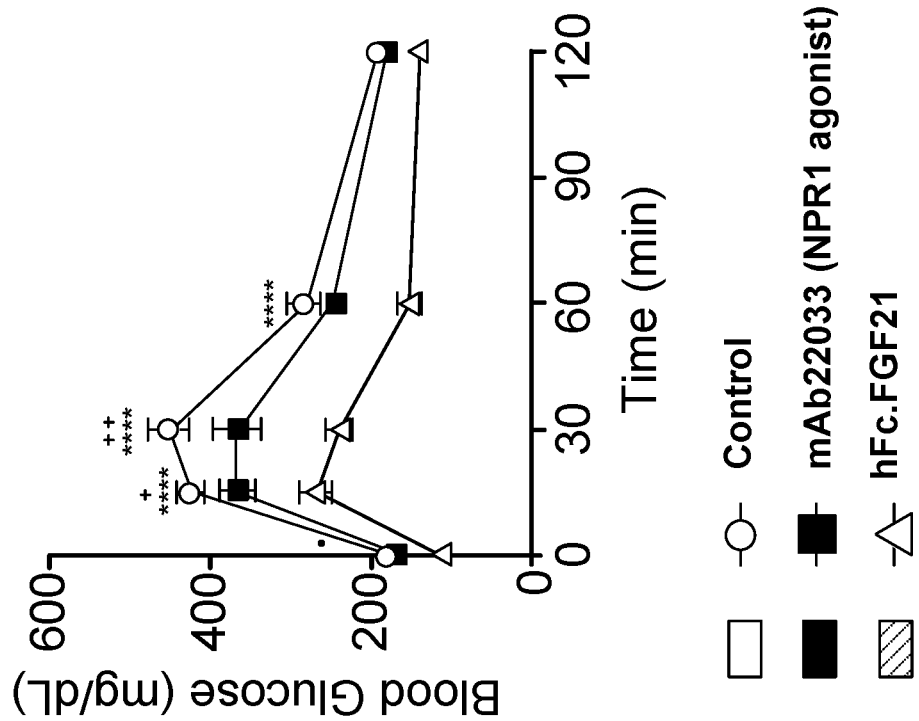

FIG. 23A shows changes in glucose tolerance as measured by an oral glucose tolerance test (2 g/kg glucose) after four weeks of treatment with either mAb22033 NPR1 agonist mAb, hFc.FGF21 or an isotype control mAb. FIG. 23B shows glucose levels following an overnight fast as recorded at the start of the study in A. The key finding is that both the mAb22033 and hFc.FGF21 molecules produced significant improvements in glucose tolerance after two weeks. Furthermore, the improvement in glucose tolerance by mAb22033 was independent of changes in body weight or energy expenditure (as shown in FIGS. 21 and 22).

Example 12: HDX Epitope Mapping

In order to determine the epitopes of human NPR1 recognized by anti-NPR1 antibodies, hydrogen-deuterium exchange (HDX) studies were carried out for mAb22033 and mAb22810, respectively. Prior in-house experiments show that the binding of NPR1 to mAb22810 requires the presence of ANP peptide. Hence, in addition to conventional HDX experiment using NPR1/mAb22033 complex, HDX experiments were also performed for NPR1/ANP/mAb22033 and NPR1/ANP/mAb22810 complexes.

For this study, anti-NPR1 antibodies (mAb22033 and mAb22810) were covalently attached to N-hydroxysuccinimide (NHS) agarose beads (GE Lifescience, cat #17-0906-01) according to manufacturer's protocol. CHO cell-expressed recombinant human NPR1 protein comprising the ecto domain of human NPR1 protein (Uniprot accession #P16066) with a C-terminal myc-myc-hexahistidine tag (SEQ ID NO: 194). ANP peptide was purchased from TOCRIS (cat #1906).

The deuteration buffer was prepared in $D_2O$ containing 137 mM NaCl, 2.7 mM KCl, 8 mM $Na_2HPO_4$, and 2 mM $KH_2PO_4$ (pD=7.4). For either "antigen-on" or "complex-on" experiments, 30 µL antibody bead slurry (equiv. 15 µL beads) was mixed with hNPR1.mmh or hNPR1.mmh/ANP complex. The mixture was incubated at room temperature with gentle rotation. The deuteration was quenched along with the elution of hNPR1.mmh from the antibody beads using 0.075% ice-cold TFA. The quenched sample was immediately injected into a Waters HDX Manager for online pepsin digestion (Waters Enzymate BEH pepsin column, 2.1×30 mm). The digested peptides were trapped onto an ACQUITY UPLC BEH C18 1.7 µm, 2.1×5 mm VanGuard pre-column at 0° C. and eluted to an ACQUITY UPLC BEH C18 1.7 µm, 2.1×50 mm column using an 8-minute gradient separation of 1%-30% B (mobile phase A: 0.1% formic acid in water, mobile phase B: 0.1% formic acid in acetonitrile). The mass spectrometer was set at cone voltage of 37 V, scan time of 0.5 s, and mass/charge range of 50-1700 Th.

To map the hNPR.mmh binding epitope recognized by mAb22033, two sets of H/D exchange experiments were carried out. The first experiment used an "antigen-on" format (HDX of antigen alone followed by binding to antibody beads). For the "antigen-on" experiment, hNPR1.mmh was deuterated for 3 and 8 minutes (in two separate sub-experiments) in phosphate buffer prepared in $D_2O$ (PBS-D, pD=7.4) at room temperature. Deuterated hNPR1.mmh was subsequently added to the PBS-D-washed mAb22033 beads for a 2-minute incubation at room temperature, resulting in a total deuteration time of 5 minutes and 10 minutes, respectively. The bound hNPR.mmh was then eluted from the beads using an ice-cold 0.075% aqueous trifluoroacetic acid (TFA) solution. The eluted hNPR.mmh was immediately injected into a Waters HDX manager system for online pepsin digestion followed by peptic peptide mass measurement.

The second experiment is referred to as the "complex-on" format (HDX of complexed antigen/antibody beads). For this experiment, hNPR.mmh was first bound to the mAb22033 beads in regular PBS (pH=7.4) for 2 minutes. The complex was then incubated in PBS-D (pD=7.4) for 5 or 10 minutes (in separate sub-experiments) for deuteration. The following steps (elution, injection, pepsin digestion, and MS analysis) were carried out as described in the preceding "antigen-on" procedure.

For peptide identification and deuterium uptake measurements, LC-$MS^E$ data from un-deuterated hNPR1.mmh were first processed and searched against the database including hNPR1.mmh via Waters ProteinLynx Global Server (PLGS) software. The identified peptides were imported to DynamX software and filtered by two criteria: 1) minimum products per amino acid: 0.3, and 2) replication file threshold: 2. DynamX software was then able to determine the deuterium uptake of each peptide from the "antigen-on", "complex-on" experiments based on each peptide's retention time and mass accuracy (<30 ppm) across two time points. All identified peptides were inspected and screened manually to minimize false positive hits.

The centroid values or average mass-to-charge ratios (m/z) of all the detected peptides were calculated and compared between the "antigen-on" and "complex-on" experiments at two time points. Peptides exhibiting increased mass after the "antigen-on" deuteration compared to the "complex-on" deuteration include amino acids protected from deuterium exchange as a result of antibody binding and therefore reveal binding epitope regions.

For NPR1/mAb22033 HDX experiment, a total of 101 peptides from hNPR1.mmh were identified, representing 74% sequence coverage. Among these peptides, ten peptides covering amino acids spanning from 29-50 and 328-347 had significant increased mass after the "antigen-on" deuteration compared to the "complex-on" deuteration as listed in Table 46.

TABLE 46

The effect on H/D exchange of mAb22033 binding to hNPR1.mmh as measured by $MH^+$ values of peptic peptides

| NPR1-mmH Residues | 5 min Deuteration | | | 10 min Deuteration | | |
|---|---|---|---|---|---|---|
| | Antigen-on | Complex-on | Δ | Antigen-on | Complex-on | Δ |
| 29-50 | 2426.346 | 2424.541 | 1.80 | 2426.649 | 2424.925 | 1.72 |
| 32-50 | 2128.200 | 2126.776 | 1.42 | 2128.488 | 2127.088 | 1.40 |
| 46-54 | 950.481 | 950.333 | 0.15 | 950.549 | 950.527 | 0.02 |
| 328-335 | 925.039 | 925.027 | 0.01 | 925.065 | 925.030 | 0.03 |
| 328-347 | 2084.447 | 2081.863 | 2.58 | 2084.306 | 2081.925 | 2.38 |
| 329-347 | 1921.240 | 1918.335 | 2.91 | 1921.305 | 1918.614 | 2.69 |
| 331-347 | 1679.173 | 1677.107 | 2.07 | 1679.106 | 1677.176 | 1.93 |
| 332-347 | 1607.797 | 1605.754 | 2.04 | 1607.799 | 1605.842 | 1.96 |
| 334-347 | 1407.379 | 1405.529 | 1.85 | 1407.335 | 1405.612 | 1.72 |
| 335-347 | 1278.196 | 1276.411 | 1.78 | 1278.225 | 1276.463 | 1.76 |
| 336-347 | 1176.174 | 1174.913 | 1.26 | 1176.181 | 1174.926 | 1.26 |
| 337-347 | 1063.079 | 1061.760 | 1.32 | 1063.014 | 1061.745 | 1.27 |

Since two peptides, amino acids 46-54 and 328-335 did not show deuterium uptake difference between the "antigen-on" and "complex-on" procedures, the regions of protection from deuterium exchange in the 29-50 and 328-347 peptides are reduced to residues 29-45 and 336- 347. Therefore, two segments including amino acids 29-45 and 336-347 are identified as the epitope for antibody mAb22033 binding to the hNPR1.mmh protein.

For NPR1/ANP/mAb22033 HDX experiment, a total of 95 peptides from hNPR.mmh were identified, representing 68% sequence coverage. Among these peptides, nine peptides covering amino acids spanning from 29-50 and 331-347 had significant increased mass after the "antigen-on" deuteration compared to the "complex-on" deuteration as listed in Table 47.

TABLE 47

The effect on H/D exchange of mAb22033 binding to hNPR1.mmh/ANP as measured by $MH^+$ values of peptic peptides

| NPR1-mmH | 5 min Deuteration | | | 10 min Deuteration | | |
|---|---|---|---|---|---|---|
| Residues | Antigen-on | Complex-on | Δ | Antigen-on | Complex-on | Δ |
| 29-50 | 2425.746 | 2424.277 | 1.47 | 2426.686 | 2425.079 | 1.61 |
| 32-50 | 2127.514 | 2126.429 | 1.08 | 2128.333 | 2127.126 | 1.21 |
| 35-50 | 1828.391 | 1827.331 | 1.06 | 1829.026 | 1827.974 | 1.05 |
| 46-54 | 950.149 | 950.080 | 0.07 | 950.312 | 950.323 | −0.01 |
| 331-347 | 1679.030 | 1677.150 | 1.88 | 1679.016 | 1677.216 | 1.80 |
| 332-347 | 1607.700 | 1605.825 | 1.88 | 1607.738 | 1605.943 | 1.79 |
| 334-347 | 1407.282 | 1405.558 | 1.72 | 1407.271 | 1405.715 | 1.56 |
| 335-347 | 1278.028 | 1276.463 | 1.56 | 1278.087 | 1276.658 | 1.43 |
| 336-347 | 1176.211 | 1175.009 | 1.20 | 1176.186 | 1175.009 | 1.18 |
| 337-347 | 1063.036 | 1061.743 | 1.29 | 1063.019 | 1061.807 | 1.21 |

Since another peptide, amino acids 46-54, did not show deuterium uptake difference between the "antigen-on" and "complex-on" procedures, the region of protection from deuterium exchange in the 29-50 peptide is reduced to residues 29-45. Therefore, two segments including amino acids 29-45 and 331-347 are identified as the epitope for antibody mAb22033 binding to the hNPR1.mmh/ANP protein complex.

For NPR1/ANP/mAb22810 HDX experiment, a total of 93 peptides from hNPR.mmh were identified, representing 70% sequence coverage. Among these peptides, ten peptides covering amino acids spanning from 29-50, 70-81 and 331-347 had significant increased mass after the "antigen-on" deuteration compared to the "complex-on" deuteration as listed in Table 48.

TABLE 48

The effect on H/D exchange of mAb22810 binding to hNPR1.mmh/ANP as measured by $MH^+$ values of peptic peptides

| NPR1-mmH | 5 min Deuteration | | | 10 min Deuteration | | |
|---|---|---|---|---|---|---|
| Residues | Antigen-on | Complex-on | Δ | Antigen-on | Complex-on | Δ |
| 29-50 | 2426.295 | 2425.324 | 0.97 | 2426.927 | 2426.077 | 0.85 |
| 32-50 | 2128.086 | 2127.361 | 0.72 | 2128.584 | 2128.016 | 0.57 |
| 33-50 | 2056.507 | 2056.083 | 0.42 | 2056.723 | 2056.405 | 0.32 |
| 35-50 | 1828.973 | 1828.597 | 0.38 | 1829.278 | 1828.952 | 0.33 |
| 46-54 | 950.063 | 950.090 | −0.03 | 950.267 | 950.087 | 0.18 |
| 70-81 | 1456.036 | 1455.661 | 0.37 | 1456.127 | 1455.699 | 0.43 |
| 72-81 | 1241.898 | 1241.496 | 0.40 | 1241.969 | 1241.536 | 0.43 |
| 331-347 | 1678.712 | 1678.316 | 0.40 | 1678.888 | 1678.589 | 0.30 |
| 332-347 | 1607.457 | 1607.060 | 0.40 | 1607.617 | 1607.323 | 0.29 |
| 334-347 | 1407.018 | 1406.698 | 0.32 | 1407.217 | 1406.970 | 0.25 |
| 335-347 | 1277.816 | 1277.550 | 0.27 | 1278.075 | 1277.824 | 0.25 |
| 336-347 | 1175.926 | 1175.894 | 0.03 | 1176.094 | 1176.051 | 0.04 |
| 337-347 | 1062.703 | 1062.646 | 0.06 | 1062.844 | 1062.767 | 0.08 |

Since three peptides, amino acids 46-54, 336-347, 337-347 did not show deuterium uptake difference between the "antigen-on" and "complex-on" procedures, the regions of protection from deuterium exchange in the 29-50, and 331-347 peptides are reduced to residues 29-45 and 331-335. Therefore, three segments including amino acids 29-45, 70-81 and 331-335 are identified as the epitope for antibody mAb22810 binding to the hNPR1.mmh/ANP protein complex.

Example 13: Intravitreal Injection of NPR1 Antibody in Humanized NPR1 Mice Lowers Intraocular Pressure This Example describes the effect of an intravitreal injection (IVT) of exemplary human NPR1 antibody mAb22033 on intraocular pressure (IOP) in humanized NPR1 mice.

Methods: Humanized NPR1 mice (NPR1$^{hu/hu}$) were generated with VelociGene technology (Regeneron). A single IVT injection of 40 μg mAb22033or control Ab was performed in humanized NPR1 or wild-type (WT) mice. IOP was measured daily for four days after injection. In a second experiment, to examine the dose response, 40, 12.6, or 4 μg mAb22033or 40 μg control Ab was injected intravitreally, and IOP was monitored daily. In another experiment, to test the effect of long-term delivery Ab, AAV2 vectors expressing NPR1 antibody or eGFP were injected, IOP was followed up for 7 weeks.

Results: IVT of 40 μg mAb22033 into NPR1$^{hu/hu}$ mice significantly reduced IOP from Day 1 to 3 compared to control antibody. Average IOP change was 5 mmHg. However, in WT mice there was no IOP lowering effect. Dose response study showed that 40 or 12.6 μg IVT of mAb22033 had similar IOP lowering effect, while the effect of 40 μg mAb22033 lasted longer than 12.6 μg. IVT of 4 μg NPR1 antibody did not reduce IOP. No IOP effect was found after IVT AAV2-GFP or AAV2-NPR1 antibody at all experimental time points. This could be due to the low expression of NPR1 antibody i.e. only 10 ng in the whole eye lysate was detected.

Conclusion: IVT administration of human NPR1 antibody (mAb22033) in humanized NPR1 mice reduced IOP significantly, thus demonstrating the potential of agonist anti-NPR1 antibodies for lowering IOP in glaucoma disease.

Example 14: Structural Analysis of the Antibody-NPR1 Complex by Electron Microscopy Methods
Size Exclusion Chromatography with Multi Angle Light Scattering (SEC-MALS) Titrations Several titration series of human NPR1 extracellular domain with a C-terminal myc-myc-6×His tag (hNPR1-mmh; SEQ ID NO: 194) complexed with various antibodies at different molar ratios were prepared. The antibodies tested were: mAb22033, REGN5308 (Fab fragment of mAb22033), mAb22810, and REGN5314 (Fab fragment of mAb22810). All titration series were done both with and without Atrial Natriuretic factor (ANP, Tocris) at a 2-fold molar excess relative to hNPR1-mmh. After overnight incubation in PBS at 4° C., the complexes were injected into the SEC-MALS system, which consists of a Superdex 200 Increase 10/300 GI column on an ÄKTA micro system (GE Healthcare Life Sciences), followed by a miniDAWN Treos and Optilab T-rEX (Wyatt Technology Corporation). Since phosphate buffers are incompatible with electron microscopy negative staining, the SEC column was equilibrated in 50 mM Tris pH 7.5, 150 mM NaCl running buffer, and all of the larger scale complexes prepared below were in this buffer. Size exclusion chromatography data was evaluated using Unicorn (Version 5.20 General Electric Company), and the MALS data was evaluated using ASTRA (Version 7.0.0.69 Wyatt Technology).

Negative Stain Electron Microscopy Sample Preparation

Complexes of hNPR1 were prepared on a larger scale to use in negative-stain electron microscopy. Five samples were prepared as follows: Sample 1=hNPR1-mmh (SEQ ID NO: 194) alone; Sample 2=hNPR1-Fc (SEQ ID NO: 197) alone; Sample 3=hNPR1-mmh+ANP, 1:2 molar ratio; Sample 4=hNPR1-mmh+REGN5308, 1:1.5 molar ratio; Sample 5=hNPR1-mmh+ANP+REGN5308, 1:2:1.5 molar ratio. Samples 1, 3, 4, and 5 were purified by size exclusion chromatography in the same manner as the SEC-MALS experiments. Peak fractions were collected, frozen at −80 C, and sent to NanoImaging Services, Inc. for EM analysis. Sample 2 was taken directly from a 2.62 mg/ml stock solution in PBS, buffer exchanged to 50 mM Tris, pH 7.5+150 mM NaCl, diluted to 1.5 mg/ml, frozen at −80 C, and sent with the other samples.

Negative Stain Electron Microscopy Data Collection and Processing

The five protein samples were prepared negative stain EM grids in the standard manner using uranyl formate (NanoImaging Services). Grids contained a thin layer of continuous carbon placed over a C-flat holey carbon grid. TEM images were collected at room temperature on a Tecnai T12 electron microscope (FEI/Thermo Fisher) operating at 120 keV with an FEI Eagle 4 k×4 k CCD camera. Images were collected at a variety of nominal magnifications, primarily 67,000× and 110,000×. The collected images were further processed in-house.

The NanoImaging micrographs by eye were inspected by eye, and images that had poor stain contrast were removed, about ⅕ of the total images. The remaining images were separated by magnification; the 110,000× images were not as useful for further analysis since they had fewer particles per image. Therefore, all subsequent processing steps were done using the 67,000× images. All images were CTF-corrected using CTFFIND4.

EM Particle Picking and 2D Class Averaging

The particle distributions for all five negative stain samples were quite good, with uniform particle size, very little clumping, and a good particle density. In Samples 4 and 5, particles were picked using Relion, with autopicking templates derived from an initial round of manual picking and 2D class averaging. For Sample 4 (hNPR1+REGN5308), 19184 good particles were selected from a total of 75 micrographs. For Sample 5 (hNPR1+ANP+REGN5308), 20318 good particles were initially selected from a total of 88 micrographs. Initial 2D class averaging using Relion revealed substantial heterogeneity in both datasets, with a substantial number of classes showing REGN5308 Fab only, or NPR1 only.

The 2D class averaging for Sample 5 was refined further by eliminating particles corresponding to Fab only or NPR1 only. The remaining 9219 particles were used to calculate new 2D class averages, which showed a better distribution of views for the NPR1+REGN5308 complex, and revealed that a minority of the complexes contained only one Fab bound to the NPR1 dimer, while the majority of the complexes contained two Fabs. Removing the one-Fab complexes reduced the particle set further to 6728 particles.

3D Image Reconstruction from Negative Stain EM Data

An initial 3D model of the NPR1-ANP-REGN5308 complex was constructed in Relion, using the stochastic gradient descent "3D initial model" procedure, with resolution limited to 40 Å. This model was then further low-pass filtered to 60 Å and used as a reference for 3D classification in Relion of the 6728 particles mentioned above, with expectation step resolution limited to 25 Å. The best 3D class was then further refined in Relion until convergence, with a final resolution of 22 Å as measured by the "gold standard" FSC. We did not impose 2-fold symmetry during the 3D classification or refinement. The density map resulting from the 3D reconstruction clearly showed two Fabs bound on one side of a square particle consistent with the crystal structure of ANP-bound NPR1 (PDB code 1T34).

Cryo-Electron Microscopy Sample Preparation and Data Collection

A sample of the NPR1-ANP-REGN5308 complex was prepared for cryo-electron microscopy (cryoEM) in the same manner as the negative stain EM sample described above. The final complex concentration was 0.8 mg/ml in 50 mM Tris, pH 7.5, 150 mM NaCl. CryoEM samples were prepared with standard techniques, using UltrAuFoil grids (Quantifoil Micro Tools GmbH) and a Vitrobot (FEI/Thermo Fisher). Data collection was done on a Titan Krios electron microscope operating at 300 kV (FEI/Thermo Fisher) using a K2 direct electron detector in counting mode, and GIF energy filter (Gatan, Inc.). 1409 movies were collected at a magnification of 130,000× (1.04 Å/pixel) with a defocus range of −0.5 to −1.5 microns, and a total dose of 45.44 $e^-/Å^2$. Data collection was controlled by Leginon software.

CryoEM Data Processing and Structure Determination

All cryoEM movies were motion-corrected, dose-weighted, and CTF corrected using the cisTEM package. Images were then manually inspected to remove those with thick ice, poor CTF parameters (fit resolution worse than 6 Å), no particles, contamination, etc. 1172 images remained after this filter, which were then used for non-templated particle picking in cisTEM, yielding 872915 particle positions. After 2D classification to remove the bad particles, 686709 particles were included in 3D auto-refinement using cisTEM, with a starting 3D reference volume generated ab initio. The 3D refinement converged to a single solution with a resolution of 2.8 Å estimated from the Fourier Shell Correlation curve.

This 3D map was then used for structure refinement, starting from a model built into the negative stain EM 3D map mentioned above. The N- and C-terminal domains of both NPR1 molecules were real-space refined as rigid bodies into the EM map, and then manually rebuilt in the few places where the model did not match the EM density. The REGN5308 homology model was manually placed into the EM density; careful inspection of the CDR regions allowed us to determine the orientation of the heavy vs. light chains. The CDR regions of the model needed extensive rebuilding to match the EM density. Finally, real-space positional refinement using Phenix produced the current structural model of the complex.

Results/Discussion

Size Exclusion Chromatography with Multi Angle Light Scattering (SEC-MALS) Titrations In interactions of hNPR1-mmh with mAb22033, hNPR1-mmh by itself behaves as a dimer with a molecular weight of approximately 110 kDa in the presence and absence of ANP, with a slight increase in molecular weight upon ANP binding to NPR1. No free monomer peak was observed for hNPR1-mmh by itself. Titrations with mAb22033 in the absence of ANP revealed two main species of the complex: a species with molecular weight equal to one IgG bound to one NPR1 dimer, and a species with molecular weight equal to one IgG bound to two NPR1 dimers. However, NPR1 plus mAb22033 in the presence of ANP formed higher molecular weight species that could represent "paper-doll" polymers of NPR1 and IgG.

The system was subsequently simplified by considering REGN5308, the Fab fragment of mAb22033. Complexes of hNPR1-mmh and REGN5308 show a very different SEC profile with bound ANP compared to the same complexes without ANP. The NPR1-REGN5308 complex has a molecular weight of approximately 155 kDa, consistent with one Fab bound per NPR1 dimer. In the presence of ANP, the NPR1-ANP-REGN5308 complex molecular weight increases by ~50 kDa, consistent with two Fabs bound per NPR1 dimer. We propose that the previously-described conformational change in NPR1 upon ANP binding (Ogawa, H et. al, 2004) permits the second Fab to bind, and that the 2 Fab+2 NPR1+ANP complex is necessary for the growth of the paper-doll polymers observed with the full IgG mAb22033 (see below for further discussion).

Titrations with hNPR1-mmh and mAb22810 were also carried out. SEC-MALS analysis showed that a small fraction of the mAb22810 sample was dimeric, with a molecular weight of approximately 315 kDa compared to the standard IgG molecular weight of 150 kDa. SEC-MALS titrations with the NPR1- mAb22810-ANP complex showed a heterogeneous mixture of species in the 430-700 kDa range; this profile was too complex to be reliably interpreted, perhaps due to the IgG dimer impurity in the mAb22810 protein. SEC-MALS titrations with REGN5314, the Fab fragment of mAb22810, showed that REGN5314 binding to NPR1 in the absence of ANP is too weak or transient to produce a complex species that can be isolated by SEC. When ANP is present, a single NPR1-REGN5314-ANP complex is formed with a molecular weight of approximately 170 kDa, consistent with one Fab bound per NPR1 dimer.

Negative Stain 2D Class Averages

The hNPR1+REGN5308 and the hNPR1+ANP+REGN5308 complexes were further analyzed by negative stain electron microscopy. 2D classification and averaging of the complex particles revealed substantial heterogeneity in the samples. A large fraction of the particles on the EM grids could be classified as hNPR1 only, or as REGN5308 Fab only. Since the protein samples submitted for imaging were purified, homogeneous complexes, it appears that these complexes are dissociating into their components during the process of negative stain grid preparation. However, a good portion of the complexes remained intact and can be used for analysis.

The negative stain 2D class averages of hNPR1+REGN5308 show a "one armed" complex, in which only a single Fab can be seen binding to the hNPR1 dimer, consistent with the SEC-MALS results. In contrast, the negative stain 2D class averages of hNPR1+ANP+REGN5308 show a "two armed" complex, with two Fabs bound to the dimer. Different averages represent different projection views of the real three-dimensional complex. In one class average, the hNPR1 dimer is seen in a side view, with two lobes of density: one corresponding to the N-terminal domains of the two monomers superimposed on each other, and the other lobe corresponding to the two superimposed C-terminal domains. In this orientation, the two bound Fabs look like "rabbit ears" sitting on top of the NPR1 density. In a different view, all four domains of hNPR1 can be seen as four blobs of density forming a square, with the two REGN5308 Fabs above the square, crossing over each other to make an inverted V. The hNPR1+ANP+REGN5308 class averages also showed "one armed" complexes, but these are likely due to the same complex dissociation that produced free Fab and free NPR1.

2D class averages calculated from the hNPR1+ANP+REGN5308 cryoEM data show different views of the complex compared to the negative stain data; in particular, the "rabbit ears" orientation is not present. However, other cryoEM 2D class averages can be matched closely to the corresponding averages in the negative stain data. We do not see as much evidence of complex dissociation in the cryoEM data, probably because the starting sample is more homogeneous, and also because the cryo-freezing conditions better preserve the native conformation of the complex in solution.

3D Image Reconstruction

A three-dimensional map of the cryoEM density for hNPR1+ANP+REGN5308 was constructed using the 2D class averages as a starting point. This reconstruction procedure does not require any prior information about the expected shape or size of the complex, beyond a rough estimate of the complex diameter, so the resulting cryoEM map is unbiased by our expectations of how the antibody-target complex should be formed. The known crystal structure of hNPR1+ANP was then placed and refined into this EM density map, along with models of the REGN5308 Fabs generated by homology to known Fab structures. The NPR1 and Fab structures were placed in their approximate locations by hand, and then refined as rigid bodies into the correct locations using Phenix. The resolution of the cryoEM maps is sufficient to permit manual rebuilding of the residues at the NPR1:antibody contact interface, particularly the residues of the REGN5308 complementarity-determining regions (CDRs), which cannot be accurately modeled by homology. The current structural model has placed all antibody CDR residues as well as the NPR1 residues in contact with them. More distant regions of the model (NPR1 C-terminal domains, and the constant domains of the antibody Fabs) have been modeled through a combination of the current cryoEM map and previously-determined X-ray crystal structure information for NPR1 (PDB code 1T34) and isolated antibody structures.

mAb22033 Epitope on NPR1: Inspection of the hNPR1+ANP+REGN5308 structure reveals which residues of NPR1 are contacted by the REGN5308 Fab (and by extension, the parental IgG mAb22033). This epitope is composed of four separate stretches of amino acids in NPR1 which combine to form a continuous surface in three dimensions: residues 2-4, 41-45, 47, 73-79, 332, 336-344, and 347 (numbered according to SEQ ID NO: 194). Earlier hydrogen/deuterium exchange (HDX) mass spectrometry experiments identified some of these residues as significant (see Example 12), but the cryoEM structure provides finer detail of the epitope.

Structural Mechanism of Action for mAb22033

The two Fabs in this model of the NPR1-antibody complex come within ~10 Å of each other at a point near the "elbow" between Fab variable domains and Fab constant domains. The C termini of these two Fabs are much farther apart, approximately 100 Å, and therefore could not be the two arms of a single IgG molecule. The Fabs do not come particularly close to the modeled ANP peptide (roughly 30 Å distance at closest approach), and it does not seem that there is any direct interaction between Fab and ANP.

If we assume a fixed position and relative orientation of the Fab relative to its binding site on the N-terminal domain of NPR1, then an explanation of the ANP-dependent binding of the REGN5308 Fab emerges. NPR1 has been shown to undergo a conformational change upon ANP binding, in which one NPR1 monomer rotates relative to the other while remaining dimerized. Applying this rotation to one-half of the 2 NPR1+2 Fab complex produces a model in which the NPR1 dimer resembles the crystal structure of ANP-free NPR1. However, one of the REGN5308 Fabs has now rotated into a position where it sterically clashes with the other Fab, a physically impossible situation. This steric interference is the reason why only one REGN5308 Fab can bind to the NPR1 dimer in the absence of ANP: both antibody binding sites on the two monomers are equally accessible but binding of the first Fab blocks binding of the second Fab.

If we consider this effect from the other side, the binding of two Fabs to an ANP-containing NPR1 dimer will prevent this complex from relaxing back to the ANP-free conformation, so long as both Fabs are bound. At equilibrium, this would cause a larger fraction of the NPR1 molecules to be in an active state capable of downstream signaling—if we assume that the effects we see here are preserved on the surface of a cell. Another possible effect of antibody binding is the formation of oligomeric clusters of antibody with NPR1+ANP as described above. This effect is only possible if each NPR1 dimer can bind two Fab arms from two separate IgG molecules; in the absence of ANP, only one Fab arm can bind to each NPR1 dimer, and the complex formation stops with a much smaller species containing at most one IgG with an NPR1 dimer bound to each Fab arm. Both of these effects, receptor clustering and prolongation of receptor active state, could explain the activating effect of mAb22033 on the NPR1 receptor.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated polynucleotide molecule comprising a polynucleotide sequence that encodes a HCVR and/or LCVR of an antibody or antigen-binding fragment thereof that binds specifically to natriuretic peptide receptor 1 (NPR1) protein, wherein the antibody or antigen-binding fragment thereof comprises three heavy chain complementarity determining regions (CDRs) (HCDR1, HCDR2 and HCDR3) contained within a heavy chain variable region (HCVR) comprising an amino acid sequence of SEQ ID NO:2; and three light chain CDRs (LCDR1, LCDR2 and LCDR3) contained within a light chain variable region (LCVR) comprising an amino acid sequence of SEQ ID NO: 10.

2. The isolated polynucleotide molecule of claim 1, wherein the antibody or antigen-binding fragment thereof comprises a HCVR having an amino acid sequence of SEQ ID NO: 2.

3. The isolated polynucleotide molecule of claim 1, wherein the antibody or antigen-binding fragment thereof comprises a LCVR having an amino acid sequence of SEQ ID NO: 10.

4. The isolated polynucleotide molecule of claim 1, wherein the antibody or antigen-binding fragment thereof comprises:
   (a) a HCDR1 having an amino acid sequence of SEQ ID NO: 4;
   (b) a HCDR2 having an amino acid sequence of SEQ ID NO: 6;
   (c) a HCDR3 having an amino acid sequence of SEQ ID NOs: 8;
   (d) a LCDR1 having an amino acid sequence of SEQ ID NO: 12;
   (e) a LCDR2 having an amino acid sequence of SEQ ID NO: 14; and
   (f) a LCDR3 having an amino acid sequence of SEQ ID NO: 16.

5. The isolated polynucleotide molecule of claim 1, wherein the antibody or antigen-binding fragment thereof comprises a HCVR/LCVR amino acid sequence pair of SEQ ID NOs: 2/10.

6. The isolated polynucleotide molecule of claim 1, wherein the antibody or antigen-binding fragment thereof interacts with one or more amino acids contained within the extracellular domain of NPR1 (amino acids 29-347 of SEQ ID NO: 194), as determined by hydrogen/deuterium exchange, and wherein the antibody or antigen-binding fragment thereof: (i) binds to cells expressing human NPR1 in the presence or absence of atrial natriuretic peptide (ANP); and/or (ii) activates NPR1.

7. The isolated polynucleotide molecule of claim 1, wherein the antibody or antigen-binding fragment thereof interacts with an amino acid sequence selected from the group consisting of (a) amino acids 29 to 45 of SEQ ID NO: 194; and (b) amino acids 336 to 347 of SEQ ID No: 194.

8. The isolated polynucleotide molecule of claim 1, wherein the antibody or antigen-binding fragment thereof interacts with an amino acid sequence selected from the group consisting of (a) amino acids 29 to 45 of SEQ ID NO: 194; and (b) amino acids 331 to 347 of SEQ ID No: 194, in the presence of ANP.

9. The isolated polynucleotide molecule of claim 1, wherein the antibody is a fully human monoclonal antibody.

10. The isolated polynucleotide molecule of claim 1, wherein the antibody has one or more properties selected from the group consisting of: (a) is a fully human monoclonal antibody; (b) binds to monomeric human NPR1 in the absence of ANP and/or brain natriuretic peptide (BNP) at 25° C. and at 37° C. with a dissociation constant (KD) of less than 690 nM, as measured in a surface plasmon resonance assay; (c) binds to dimeric human NPR1 in the absence of ANP or BNP at 25° C. and at 37° C. with a KD of less than 42 nM, as measured in a surface plasmon resonance assay; (d) binds to human NPR1 complexed to ANP at 25° C. and 37° C. with a KD of less than 80 nM, as measured in a surface plasmon resonance assay; (e) binds to human NPR1 complexed to BNP at 25° C. and 37° C. with a KD of less than 20 nM, as measured in a surface plasmon resonance assay; (f) binds to monomeric monkey NPR1 in the absence of ANP and/or BNP at 25° C. and 37° C. with a KD of less than 365 nM, as measured in a surface plasmon resonance assay; (g) binds to dimeric monkey NPR1 in the absence of ANP or BNP at 25° C. and at 37° C. with a KD of less than 30 nM, as measured in a surface plasmon resonance assay; (h) binds to monkey NPR1 complexed to ANP at 25° C. and 37° C. with a KD of less than 10 nM, as measured in a surface plasmon resonance assay; (i) binds to monkey NPR1 complexed to BNP at 25° C. and 37° C. with a KD of less than 10 nM, as measured in a surface plasmon resonance assay; (j) does not bind to mouse NPR1; (k) binds to cells expressing human NPR1 (without ANP) or NPR1-complexed to ANP with a EC50 less than 5 nM; (l) activates NPR1 with a EC50 of less than 385 nM, as measured in a calcium flux cell-based bioassay; (m) reduces the systemic blood pressure when administered to normotensive and hypertensive mice, wherein the reduction in systemic and mean arterial blood pressures lasts for up to 28 days upon administration of a single dose; and (n) improves glucose tolerance when administered to diet-induced obese mice.

11. A vector comprising the polynucleotide sequence of claim 1.

12. A host cell expressing the vector of claim 11.

13. A method of producing an anti-NPR1 antibody or antigen-binding fragment thereof, comprising growing the host cell of claim 12 under conditions permitting production of the antibody or fragment, and recovering the antibody or fragment so produced.

14. The method of claim 13, further comprising formulating the antibody or antigen-binding fragment thereof as a pharmaceutical composition comprising an acceptable carrier.

* * * * *